(12) United States Patent
Brister et al.

(10) Patent No.: US 8,808,228 B2
(45) Date of Patent: Aug. 19, 2014

(54) INTEGRATED MEDICAMENT DELIVERY DEVICE FOR USE WITH CONTINUOUS ANALYTE SENSOR

(75) Inventors: Mark C. Brister, Encinitas, CA (US); Nelson Quintana, San Diego, CA (US); Antonio C. Llevares, Chula Vista, CA (US); John Michael Dobbles, San Diego, CA (US); Richard C. Yang, Irvine, CA (US); Michael Robert Mensinger, San Diego, CA (US)

(73) Assignee: DexCom, Inc., San Diego, CA (US)

( * ) Notice: Subject to any disclaimer, the term of this patent is extended or adjusted under 35 U.S.C. 154(b) by 210 days.

(21) Appl. No.: 12/133,820

(22) Filed: Jun. 5, 2008

(65) Prior Publication Data
US 2008/0262469 A1    Oct. 23, 2008

Related U.S. Application Data

(63) Continuation-in-part of application No. 10/789,359, filed on Feb. 26, 2004, now Pat. No. 7,591,801.

(60) Provisional application No. 60/942,787, filed on Jun. 8, 2007.

(51) Int. Cl.
*A61M 31/00* (2006.01)
(Continued)

(52) U.S. Cl.
CPC ............ *A61B 5/0002* (2013.01); *A61B 5/14532* (2013.01); *A61B 2560/0443* (2013.01); *A61M 2205/583* (2013.01); *G06F 19/3468* (2013.01); *A61M 2230/201* (2013.01); *A61M 5/31525* (2013.01); *A61M 2205/582* (2013.01); *A61M 2205/581* (2013.01); *A61M 2205/3592* (2013.01); *A61M 2205/50* (2013.01); *A61M 5/003* (2013.01); *A61B 5/14546* (2013.01); *A61B 2560/0431* (2013.01); *A61B 5/1486* (2013.01); *A61M 2205/502* (2013.01); *A61M 5/1723* (2013.01); *A61B 5/4839* (2013.01); *A61M 5/24* (2013.01); *A61M 2205/3569* (2013.01); *A61B 2560/0406* (2013.01); *A61B 2560/04* (2013.01); *A61M 2205/3561* (2013.01)
USPC ................ 604/66; 604/65; 604/503; 604/504

(58) Field of Classification Search
USPC .......................... 604/66, 65, 503, 504, 131, 50
See application file for complete search history.

(56) References Cited

U.S. PATENT DOCUMENTS 2,719,797 A   10/1955   Rosenblatt et al.
(Continued)

FOREIGN PATENT DOCUMENTS

EP    0 098 592    1/1984
(Continued)

OTHER PUBLICATIONS

Aalders et al. 1991. Development of a wearable glucose sensor; studies in healthy volunteers and in diabetic patients. The International Journal of Artificial Organs 14(2):102-108.
(Continued)

*Primary Examiner* — Laura Bouchelle
(74) *Attorney, Agent, or Firm* — Knobbe, Martens, Olson & Bear, LLP.

(57) ABSTRACT

An integrated system for the monitoring and treating diabetes is provided, including an integrated receiver/hand-held medicament injection pen, including electronics, for use with a continuous glucose sensor. In some embodiments, the receiver is configured to receive continuous glucose sensor data, to calculate a medicament therapy (e.g., via the integrated system electronics) and to automatically set a bolus dose of the integrated hand-held medicament injection pen, whereby the user can manually inject the bolus dose of medicament into the host. In some embodiments, the integrated receiver and hand-held medicament injection pen are integrally formed, while in other embodiments they are detachably connected and communicated via mutually engaging electrical contacts and/or via wireless communication.

33 Claims, 20 Drawing Sheets

(51) Int. Cl.
*A61B 5/145* (2006.01)
*G06F 19/00* (2011.01)
*A61M 5/315* (2006.01)
*A61B 5/00* (2006.01)
*A61M 5/24* (2006.01)
*A61M 5/00* (2006.01)
*A61B 5/1486* (2006.01)
*A61M 5/172* (2006.01)

(56) References Cited

U.S. PATENT DOCUMENTS

| | | |
|---|---|---|
| 3,210,578 A | 10/1965 | Sherer |
| 3,219,533 A | 11/1965 | Mullins |
| 3,381,371 A | 5/1968 | Russell |
| 3,826,244 A | 7/1974 | Salcman et al. |
| 3,837,339 A | 9/1974 | Aisenberg |
| 3,898,984 A | 8/1975 | Mandel et al. |
| 3,943,918 A | 3/1976 | Lewis |
| 3,957,613 A | 5/1976 | Macur |
| 3,979,274 A | 9/1976 | Newman |
| 4,052,754 A | 10/1977 | Homsy |
| 4,240,438 A | 12/1980 | Updike et al. |
| 4,245,634 A | 1/1981 | Albisser et al. |
| 4,253,469 A | 3/1981 | Aslan |
| 4,319,578 A | 3/1982 | Enger |
| 4,374,013 A | 2/1983 | Enfors |
| 4,403,984 A | 9/1983 | Ash et al. |
| 4,442,841 A | 4/1984 | Uehara et al. |
| 4,477,314 A | 10/1984 | Richter et al. |
| 4,494,950 A | 1/1985 | Fischell |
| 4,535,786 A | 8/1985 | Kater |
| 4,554,927 A | 11/1985 | Fussell |
| 4,583,976 A | 4/1986 | Ferguson |
| 4,655,880 A | 4/1987 | Liu |
| 4,703,756 A | 11/1987 | Gough et al. |
| 4,731,726 A | 3/1988 | Allen |
| 4,750,496 A | 6/1988 | Reinhart et al. |
| 4,757,022 A | 7/1988 | Shults et al. |
| 4,805,624 A | 2/1989 | Yao et al. |
| 4,805,625 A | 2/1989 | Wyler |
| 4,831,070 A | 5/1989 | McInally et al. |
| 4,832,034 A | 5/1989 | Pizziconi |
| 4,841,974 A | 6/1989 | Gumbriecht et al. |
| 4,852,573 A | 8/1989 | Kennedy |
| 4,858,615 A | 8/1989 | Meinema |
| 4,883,057 A | 11/1989 | Broderick |
| 4,890,621 A | 1/1990 | Hakky |
| 4,919,141 A | 4/1990 | Zier et al. |
| 4,927,516 A | 5/1990 | Yamaguchi et al. |
| 4,944,299 A | 7/1990 | Silvian |
| 4,950,246 A * | 8/1990 | Muller .................... 604/154 |
| 4,953,552 A | 9/1990 | DeMarzo |
| 4,974,929 A | 12/1990 | Curry |
| 4,988,341 A | 1/1991 | Columbus et al. |
| 4,992,794 A | 2/1991 | Brouwers |
| 5,019,974 A | 5/1991 | Beckers |
| 5,034,112 A | 7/1991 | Murase et al. |
| 5,050,612 A | 9/1991 | Matsumura |
| 5,077,476 A | 12/1991 | Rosenthal |
| 5,097,834 A | 3/1992 | Skrabal |
| 5,101,814 A | 4/1992 | Palti |
| 5,108,819 A | 4/1992 | Heller et al. |
| 5,137,028 A | 8/1992 | Nishimura |
| 5,160,418 A | 11/1992 | Mullen |
| 5,165,407 A | 11/1992 | Wilson et al. |
| 5,190,041 A | 3/1993 | Palti |
| 5,208,147 A | 5/1993 | Kagenow et al. |
| 5,249,576 A | 10/1993 | Goldberger et al. |
| 5,262,305 A | 11/1993 | Heller et al. |
| 5,264,104 A | 11/1993 | Gregg et al. |
| 5,266,179 A | 11/1993 | Nankai et al. |
| 5,269,891 A | 12/1993 | Colin |
| 5,281,319 A | 1/1994 | Kaneko et al. |
| 5,282,848 A | 2/1994 | Schmitt |
| 5,284,140 A | 2/1994 | Allen et al. |
| 5,284,570 A | 2/1994 | Savage et al. |
| 5,299,571 A | 4/1994 | Mastrototaro |
| 5,307,263 A | 4/1994 | Brown |
| 5,312,361 A | 5/1994 | Zadini et al. |
| 5,314,471 A | 5/1994 | Brauker et al. |
| 5,316,008 A | 5/1994 | Suga et al. |
| 5,322,063 A | 6/1994 | Allen et al. |
| 5,324,322 A | 6/1994 | Grill et al. |
| 5,330,634 A | 7/1994 | Wong et al. |
| 5,331,555 A | 7/1994 | Hashimoto et al. |
| 5,337,747 A | 8/1994 | Neftel |
| 5,343,869 A | 9/1994 | Pross et al. |
| 5,352,351 A | 10/1994 | White |
| 5,354,449 A | 10/1994 | Band et al. |
| 5,376,070 A | 12/1994 | Purvis et al. |
| 5,390,671 A | 2/1995 | Lord et al. |
| 5,391,250 A | 2/1995 | Cheney, II et al. |
| 5,411,647 A | 5/1995 | Johnson et al. |
| 5,411,866 A | 5/1995 | Luong |
| 5,429,735 A | 7/1995 | Johnson et al. |
| 5,448,992 A | 9/1995 | Kupershmidt |
| 5,462,051 A | 10/1995 | Oka et al. |
| 5,466,356 A | 11/1995 | Schneider et al. |
| 5,469,846 A | 11/1995 | Khan |
| 5,474,552 A | 12/1995 | Palti |
| 5,476,776 A | 12/1995 | Wilkins |
| 5,482,008 A | 1/1996 | Stafford et al. |
| 5,482,473 A | 1/1996 | Lord et al. |
| 5,484,404 A | 1/1996 | Schulman et al. |
| 5,494,562 A | 2/1996 | Maley et al. |
| 5,497,772 A | 3/1996 | Schulman et al. |
| 5,502,396 A | 3/1996 | Desarzens et al. |
| 5,507,288 A | 4/1996 | Bocker et al. |
| 5,513,636 A | 5/1996 | Palti |
| 5,518,601 A | 5/1996 | Foos et al. |
| 5,527,288 A | 6/1996 | Gross |
| 5,531,679 A | 7/1996 | Schulman et al. |
| 5,531,878 A | 7/1996 | Vadgama et al. |
| 5,568,806 A | 10/1996 | Cheney, II et al. |
| 5,569,186 A | 10/1996 | Lord et al. |
| 5,575,293 A | 11/1996 | Miller et al. |
| 5,582,184 A | 12/1996 | Ericson et al. |
| 5,584,813 A | 12/1996 | Livingston et al. |
| 5,586,553 A | 12/1996 | Halili et al. |
| 5,589,133 A | 12/1996 | Suzuki |
| 5,611,900 A | 3/1997 | Worden |
| 5,660,163 A | 8/1997 | Schulman et al. |
| 5,665,065 A * | 9/1997 | Colman et al. .................. 604/66 |
| 5,674,289 A | 10/1997 | Fournier et al. |
| 5,676,820 A | 10/1997 | Wang et al. |
| 5,682,884 A | 11/1997 | Hill |
| 5,695,623 A | 12/1997 | Michel et al. |
| 5,696,314 A | 12/1997 | McCaffrey et al. |
| 5,711,861 A | 1/1998 | Ward et al. |
| 5,743,262 A | 4/1998 | Lepper, Jr. et al. |
| 5,749,832 A | 5/1998 | Vadgama et al. |
| 5,749,907 A | 5/1998 | Mann |
| 5,781,455 A | 7/1998 | Hyodo et al. |
| 5,791,344 A | 8/1998 | Schulman et al. |
| 5,800,420 A | 9/1998 | Gross |
| 5,806,517 A | 9/1998 | Gerhardt et al. |
| 5,807,375 A | 9/1998 | Gross et al. |
| 5,814,599 A | 9/1998 | Mitragotri et al. |
| 5,820,622 A | 10/1998 | Gross et al. |
| 5,822,715 A | 10/1998 | Worthington et al. |
| 5,836,989 A | 11/1998 | Shelton |
| 5,840,148 A | 11/1998 | Campbell et al. |
| 5,848,991 A | 12/1998 | Gross |
| 5,882,494 A | 3/1999 | Van Antwerp |
| 5,895,235 A | 4/1999 | Droz |
| 5,904,708 A | 5/1999 | Goedeke |
| 5,919,216 A | 7/1999 | Houben et al. |
| 5,925,021 A | 7/1999 | Castellano et al. |
| 5,931,814 A | 8/1999 | Alex et al. |
| 5,933,136 A | 8/1999 | Brown |
| 5,954,643 A | 9/1999 | Van Antwerp et al. |
| 5,954,954 A | 9/1999 | Houck et al. |
| 5,957,854 A | 9/1999 | Besson et al. |

(56) References Cited

U.S. PATENT DOCUMENTS

| | | | |
|---|---|---|---|
| 5,961,451 A | 10/1999 | Reber et al. | |
| 5,963,132 A | 10/1999 | Yoakum | |
| 5,964,993 A | 10/1999 | Blubaugh et al. | |
| 5,971,922 A | 10/1999 | Arita et al. | |
| 5,995,860 A | 11/1999 | Sun et al. | |
| 5,997,501 A | 12/1999 | Gross | |
| 6,001,067 A | 12/1999 | Shults et al. | |
| 6,011,984 A | 1/2000 | Van Antwerp et al. | |
| 6,027,445 A | 2/2000 | Von Bahr | |
| 6,036,924 A | 3/2000 | Simons et al. | |
| 6,059,946 A | 5/2000 | Yukawa et al. | |
| 6,081,736 A | 6/2000 | Colvin et al. | |
| 6,083,523 A | 7/2000 | Dionne et al. | |
| 6,091,975 A | 7/2000 | Daddona et al. | |
| 6,093,172 A | 7/2000 | Funderburk et al. | |
| 6,117,290 A | 9/2000 | Say | |
| 6,122,536 A | 9/2000 | Sun et al. | |
| 6,123,827 A | 9/2000 | Wong et al. | |
| 6,129,891 A * | 10/2000 | Rolander et al. | 419/16 |
| 6,135,978 A | 10/2000 | Houben et al. | |
| 6,163,720 A | 12/2000 | Gyory et al. | |
| 6,169,155 B1 | 1/2001 | Alvarez et al. | |
| 6,175,752 B1 * | 1/2001 | Say et al. | 600/345 |
| 6,180,416 B1 | 1/2001 | Kurnik et al. | |
| 6,192,891 B1 | 2/2001 | Gravel et al. | |
| 6,208,894 B1 | 3/2001 | Schulman et al. | |
| 6,233,471 B1 | 5/2001 | Berner et al. | |
| 6,248,067 B1 | 6/2001 | Causey, III et al. | |
| 6,272,364 B1 | 8/2001 | Kurnik | |
| 6,272,480 B1 | 8/2001 | Tresp et al. | |
| 6,275,717 B1 | 8/2001 | Gross et al. | |
| 6,284,478 B1 | 9/2001 | Heller et al. | |
| 6,299,583 B1 | 10/2001 | Eggers et al. | |
| 6,302,855 B1 | 10/2001 | Lav et al. | |
| 6,312,388 B1 | 11/2001 | Marcovecchio et al. | |
| 6,326,160 B1 | 12/2001 | Dunn et al. | |
| 6,379,317 B1 | 4/2002 | Kintzig et al. | |
| 6,406,066 B1 | 6/2002 | Uegane | |
| 6,416,651 B1 | 7/2002 | Miller | |
| 6,424,847 B1 | 7/2002 | Mastrototaro et al. | |
| 6,464,849 B1 | 10/2002 | Say et al. | |
| 6,475,750 B1 | 11/2002 | Han et al. | |
| 6,477,395 B2 | 11/2002 | Schulman et al. | |
| 6,510,329 B2 | 1/2003 | Heckel | |
| 6,512,939 B1 | 1/2003 | Colvin et al. | |
| 6,534,711 B1 | 3/2003 | Pollack | |
| 6,544,212 B2 | 4/2003 | Galley et al. | |
| 6,546,269 B1 | 4/2003 | Kurnik | |
| 6,549,796 B2 | 4/2003 | Sohrab | |
| 6,553,241 B2 | 4/2003 | Mannheimer et al. | |
| 6,553,244 B2 | 4/2003 | Lesho et al. | |
| 6,558,320 B1 | 5/2003 | Causey | |
| 6,558,321 B1 | 5/2003 | Burd et al. | |
| 6,558,351 B1 | 5/2003 | Steil et al. | |
| 6,558,955 B1 | 5/2003 | Kristal et al. | |
| 6,560,471 B1 | 5/2003 | Heller et al. | |
| 6,561,978 B1 | 5/2003 | Conn et al. | |
| 6,562,001 B2 | 5/2003 | Lebel et al. | |
| 6,565,509 B1 | 5/2003 | Say et al. | |
| 6,571,128 B2 | 5/2003 | Lebel et al. | |
| 6,572,545 B2 | 6/2003 | Knobbe et al. | |
| 6,575,905 B2 | 6/2003 | Knobbe et al. | |
| 6,577,899 B2 | 6/2003 | Lebel et al. | |
| 6,589,229 B1 | 7/2003 | Connelly et al. | |
| 6,591,125 B1 | 7/2003 | Buse et al. | |
| 6,605,072 B2 | 8/2003 | Struys et al. | |
| 6,612,984 B1 | 9/2003 | Kerr | |
| 6,613,379 B2 | 9/2003 | Ward et al. | |
| 6,618,934 B1 | 9/2003 | Feldman et al. | |
| 6,620,138 B1 | 9/2003 | Marrgi et al. | |
| 6,633,772 B2 | 10/2003 | Ford et al. | |
| 6,635,014 B2 | 10/2003 | Starkweather et al. | |
| 6,641,533 B2 | 11/2003 | Causey et al. | |
| 6,648,821 B2 | 11/2003 | Lebel et al. | |
| 6,654,625 B1 | 11/2003 | Say et al. | |
| 6,673,022 B1 | 1/2004 | Bobo et al. | |
| 6,673,596 B1 | 1/2004 | Sayler et al. | |
| 6,694,191 B2 | 2/2004 | Starkweather et al. | |
| 6,699,383 B2 | 3/2004 | Lemire et al. | |
| 6,702,972 B1 | 3/2004 | Markle | |
| 6,721,587 B2 | 4/2004 | Gough | |
| 6,731,976 B2 | 5/2004 | Penn et al. | |
| 6,740,072 B2 | 5/2004 | Starkweather et al. | |
| 6,740,075 B2 | 5/2004 | Lebel et al. | |
| 6,742,635 B2 | 6/2004 | Neel et al. | |
| 6,743,635 B2 | 6/2004 | Neel et al. | |
| 6,750,055 B1 | 6/2004 | Connelly et al. | |
| 6,773,565 B2 | 8/2004 | Kunimoto et al. | |
| 6,802,957 B2 | 10/2004 | Jung et al. | |
| 6,809,653 B1 | 10/2004 | Mann et al. | |
| 6,810,290 B2 | 10/2004 | Lebel et al. | |
| 6,813,519 B2 | 11/2004 | Lebel et al. | |
| 6,832,200 B2 | 12/2004 | Greeven et al. | |
| 6,862,465 B2 | 3/2005 | Shults et al. | |
| 6,875,195 B2 | 4/2005 | Choi | |
| 6,893,552 B1 | 5/2005 | Wang et al. | |
| 6,895,263 B2 | 5/2005 | Shin et al. | |
| 6,931,327 B2 | 8/2005 | Goode et al. | |
| 6,936,006 B2 | 8/2005 | Sabra | |
| 6,936,029 B2 | 8/2005 | Mann et al. | |
| 6,965,791 B1 | 11/2005 | Hitchcock et al. | |
| 6,998,247 B2 | 2/2006 | Monfre et al. | |
| 7,011,630 B2 | 3/2006 | Desai et al. | |
| 7,025,743 B2 | 4/2006 | Mann et al. | |
| 7,029,444 B2 | 4/2006 | Shin et al. | |
| 7,058,437 B2 | 6/2006 | Buse et al. | |
| 7,060,059 B2 | 6/2006 | Keith et al. | |
| 7,074,307 B2 | 7/2006 | Simpson et al. | |
| 7,081,195 B2 | 7/2006 | Simpson et al. | |
| 7,098,803 B2 | 8/2006 | Mann et al. | |
| 7,134,999 B2 | 11/2006 | Brauker et al. | |
| 7,162,290 B1 | 1/2007 | Levin | |
| 7,225,535 B2 | 6/2007 | Feldman et al. | |
| 7,267,665 B2 | 9/2007 | Steil et al. | |
| 7,276,029 B2 | 10/2007 | Goode et al. | |
| 7,278,983 B2 | 10/2007 | Ireland et al. | |
| 7,282,029 B1 | 10/2007 | Poulsen et al. | |
| 7,291,114 B2 | 11/2007 | Mault | |
| 7,295,867 B2 | 11/2007 | Berner et al. | |
| 7,344,500 B2 | 3/2008 | Talbot et al. | |
| 7,367,942 B2 | 5/2008 | Grage et al. | |
| 7,417,164 B2 | 8/2008 | Suri | |
| 7,519,408 B2 | 4/2009 | Rasdal et al. | |
| 7,569,030 B2 | 8/2009 | Lebel et al. | |
| 7,591,801 B2 | 9/2009 | Brauker et al. | |
| 7,640,048 B2 | 12/2009 | Dobbles et al. | |
| 7,647,237 B2 | 1/2010 | Malave et al. | |
| 7,657,297 B2 | 2/2010 | Simpson et al. | |
| 7,901,394 B2 | 3/2011 | Ireland et al. | |
| 7,946,985 B2 | 5/2011 | Mastrototaro et al. | |
| 8,512,276 B2 | 8/2013 | Talbot et al. | |
| 2001/0007950 A1 | 7/2001 | North et al. | |
| 2001/0016682 A1 | 8/2001 | Berner et al. | |
| 2001/0041830 A1 | 11/2001 | Varalli et al. | |
| 2002/0026111 A1 | 2/2002 | Ackerman | |
| 2002/0042561 A1 | 4/2002 | Schulman et al. | |
| 2002/0043471 A1 | 4/2002 | Ikeda et al. | |
| 2002/0084196 A1 | 7/2002 | Liamos et al. | |
| 2002/0099997 A1 | 7/2002 | Piret | |
| 2002/0119711 A1 | 8/2002 | Van Antwerp et al. | |
| 2002/0123048 A1 | 9/2002 | Gau | |
| 2002/0161288 A1 | 10/2002 | Shin et al. | |
| 2002/0188185 A1 | 12/2002 | Sohrab | |
| 2003/0023171 A1 | 1/2003 | Sato et al. | |
| 2003/0028089 A1 | 2/2003 | Galley et al. | |
| 2003/0060753 A1 | 3/2003 | Starkweather et al. | |
| 2003/0060765 A1 | 3/2003 | Campbell et al. | |
| 2003/0078481 A1 | 4/2003 | McIvor et al. | |
| 2003/0097082 A1 | 5/2003 | Purdy et al. | |
| 2003/0114836 A1 | 6/2003 | Estes et al. | |
| 2003/0119208 A1 | 6/2003 | Yoon et al. | |
| 2003/0130616 A1 | 7/2003 | Steil et al. | |
| 2003/0134347 A1 | 7/2003 | Heller et al. | |
| 2003/0176183 A1 | 9/2003 | Drucker et al. | |

(56) References Cited

U.S. PATENT DOCUMENTS

| | | |
|---|---|---|
| 2003/0187338 A1 | 10/2003 | Say et al. |
| 2003/0188427 A1 | 10/2003 | Say et al. |
| 2003/0208113 A1 | 11/2003 | Mault et al. |
| 2003/0211625 A1 | 11/2003 | Cohan |
| 2003/0212346 A1 | 11/2003 | Yuzhakov et al. |
| 2003/0212347 A1 | 11/2003 | Sohrab |
| 2003/0235817 A1 | 12/2003 | Bartkowiak et al. |
| 2004/0011671 A1 | 1/2004 | Shults et al. |
| 2004/0015134 A1 | 1/2004 | Lavi et al. |
| 2004/0068230 A1 | 4/2004 | Estes et al. |
| 2004/0074785 A1 | 4/2004 | Holker |
| 2004/0078219 A1 | 4/2004 | Kaylor |
| 2004/0122297 A1 | 6/2004 | Stahmann et al. |
| 2004/0152187 A1 | 8/2004 | Haight et al. |
| 2004/0162678 A1 | 8/2004 | Hetzel et al. |
| 2004/0167801 A1 | 8/2004 | Say et al. |
| 2004/0173472 A1 | 9/2004 | Jung et al. |
| 2004/0186365 A1 | 9/2004 | Jin et al. |
| 2004/0204687 A1 | 10/2004 | Morgensen |
| 2004/0254433 A1 | 12/2004 | Bandis |
| 2005/0027180 A1 | 2/2005 | Goode et al. |
| 2005/0027182 A1 | 2/2005 | Siddiqui et al. |
| 2005/0027463 A1 | 2/2005 | Goode et al. |
| 2005/0031689 A1 | 2/2005 | Shults et al. |
| 2005/0033132 A1 | 2/2005 | Shults et al. |
| 2005/0043598 A1 | 2/2005 | Goode et al. |
| 2005/0051427 A1 | 3/2005 | Brauker et al. |
| 2005/0051440 A1 | 3/2005 | Simpson et al. |
| 2005/0054909 A1 | 3/2005 | Petisce et al. |
| 2005/0056552 A1 | 3/2005 | Simpson et al. |
| 2005/0090607 A1 | 4/2005 | Tapsak et al. |
| 2005/0112169 A1 | 5/2005 | Brauker et al. |
| 2005/0113653 A1 | 5/2005 | Fox et al. |
| 2005/0113744 A1 | 5/2005 | Donoghue et al. |
| 2005/0121322 A1 | 6/2005 | Say |
| 2005/0143635 A1 | 6/2005 | Kamath et al. |
| 2005/0143675 A1 | 6/2005 | Neel et al. |
| 2005/0154271 A1 | 7/2005 | Rasdal et al. |
| 2005/0177398 A1 | 8/2005 | Watanabe et al. |
| 2005/0182451 A1 | 8/2005 | Griffin et al. |
| 2005/0187720 A1 | 8/2005 | Goode et al. |
| 2005/0192557 A1* | 9/2005 | Brauker et al. ............ 604/503 |
| 2005/0203360 A1 | 9/2005 | Brauker et al. |
| 2005/0239154 A1 | 10/2005 | Feldman et al. |
| 2005/0242479 A1 | 11/2005 | Petisce et al. |
| 2005/0245795 A1 | 11/2005 | Goode et al. |
| 2005/0245799 A1 | 11/2005 | Brauker et al. |
| 2005/0245904 A1 | 11/2005 | Estes et al. |
| 2005/0261563 A1 | 11/2005 | Zhou et al. |
| 2006/0015020 A1 | 1/2006 | Neale et al. |
| 2006/0015024 A1 | 1/2006 | Brister et al. |
| 2006/0020186 A1 | 1/2006 | Brister et al. |
| 2006/0036141 A1 | 2/2006 | Kamath et al. |
| 2006/0036143 A1 | 2/2006 | Brister et al. |
| 2006/0036144 A1 | 2/2006 | Brister et al. |
| 2006/0040402 A1 | 2/2006 | Brauker et al. |
| 2006/0079809 A1 | 4/2006 | Goldberger et al. |
| 2006/0173406 A1 | 8/2006 | Hayes et al. |
| 2006/0183984 A1 | 8/2006 | Dobbles et al. |
| 2006/0183985 A1 | 8/2006 | Brister et al. |
| 2006/0195029 A1 | 8/2006 | Shults et al. |
| 2006/0222566 A1 | 10/2006 | Brauker et al. |
| 2006/0258929 A1 | 11/2006 | Goode et al. |
| 2007/0016381 A1 | 1/2007 | Kamath et al. |
| 2007/0027385 A1 | 2/2007 | Brister et al. |
| 2007/0032706 A1 | 2/2007 | Kamath et al. |
| 2007/0038044 A1 | 2/2007 | Dobbles et al. |
| 2007/0066873 A1 | 3/2007 | Kamath et al. |
| 2007/0066956 A1 | 3/2007 | Finkel |
| 2007/0100222 A1 | 5/2007 | Mastrototaro et al. |
| 2007/0106135 A1 | 5/2007 | Sloan et al. |
| 2007/0112298 A1 | 5/2007 | Mueller et al. |
| 2007/0173761 A1 | 7/2007 | Kanderian et al. |
| 2007/0179434 A1 | 8/2007 | Weinert et al. |
| 2007/0203410 A1 | 8/2007 | Say et al. |
| 2007/0203966 A1 | 8/2007 | Brauker et al. |
| 2007/0208244 A1 | 9/2007 | Brauker et al. |
| 2007/0208245 A1 | 9/2007 | Brauker et al. |
| 2007/0208246 A1 | 9/2007 | Brauker et al. |
| 2007/0235331 A1 | 10/2007 | Simpson et al. |
| 2008/0021666 A1 | 1/2008 | Goode et al. |
| 2008/0097289 A1 | 4/2008 | Steil et al. |
| 2008/0187655 A1 | 8/2008 | Markle et al. |
| 2008/0188722 A1 | 8/2008 | Markle et al. |
| 2008/0188725 A1 | 8/2008 | Markle et al. |
| 2008/0188731 A1 | 8/2008 | Brister et al. |
| 2008/0194935 A1 | 8/2008 | Brister et al. |
| 2008/0208025 A1 | 8/2008 | Shults et al. |
| 2008/0210557 A1 | 9/2008 | Heller et al. |
| 2008/0214915 A1 | 9/2008 | Brister et al. |
| 2008/0262469 A1 | 10/2008 | Brister et al. |
| 2008/0269723 A1 | 10/2008 | Mastrototaro et al. |
| 2008/0287764 A1 | 11/2008 | Rasdal et al. |
| 2008/0287765 A1 | 11/2008 | Rasdal et al. |
| 2008/0287766 A1 | 11/2008 | Rasdal et al. |
| 2008/0296155 A1 | 12/2008 | Shults et al. |
| 2008/0305009 A1 | 12/2008 | Gamsey et al. |
| 2008/0305506 A1 | 12/2008 | Suri |
| 2008/0306433 A1 | 12/2008 | Dobbles et al. |
| 2008/0306435 A1 | 12/2008 | Kamath et al. |
| 2008/0306444 A1 | 12/2008 | Brister et al. |
| 2009/0018418 A1 | 1/2009 | Markle et al. |
| 2009/0018426 A1 | 1/2009 | Markle et al. |
| 2009/0061528 A1 | 3/2009 | Suri |
| 2009/0076356 A1 | 3/2009 | Simpson |
| 2009/0076360 A1 | 3/2009 | Brister et al. |
| 2009/0081803 A1 | 3/2009 | Gamsey et al. |
| 2009/0099434 A1 | 4/2009 | Liu et al. |
| 2009/0156924 A1 | 6/2009 | Shariati et al. |
| 2009/0177143 A1 | 7/2009 | Markle et al. |
| 2009/0192366 A1 | 7/2009 | Mensinger et al. |
| 2009/0192722 A1 | 7/2009 | Shariati et al. |
| 2009/0192751 A1 | 7/2009 | Kamath et al. |
| 2009/0216103 A1 | 8/2009 | Brister et al. |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0242399 A1 | 10/2009 | Kamath et al. |
| 2009/0242425 A1 | 10/2009 | Kamath et al. |
| 2009/0264719 A1 | 10/2009 | Markle et al. |
| 2009/0264856 A1 | 10/2009 | Lebel et al. |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2009/0299276 A1 | 12/2009 | Brauker et al. |
| 2010/0010324 A1 | 1/2010 | Brauker et al. |
| 2010/0010331 A1 | 1/2010 | Brauker et al. |
| 2010/0010332 A1 | 1/2010 | Brauker et al. |
| 2010/0016687 A1 | 1/2010 | Brauker et al. |
| 2010/0022855 A1 | 1/2010 | Brauker et al. |
| 2010/0030053 A1 | 2/2010 | Goode, Jr. et al. |
| 2010/0030484 A1 | 2/2010 | Brauker et al. |
| 2010/0036215 A1 | 2/2010 | Goode, Jr. et al. |
| 2010/0036216 A1 | 2/2010 | Goode, Jr. et al. |
| 2010/0036222 A1 | 2/2010 | Goode, Jr. et al. |
| 2010/0036223 A1 | 2/2010 | Goode, Jr. et al. |
| 2010/0036224 A1 | 2/2010 | Goode, Jr. et al. |
| 2010/0036225 A1 | 2/2010 | Goode, Jr. et al. |
| 2010/0041971 A1 | 2/2010 | Goode, Jr. et al. |
| 2010/0045465 A1 | 2/2010 | Brauker et al. |
| 2010/0049024 A1 | 2/2010 | Saint et al. |
| 2010/0076283 A1 | 3/2010 | Simpson et al. |
| 2011/0270158 A1 | 11/2011 | Brauker et al. |
| 2012/0059673 A1 | 3/2012 | Cohen et al. |
| 2012/0186581 A1 | 7/2012 | Brauker et al. |
| 2012/0190953 A1 | 7/2012 | Brauker et al. |
| 2012/0191063 A1 | 7/2012 | Brauker et al. |
| 2012/0215201 A1 | 8/2012 | Brauker et al. |
| 2012/0220979 A1 | 8/2012 | Brauker et al. |
| 2012/0227737 A1 | 9/2012 | Mastrototaro et al. |
| 2012/0238852 A1 | 9/2012 | Brauker et al. |

(56) References Cited

U.S. PATENT DOCUMENTS

| | | | |
|---|---|---|---|
| 2012/0259278 | A1 | 10/2012 | Hayes et al. |
| 2012/0296311 | A1 | 11/2012 | Brauker et al. |

FOREIGN PATENT DOCUMENTS

| | | | |
|---|---|---|---|
| EP | 0 127 958 | | 12/1984 |
| EP | 0 286 118 | | 10/1988 |
| EP | 0 320 109 | | 6/1989 |
| EP | 0 353 328 | | 2/1990 |
| EP | 0 390 390 | | 10/1990 |
| EP | 0 396 788 | | 11/1990 |
| EP | 0 441 394 | | 8/1991 |
| EP | 0 534 074 | | 3/1993 |
| EP | 0 563 795 | | 10/1993 |
| EP | 0 838 230 | | 4/1998 |
| EP | 0 880 936 | | 12/1998 |
| EP | 0 967 788 | | 12/1999 |
| EP | 1 078 258 | | 2/2001 |
| EP | 1 102 194 | A2 | 5/2001 |
| EP | 1 266 607 | | 12/2002 |
| EP | 1 338 295 | A1 | 8/2003 |
| EP | 1 498 067 | | 1/2005 |
| EP | 2 226 086 | | 8/2010 |
| EP | 2 228 642 | | 9/2010 |
| FR | 2656423 | | 6/1991 |
| FR | 2760962 | | 9/1998 |
| GB | 2149918 | | 6/1985 |
| JP | 62083649 | | 4/1987 |
| JP | 07-083871 | | 3/1995 |
| JP | 2002-189015 | | 7/2002 |
| WO | WO 89/02720 | | 4/1989 |
| WO | WO 90/00738 | | 1/1990 |
| WO | WO 90/10861 | | 9/1990 |
| WO | WO 92/13271 | | 8/1992 |
| WO | WO 93/14693 | | 8/1993 |
| WO | WO 95/07109 | | 3/1995 |
| WO | WO 95/13838 | | 5/1995 |
| WO | WO 96/14026 | | 5/1996 |
| WO | WO 96/25089 | | 8/1996 |
| WO | WO 97/01986 | | 1/1997 |
| WO | WO 97/06727 | | 2/1997 |
| WO | WO 97/28737 | | 8/1997 |
| WO | WO 98/24358 | | 6/1998 |
| WO | WO 99/56613 | | 4/1999 |
| WO | WO 99/48419 | | 9/1999 |
| WO | WO 99/58973 | | 11/1999 |
| WO | WO 99/59657 | | 11/1999 |
| WO | WO 00/19887 | | 4/2000 |
| WO | WO 00/32098 | | 6/2000 |
| WO | WO 00/33065 | | 6/2000 |
| WO | WO 00/49941 | | 8/2000 |
| WO | WO 00/59373 | | 10/2000 |
| WO | WO 00/74753 | | 12/2000 |
| WO | WO 00/78210 | | 12/2000 |
| WO | WO 01/12158 | | 2/2001 |
| WO | WO 01/20019 | | 3/2001 |
| WO | WO 01/52727 | A1 | 7/2001 |
| WO | WO 01/88534 | A2 | 11/2001 |
| WO | WO 02/24065 | A1 | 3/2002 |
| WO | WO 03/022327 | | 3/2003 |
| WO | WO 2004/009161 | | 1/2004 |
| WO | WO 2005/011489 | | 2/2005 |
| WO | 2005-0026689 | | 3/2005 |
| WO | WO 2005/026689 | | 10/2005 |
| WO | WO 2005-093629 | | 10/2005 |
| WO | WO 2006/017358 | | 2/2006 |
| WO | WO 2006/021430 | | 3/2006 |

OTHER PUBLICATIONS

Abe et al. 1992. Characterization of glucose microsensors for intracellular measurements. Alan. Chem. 64(18):2160-2163.
Abel et al. 1984. Experience with an implantable glucose sensor as a prerequisite of an artifical beta cell, Biomed. Biochim. Acta 43(5):577-584.
Alcock & Turner. 1994. Continuous Analyte Monitoring to Aid Clinical Practice. IEEE Engineering in Med. & Biol. Mag. 13:319-325.
American Heritage Dictionary, 4th Edition. 2000. Houghton Mifflin Company, p. 82.
Amin et al. 2003. Hypoglycemia prevalence in prepubertal children with type 1 diabetes on standard insulin regimen: Use of continuous glucose monitoring system. Diabetes Care 26(3):662-667.
Answers.com. "xenogenic." The American Heritage Stedman's Medical Dictionary. Houghton Mifflin Company, 2002. Answers. com Nov. 7, 2006 http://www.Answers.com/topic/xenogenic.
Atanasov et al. 1994. Biosensor for continuous glucose monitoring. Biotechnology and Bioengineering 43:262-266.
Atanasov et al. 1997. Implantation of a refillable glucose monitoring-telemetry device. Biosens Bioelectron 12:669-680.
Bailey et al. 2007. Reduction in hemoglobin A1c with real-time continuous glucose monitoring: results from a 12-week observational study. Diabetes Technology & Therapeutics 9(3):203-210.
Beach et al. 1999. Subminiature implantable potentiostat and modified commercial telemetry device for remote glucose monitoring. IEEE Transactions on Instrumentation and Measurement 48(6):1239-1245.
Bessman et al., Progress toward a glucose sensor for the artificial pancreas, Proceedings of a Workshop on Ion-Selective Microelectrodes, Jun. 4-5, 1973, Boston, MA, 189-197.
Biermann et al. 2008. How would patients behave if they were continually informed of their blood glucose levels? A simulation study using a "virtual" patient. Diab. Thechnol. & Therapeut., 10:178-187.
Bisenberger et al. 1995. A triple-step potential waveform at enzyme multisensors with thick-film gold electrodes for detection of glucose and sucrose. Sensors and Actuators, B 28:181-189.
Boedeker Plastics, Inc. 2009. Polyethylene Specifications Data Sheet, http://www.boedeker.com/polye_p.htm [Aug. 19, 2009 3:36:33 PM].
Boland et al. 2001. Limitations of conventional methods of self-monitoring of blood glucose. Diabetes Care 24(11):1858-1862.
Bowman, L.; Meindl, J. D. 1986. The packaging of implantable integrated sensors. IEEE Trans Biomed Eng BME33(2):248-255.
Brauker et al. Jun. 27, 1996. Local Inflammatory Response Around Diffusion Chambers Containing Xenografts Transplantation 61(12):1671-1677.
Braunwald, 2008. Biomarkers in heart failure. *N. Engl. J. Med.*, 358: 2148-2159.
Bremer et al. 2001. Benchmark data from the literature for evaluation of new glucose sensing technologies. Diabetes Technology & Therapeutics 3(3):409-418.
Bruckel et al. 1989. In vivo measurement of subcutaneous glucose concentrations with an enzymatic glucose sensor and a wick method. Klin Wochenschr 67:491-495.
Cai et al. 2004. A wireless, remote query glucose biosensor based on a pH-sensitive polymer. Anal Chem 76(4):4038-4043.
Campanella et al. 1993. Biosensor for direct determination of glucose and lactate in undiluted biological fluids. Biosensors & Bioelectronics 8:307-314.
Cassidy et al., Apr. 1993. Novel electrochemical device for the detection of cholesterol or glucose, Analyst, 118:415-418.
Chase et al. 2001. Continuous subcutaneous glucose monitoring in children with type 1 diabetes. Pediatrics 107:222-226.
Ciba® Irgacure 2959 Photoinitiator Product Description, Ciba Specialty Chemicals Inc., Basel, Switzerland.
Claremont et al. 1986. Subcutaneous implantation of a ferrocene-mediated glucose sensor in pigs. Diabetologia 29:817-821.
Claremont et al. Jul. 1986. Potentially-impintable, ferrocene-mediated glucose sensor. J. Biomed. Eng. 8:272-274.
Clark et al., 1981. One-minute electrochemical enzymic assay for cholesterol in biological materials, Clin. Chem. 27(12):1978-1982.
Clark et al. 1987. Configurational cyclic voltammetry: increasing the specificity and reliablity of implanted electrodes, IEEE/Ninth Annual Conference of the Engineering in Medicine and Biology Society, pp. 0782-0783.
Clark et al. 1988. Long-term stability of electroenzymatic glucose sensors implanted in mice. Trans Am Soc Artif Intern Organs 34:259-265.

(56) References Cited

OTHER PUBLICATIONS

CLSI. Performance metrics for continuous interstitial glucose monitoring; approved guideline, CLSI document POCT05-A. Wayne, PA: Clinical and Laboratory Standards Institute: 2008 28(33), 72 pp.

Colangelo et al. 1967. Corrosion rate measurements in vivo, Journal of Biomedical Materials Research, 1:405-414.

Colowick et al. 1976. Methods in Enzymlology, vol. XLIV, Immobilized Enzymes. New York: Academic Press.

Cox et al. 1985. Accuracy of perceiving blood glucose in IDDM. Diabetes Care 8(6):529-536.

Csoregi et al., 1994. Design, characterization, and one-point in vivo calibration of a subcutaneously implanted glucose electrode. Anal Chem. 66(19):3131-3138.

Danielsson et al. 1988. Enzyme thermistors, Methods in Enzymology, 137:181-197.

Dassau et al., In silico evaluation platform for artifical pancreatic β-cell development—a dynamic simulator for closed loop control with hardware-in-the-loop, Diabetes Technology & Therapeutics, 11(3):1-8, 2009.

Davis et al. 1983. Bioelectrochemical fuel cell and sensor based on a quinoprotein, alcohol dehydrogenase. *Enzyme Microb. Technol.*, vol. 5, September 383-388.

Direct 30/30® meter (Markwell Medical) (Catalog).

Dixon et al. 2002. Characterization in vitro and in vivo of the oxygen dependence of an enzyme/polymer biosensor for monitoring brain glucose. Journal of Neuroscience Methods 119:135-142.

DuPont[1] Dimension AR® (Catalog), 1998.

Durliat et al. 1976. Spectrophotometric and electrochemical determinations of L(+)-lactate in blood by use of lactate dehydrogenase from yeast, Clin. Chem. 22(11):1802-1805.

Edwards Lifesciences. Accuracy for your and your patients. Marketing materials, 4 pp. 2002.

El Degheidy et al. 1986. Optimization of an implantable coated wire glucose sensor. J. Biomed Eng. 8: 121-129.

El-Khatib et al. 2007. Adaptive closed-loop control provides blood-glucose regulation using dual subcutaneous insulin and glucagon infusion in diabetic swine, Journal of Diabetes Science and Technology, 1(2):181-192.

Ei-Sa'ad et al. 1990. Moisture Absorption by Epoxy Resins: the Reverse Thermal Effect. Journal of Materials Science 25:3577-3582.

Ernst et al. 2002. Reliable glucose monitoring through the use of microsystem technology. Anal. Bioanal. Chem. 373:758-761.

Fabietti et al. 2007. Clinical validation of a new control-oriented model of insulin and glucose dynamcs in subjects with type 1 diabetes, Diabetes Technology & Therapeutics, 9(4):327-338.

Fahy et al., An analysis: hyperglycemic intensive care patients need continuous glocuse monitoring—easier said than done, Journal of Diabetese Science and Technology, 2(2):201-204, Mar. 2008.

Fare et al. 1998. Functional characterization of a conducting polymer-based immunoassay system. Biosensors & Bioelectronics 13(3-4):459-470.

Feldman et al. 2003. A continuous glucose sensor based on wired enzyme technology—results from a 3-day trial in patients with type 1 diabetes. Diabetes Technol Ther 5(5):769-779.

Fischer et al. 1987. Assessment of subcutaneous glucose concentration: validation of the wick technique as a reference for implanted electrochemical sensors in normal and diabetic dogs, Diabetologia 30:940-945.

Fischer et al. 1989. Oxygen Tension at the Subcutaneous Implantation Site of Glucose Sensors. Biomed. Biochem 11/12:965-972.

Fischer et al. 1995. Hypoglycaemia—warning by means of subcutaneous electrochemical glucose sensors: an animal study, Horm. Metab. Rese. 27:53.

Freedman et al. 1991. Statistics, Second Edition, W.W. Norton & Company, p. 74.

Frohnauer et al. 2001. Graphical human insulin time-activity profiles using standardized definitions. Diabetes Technology & Therapeutics 3(3):419-429.

Gabbay et al. 2008. Optical coherence tomography-based continuous noninvasive glucose monitoring in patients with diabetes. Diab. Thechnol. & Therapeut., 10:188-193.

Ganesan et al., Gold layer-based dual crosslinking procedure of glucose oxidase with ferrocene monocarboxylic acid provides a stable biosensor, Analytical Biochemistry 343:188-191, 2005.

Ganesh et al., Evaluation of the VIA® blood chemistry monitor for glucose in healthy and diabetic volunteers, Journal of Diabetese Science and Technology, 2(2):182-193, Mar. 2008.

Gerritsen et al. 1999. Performance of subcutaneously implanted glucose sensors for continuous monitoring. The Netherlands Journal of Medicine 54:167-179.

Gerritsen, M. 2000. Problems associated with subcutaneously implanted glucose sensors. Diabetes Care 23(2):143-145.

Gilligan et al. 1994. Evaluation of a subcutaneous glucose sensor out to 3 months in a dog model. Diabetes Care 17(8):882-887.

Godsland et al. 2001. Maximizing the Success Rate of Minimal Model Insulin Sensitivity Measurement in Humans: The Importance of Basal Glucose Levels. The Biochemical Society and the Medical Research Society, 1-9.

Gouda et al., Jul. 4, 2003. Thermal inactiviation of glucose oxidase, The Journal of Biological Chemistry, 278(27):24324-24333.

Gough et al. 2000. Immobilized glucose oxidase in implantable glucose sensor technology. Diabetes Technology & Therapeutics 2(3):377-380.

Gough et al. 2003. Frequency characterization of blood glucose dynamics. Annals of Biomedical Engineering 31:91-97.

Gross et al. 2000. Efficacy and reliability of the continuous glucose monitoring system. Diabetes Technology & Therapeutics, 2(Suppl 1):S19-26.

Gross et al. 2000. Performance evaluation of the MiniMed® continuous glucose monitoring system during patient home use. Diabetes Technology & Therapeutics 2(1):49-56.

Hall et al. 1998. Electrochemical oxidation of hydrogen peroxide at platinum electrodes. Part I: An adsorption-controlled mechanism. Electrochimica Acta, 43(5-6):579-588.

Hall et al. 1998. Electrochemical oxidation of hydrogen peroxide at platinum electrodes. Part II: Effect of potential. Electrochimica Acta 43(14-15):2015-2024.

Hall et al. 1999. Electrochemical oxidation of hydrogen peroxide at platinum electrodes. Part III: Effect of temperature. Electrochimica Acta, 44:2455-2462.

Hall et al. 1999. Electrochemical oxidation of hydrogen peroxide at platinum electrodes. Part IV: Phosphate buffer dependence. Electrochimica Acta, 44:4573-4582.

Hall et al. 2000. Electrochemical oxidation of hydrogen peroxide at platinum electrodes. Part V: Inhibition by chloride. Electrochimica Acta, 45:3573-3579.

Hamilton Syringe Selection Guide. 2006. Syringe Selection. www.hamiltoncompany.com.

Hashiguchi et al. (1994). "Development of a miniaturized glucose monitoring system by combining a needle-type glucose sensor with microdialysis sampling method: Long-term subcutaneous tissue glucose monitoring in ambulatory diabetic patients," *Diabetes C.*

Heller, A. 2003. Plugging metal connectors into enzymes. Nat Biotechnol 21:631-2.

Hitchman, M. L. 1978. Measurement of Dissolved Oxygen. In Elving et al. (Eds.). Chemical Analysis, vol. 49, Chap. 3, pp. 34-49, 59-123. New York: John Wiley & Sons.

Hoel, Paul G. 1976. Elementary Statistics, Fourth Edition. John Wiley & Sons, Inc.. pp. 113-114.

Hrapovic et al. 2003. Picoamperometric detection of glucose at ultrasmall platinum-based biosensors: preparation and characterization. Anal Chem 75:3308-3315.

http://www.merriam-webster.com/dictionary, definition for "aberrant," Aug. 19, 2008, p. 1.

Huang et al. A 0.5mV passive telemetry IC for biomedical applications. Swiss Federal Institute of Technology. 4 pp.

Huang et al. Aug. 1975. Electrochemical Generation of Oxygen. 1: The Effects of Anions and Cations on Hydrogen Chemisorption and Aniodic Oxide Film Formation on Platinum Electrode. 2: The Effects of Anions and Cations on Oxygen Generation on Platinum E.

(56) References Cited

OTHER PUBLICATIONS

Ishikawa et al. 1998. Initial evaluation of a 290-mm diameter subcutaneous glucose sensor: Glucose monitoring with a biocompatible, flexible-wire, enzyme-based amperometric microsensor in diabetic and nondiabetic humans. Journal of Diabetes and Its Compl.
Jensen et al. 1997. Fast wave forms for pulsed electrochemical detection of glucose by incorporation of reductive desorption of oxidation products. Analytical Chemistry 69(9):1776-1781.
Jeutter, D. C. 1982. A transcutaneous implanted battery recharging and biotelemeter power switching system. IEEE Trans Biomed Eng 29:314-321.
Johnson (1991). "Reproducible electrodeposition of biomolecules for the fabrication of miniature electroenzymatic biosensors," *Sensors and Actuators B*, 5:85-89.
Jovanovic, L. 2000. The role of continuous glucose monitoring in gestational diabetes mellitus. Diabetes Technology & Therapeutics, 2 Suppl 1, S67-71.
Kacaniklic May-Jun. 1994. Electroanalysis, 6(5-6):381-390.
Kamath et al. Calibration of a continuous glucose monitor: effect of glucose rate of change, Eighth Annual Diabetes Technology Meeting, Nov. 13-15 2008, p. A88.
Kang et al. 2003. In vitro and short-term in vivo characteristics of a Kel-F thin film modified glucose sensor. Anal Sci 19:1481-1486.
Kaufman. 2000. Role of the continuous glucose monitoring system in pediatric patients. Diabetes Technology & Therapeutics 2(1):S-49-S-52.
Kaufman et al. 2001. A pilot study of the continuous glucose monitoring system. Diabetes Care 24(12):2030-2034.
Keedy et al. 1991. Determination of urate in undiluted whole blood by enzyme electrode. *Biosensors & Bioelectronics*, 6: 491-499.
Kerner et al. 1988. A potentially implantable enzyme electrode for amperometric measurement of glucose, Horm Metab Res Suppl. 20:8-13.
Klueh et al. 2003. Use of Vascular Endothelia Cell Growth Factor Gene Transfer to Enhance Implantable Sensor Function in Vivo, Biosensor Function and Vegf-Gene Transfer, pp. 1072-1086.
Ko, Wen H. 1985. Implantable Sensors for Closed-Loop Prosthetic Systems, Futura Pub. Co., Inc., Mt. Kisco, NY, Chapter 15:197-210.
Kondo et al. 1982. A miniature glucose sensor, implantable in the blood stream. Diabetes Care. 5(3):218-221.
Koschinsky et al. 2001. Sensors for glucose monitoring: Technical and clinical aspects. Diabetes Metab. Res. Rev. 17:113-123.
Kost et al. 1985. Glucose-sensitive membranes containing glucose oxidase: activitiy, swelling, and permeability studies, Journal of Biomedical Materials Research 19:1117-1133.
Koudelka et al. 1989. In vivo response of microfabricated glucose sensors to glycemia changes in normal rats. Biomed Biochim Acta 48(11-12):953-956.
Koudelka et al. 1991. In-vivo behaviour of hypodermically implanted microfabricated glucose sensors. Biosensors & Bioelectronics 6:31-36.
Kraver et al. 2001. A mixed-signal sensor interface microinstrument. Sensors and Actuators A 91:266-277.
Kruger et al. 2000. Psychological motivation and patient education: A role for continuous glucose monitoring. Diabetes Technology & Therapeutics, 2(Suppl 1):S93-97.
Kulys et al., 1994. Carbon-paste biosensors array for long-term glucose measurement, Biosensors& Beioelectronics, 9:491-500.
Kunjan et al., Automated blood sampling and glocuse sensing in critical care settings, Journal of Diabetes Science and Technology 2(3):194-200, Mar. 2008.
Kurtz et al. 2005. Recommendations for blood pressure measurement in humans and experimental animals, Part 2: Blood pressure measurement in experimental animals, A statement for professionals from the subcommittee of professional and public education of.
Ladd et al., Structure Determination by X-ray Crystallography, 3rd ed. Plenum, 1996, Ch. 1, pp. xxi-xxiv and 1-58.
Lewandowski et al. 1988. Evaluation of a miniature blood glucose sensor. Trans Am Soc Artif Intern Organs 34:255-258.

Leypoldt et al. 1984. Model of a two-substrate enzyme electrode for glucose. Anal. Chem. 56:2896-2904.
Linke et al. 1994. Amperometric biosensor for in vivo glucose sensing based on glucose oxidase immobilized in a redox hydrogel. Biosensors & Bioelectronics 9:151-158.
Lowe, 1984. Biosensors, Trends in Biotechnology, 2(3):59-65.
Luong et al. 2004. Solubilization of Multiwall Carbon Nanotubes by 3-Aminopropyltriethoxysilane Towards the Fabrication of Electrochemical Biosensors with Promoted Electron Transfer. Electronanalysis 16(1-2):132-139.
Lyandres et al. (2008). Progress toward an in vivo surface-enhanced raman spectroscopy glucose sensor. *Diabetes Technology & Therapeutics*, 10(4): 257-265.
Makale et al. 2003. Tissue window chamber system for validation of implanted oxygen sensors. Am. J. Physiol. Heart Circ. Physiol. 284:H2288-2294.
Malin et al. 1999. Noninvasive Prediction of Glucose by Near-Infrared Diffuse Reflectance Spectroscopy. Clinical Chemistry 45:9, 1651-1658.
Maran et al. 2002. Continuous subcutaneous glucose monitoring in diabetic patients: A multicenter analysis. Diabetes Care 25(2):347-352.
Marena et al. 1993. The artifical endocrine pancreas in clinical practice and research. Panminerva Medica 35(2):67-74.
Mascini et al. 1989. Glucose electrochemical probe with extended linearity for whole blood. *J Pharm Biomed Anal* 7(12): 1507-1512.
Mastrototaro, J. J. 2000. The MiniMed continuous glucose monitoring system. Diabetes Technol Ther 2(Suppl 1):S13-8.
Mastrototaro et al. 2003. Reproducibility of the continuous glucose monitoring system matches previous reports and the intended use of the product. Diabetes Care 26:256; author reply p. 257.
Matsumoto et al. 1998. A micro-planar amperometeric glucose sensor unsusceptible to interference species. Sensors and Actuators B 49:68-72.
Matthews et al. 1988. An amperometric needle-type glucose sensor testing in rats and man. Diabetic Medicine 5:248-252.
Mazze et al. 2008. Characterizing glucose exposure for individuals with normal glucose tolerance using continuous glucose monitoring and ambulatory glucose profile analysis. Diab. Thechnol. & Therapeut., 10:149-159.
McCartney et al. 2001. Near-infrared fluorescence lifetime assay for serum glucose based on allophycocyanin-labeled concanavalin A. Anal Biochem 292:216-221.
McGrath et al. 1995. The use of differential measurements with a glucose biosensor for interference compensation during glucose determinations by flow injection analysis. Biosens Bioelectron 10:937-943.
Memoli et al. 2002. A comparison between different immobilised glucoseoxidase-based electrodes. J Pharm Biomed Anal 29:1045-1052.
Merriam-Webster Online Dictionary. Definition of "acceleration". http://www.merriam-webster.com/dictionary/Acceleration Jan. 11, 2010.
Merriam-Webster Online Dictionary. Definition of "system". http://www.merriam-webster.com/dictionary/System Jan. 11, 2010.
Merriam-Webster Online Dictionary. The term "nominal." http://www.m-w.com/dictionary/nominal.
Meyerhoff et al. 1992. On line continuous monitoring of subcutaneous tissue glucose in men by combining portable glucosensor with microdialysis. Diabetologia 35:1087-1092.
Moatti-Sirat et al., Reduction of acetaminophen interference in glucose sensors by a composite Nafion membrane: demonstration in rats and man, Diabetologia 37(6):610-616, Jun. 1994.
Morff et al. 1990. Microfabrication of reproducible, economical, electroenzymatic glucose sensors, Annual International Conference of the IEEE Engineering in Medicine and Biology Society, 12(2):0483-0484.
Mosbach et al. 1975. Determination of heat changes in the proximity of immobilized enzymes with an enzyme termistor and its use for the assay of metobolites, Biochim. Biophys. Acta. (Enzymology), 403:256-265.
Motonaka et al. 1993. Determination of cholesteral and cholesteral ester with novel enzyme microsensors, Anal. Chem. 65:3258-3261.

(56) References Cited

OTHER PUBLICATIONS

Muslu. 1991. Trickling filter performance. Apllied Biochemistry and Biotechnology 37:211-224.
Nafion® 117 Solution Product Description, Product No. 70160, Sigma-Aldrich Corp., St. Louis, MO.
Ohara et al. 1994. "Wired" enzyme electrodes for amperometric determination of glucose or lactate in the presence of interfering substances. Anal Chem 66:2451-2457.
Okuda et al. 1971. Mutarotase effect on micro determinations of D-glucose and its anomers with β-D-glucose oxidase. Anal Biochem 43:312-315.
Oxford English Dictionary Online. Definition of "impending". http://www.askoxford.com/results/?view=dev dict&field-12668446 Impending&branch= Jan. 11, 2010.
Palmisano et al. 2000. Simultaneous monitoring of glucose and lactate by an interference and cross-talk free dual electrode amperometric biosensor based on electropolymerized thin films. Biosensors & Bioelectronics 15:531-539.
Patel et al. 2003. Amperometric glucose sensors based on ferrocene containing polymeric electron transfer systems—a preliminary report. Biosens Bioelectron 18:1073-6.
Peacock et al. 2008. Cardiac troponin and outcome in acute heart failure. N. Engl. J. Med., 358: 2117-2126.
Pfeiffer, E.F. 1990. The glucose sensor: the missing link in diabetes therapy, Horm Metab Res Suppl. 24:154-164.
Pfeiffer et al. 1992. On line continuous monitoring of subcutaneous tissue glucose is feasible by combining portable glucosensor with microdialysis. Horm. Metab. Res. 25:121-124.
Pichert et al. 2000. Issues for the coming age of continuous glucose monitoring Diabetes Educ 26(6):969-980.
Pickup et al. 1989. Potentially-implantable, amperometric glucose sensors with mediated electron transfer: improving the operating stability. Biosensors 4:109-119.
Pickup et al. 1993. Developing glucose sensors for in vivo use. Elsevier Science Publishers Ltd (UK), Tibtech vol. 11: 285-291.
Pinner et al., Cross-linking of cellulose acetate by ionizing radiation, Nature, vol. 184, 1303-1304, Oct. 24, 1959.
Pitzer et al. 2001. Detection of hypoglycemia with the GlucoWatch biographer. Diabetes Care 24(5):881-885.
Poitout, et al. 1991. In Vitro and In Vivo Evaluation in Dogs of a Miniaturized Glucose Sensor, ASAIO Transactions, 37:M298-M300.
Poitout et al. 1994. Development of a glucose sensor for glucose monitoring in man: the disposable implant concept. Clinical Materials 15:241-246.
Postlethwaite et al. 1996. Interdigitated array electrode as an alternative to the rotated ring-disk electrode for determination of the reaction products of dioxygen reduction. Analytical Chemistry 68:2951-2958.
Prabhu et al. 1981. Electrochemical studies of hydrogen peroxide at a platinum disc electrode, Electrochimica Acta 26(6):725-729.
Quinn et al. 1995. Kinetics of glucose delivery to subcutaneous tissue in rats measured with 0.3-mm amperometric microsensors. The American Physiological Society E155-E161.
Quinn et al. 1997. Biocompatible, glucose-permeable hydrogel for in situ coating of implantable biosensors. Biomaterials 18:1665-1670.
Rabah et al., 1991. Electrochemical wear of graphite anodes during electrolysis of brine, Carbon, 29(2):165-171.
Reach et al. 1986. A Method for Evaluating in vivo the Functional Characteristics of Glucose Sensors. Biosensors 2:211-220.
Reach, G. 2001. Which threshold to detect hypoglycemia? Value of receiver-operator curve analysis to find a compromise between sensitivity and specificity. Diabetes Care 24(5):803-804.
Reach, Gerard. 2001. Letters to the Editor Re: Diabetes Technology & Therapeutics, 2000;2:49-56. Diabetes Technology & Therapeutics 3(1):129-130.
Rebrin et al. 1992. Subcutaenous glucose monitoring by means of electrochemical sensors: fiction or reality? J. Biomed. Eng. 14:33-40.

Reusch. 2004. Chemical Reactivity. Organometallic Compounds. Virtual Textbook of Organic Chem. pp. 1-16, http://www.cem.msu.edu/~reusch/VirtualText/orgmetal.htm.
Rhodes et al. 1994. Prediction of pocket-portable and implantable glucose enzyme electrode performance from combined species permeability and digital simulation analysis. Analytical Chemistry 66(9):1520-1529.
Rigla et al. 2008. Real-time continuous glucose monitoring together with telemedical assitance improves glycemic control and glucose stability in pump-treated patients. Diab. Thechnol. & Therapeut., 10:194-199.
Sakakida et al. 1992. Development of Ferrocene-Mediated Needle-Type Glucose Sensor as a Measure of True Subcutaneous Tissue Glucose Concentrations. Artif. Organs Today 2(2):145-158.
Salardi et al. 2002. The glucose area under the profiles obtained with continuous glucose monitoring system relationships with HbA1c in pediatric type 1 diabetic patients. Diabetes Care 25(10):1840-1844.
San Diego Plastics, Inc. 2009. Polyethylene Data Sheet, http://www.sdplastics.com/polyeth.html.
Sansen et al. 1990. A smart sensor for the voltammetric measurement of oxygen or glucose concentrations. Sensors and Actuators B 1:298-302.
Schmidt et al. 1993. Glucose concentration in subcutaneous extracellular space. Diabetes Care 16(5):695-700.
Schmidtke et al., Measurement and modeling of the transient difference between blood and subcutaneous glucose concentrations in the rat after injection of insulin. *Proc Natl Acad Sci U S A* 1998, 95, 294-299.
Schoemaker et al. 2003. The SCGM1 system: Subcutaneous continuous glucose monitoring based on microdialysis technique. Diabetes Technology & Therapeutics 5(4):599-608.
Schoonen et al. 1990 Development of a potentially wearable glucose sensor for patients with diabetes mellitus: design and in-vitro evaluation. Biosensors & Bioelectronics 5:37-46.
Service et al. 1987. Measurements of glucose control. Diabetes Care, 10: 225-237.
Service, R. F. 2002. Can sensors make a home in the body? Science 297:962-3.
Sharkawy et al. 1996. Engineering the tissue which encapsulates subcutaneous implants. I. Diffusion properties, J Biomed Mater Res, 37:401-412.
Slater-Maclean et al. 2008. Accuracy of glycemic measurements in the critically ill. Diab. Thechnol. & Therapeut., 10:169-177.
Sriyudthsak et al. 1996. Enzyme-epoxy membrane based glucose analyzing system and medical applications. Biosens Bioelectron 11:735-742.
Steil et al. 2003. Determination of plasma glucose during rapid glucose excursions with a subcutaneous glucose sensor. Diabetes Technology & Therapeutics 5(1):27-31.
Stern et al., 1957. Electrochemical polarization: 1. A theoretical analysis of the shape of polarization curves, Journal of the Electrochemical Society, 104(1):56-63.
Sumino T. et al. 1998. Preliminary study of continuous glucose monitoring with a microdialysis technique. Proceedings of the IEEE, 20(4):1775-1778.
Takegami et al. 1992. Pervaporation of ethanol water mixtures using novel hydrophobic membranes containing polydimethylsiloxane, Journal of Membrane Science, 75(93-105).
Tanenberg et al. 2000. Continuous glucose monitoring system: A new approach to the diagnosis of diabetic gastroparesis. Diabetes Technology & Therapeutics, 2 Suppl 1:S73-80.
Tatsuma et al. 1991. Oxidase/peroxidase bilayer-modified electrodes as sensors for lactate, pyruvate, cholesteral and uric acid, Analytica Chimica Acta, 242:85-89.
Thome et al. 1995.—Abstract—Can the decrease in subcutaneous glucose concentration precede the decrease in blood glucose level? Proposition for a push-pull kinetics hypothesis, Horm. Metab. Res. 27:53.
Thome-Duret et al. 1996. Use of a subcutaneous glucose sensor to detect decreases in glucose concentration prior to observation in blood, Anal. Chem. 68:3822-3826.
Thomé-Duret et al. 1998. Continuous glucose monitoring in the free-moving rat. Metabolism, 47:799-803.

(56) References Cited

OTHER PUBLICATIONS

Tierney et al. 2000. The GlucoWatch® biographer: A frequent, automatic and noninvasive glucose monitor. Ann. Med. 32:632-641.
Torjman et al., Glucose monitoring in acute care: technologies on the horizon, Journal of Deabetes Science and Technology, 2(2):178-181, Mar. 2008.
Trecroci, D. 2002. A Glimpse into the Future—Continuous Monitoring of Glucose with a Microfiber. Diabetes Interview 42-43.
Tse and Gough. 1987. Time-Dependent Inactivation of Immobilized Glucose Oxidase and Catalase. Biotechnol. Bioeng. 29:705-713.
Turner et al. 1984. Carbon Monoxide: Acceptor Oxidoreductase from *Pseudomonas thermocarboxydovorans* Strain C2 and its use in a Carbon Monoxide Sensor. Analytica Chimica Acta, 163: 161-174.
Updike et al. 1967. The enzyme electrode. Nature, 214:986-988.
Updike et al. 1988. Laboratory Evaluation of New Reusable Blood Glucose Sensor. Diabetes Care, 11:801-807.
Updike et al. 1994. Enzymatic glucose sensor: Improved long-term performance in vitro and in vivo. ASAIO Journal, 40(2):157-163.
Updike et al. 1997. Principles of long-term fully implanted sensors with emphasis on radiotelemetric monitoring of blood glucose form inside a subcutaneous foreign body capsule (FBC). In Fraser, ed., Biosensors in the Body. New York. John Wiley & Sons.
Updike et al. 2000. A subcutaneous glucose sensor with improved longevity, dynamic range, and stability of calibration. Diabetes Care 23(2):208-214.
Vadgama, P. Nov. 1981. Enzyme electrodes as practical biosensors. Journal of Medical Engineering & Technology 5(6):293-298.
Vadgama. 1988. Diffusion limited enzyme electrodes. NATO ASI Series: Series C, Math and Phys. Sci. 226:359-377.
Velho et al. 1989. In vitro and in vivo stability of electrode potentials in needle-type glucose sensors. Influence of needle material. Diabetes 38:164-171.
Wang et al. 1994. Highly Selective Membrane-Free, Mediator-Free Glucose Biosensor. Anal. Chem. 66:3600-3603.
Wang et al. 1997. Improved ruggedness for membrane-based amperometric sensors using a pulsed amperometric method. Anal Chem 69:4482-4489.
Ward et al. 2000. Understanding Spontaneous Output Fluctuations of an Amperometric Glucose Sensor: Effect of Inhalation Anesthesia and e of a Nonenzyme Containing Electrode. ASAIO Journal 540-546.
Ward et al. 2002. A new amperometric glucose microsensor: In vitro and short-term in vivo evaluation. Biosensors & Bioelectronics, 17:181-189.
Wiley Electrical and Electronics Engineering Dictionary. 2004. John Wiley & Sons, Inc. pp. 141, 142, 548, 549.
Wilkins et al. 1988. The coated wire electrode glucose sensor, Horm Metab Res Suppl., 20:50-55.
Wilson et al. 2000. Enzyme-based biosensors for in vivo measurements. Chem. Rev., 100:2693-2704.
Wood, W. et al. Mar. 1990. Hermetic Sealing with Epoxy. Mechanical Engineering 1-3.
Woodward. 1982. How Fibroblasts and Giant Cells Encapsulate Implants: Considerations in Design of Glucose Sensor. Diabetes Care 5:278-281.
Worsley et al., Measurement of glucose in blood with a phenylboronic acid optical sensor, Journal of Diabetes Science and Technology, 2(2):213-220, Mar. 2008.
Wright et al., Bioelectrochemical dehalogenations via direct electrochemistry of poly(ethylene oxide)-modified myoglobin, Electrochemistry Communications 1 (1999) 603-611.
Wu et al. 1999. In situ electrochemical oxygen generation with an immunoisolation device. Annals New York Academy of Sciences, pp. 105-125.
Yamasaki, Yoshimitsu. Sep. 1984. The development of a needle-type glucose sensor for wearable artificial endocrine pancreas. Medical Journal of Osaka University 35(1-2):25-34.
Yamasaki et al. 1989. Direct measurement of whole blood glucose by a needle-type sensor. Clinica Chimica Acta. 93:93-98.

Yang et al (1996). "A glucose biosensor based on an oxygen electrode: In-vitro performances in a model buffer solution and in blood plasma," Biomedical Instrumentation & Technology, 30:55-61.
Yang et al. 1998. Development of needle-type glucose sensor with high selectivity. Science and Actuators B 46:249-256.
Yang, et al. 2004. A Comparison of Physical Properties and Fuel Cell Performance of Nafion and Zirconium Phosphate/Nafion Composite Membranes. Journal of Membrane Science 237:145-161.
Ye et al. 1993. High Current Density 'Wired' Quinoprotein Glucose Dehydrogenase Electrode. Anal. Chem. 65:238-241.
Zethelius et al. 2008. Use of multiple biomarkers to improve the prediction of death from cardiovascular causes. N. Engl. J. Med., 358: 2107-2116.
Zhang et al (1993). Electrochemical oxidation of $H_2O_2$ on Pt and Pt + Ir electrodes in physiological buffer and its applicability to $H_2O_2$-based biosensors. *J. Electroanal. Chem.*, 345:253-271.
Zhang et al. 1993. In vitro and in vivo evaluation of oxygen effects on a glucose oxidase based implantable glucose sensor. Analytica Chimica Acta, 281:513-520.
Zhang et al. 1994. Elimination of the acetaminophen interference in an implantable glucose sensor. Analytical Chemistry 66(7):1183-1188.
Zhu et al. (1994). "Fabrication and characterization of glucose sensors based on a microarray $H_2O_2$ electrode." *Biosensors & Bioelectronics*, 9: 295-300.
Office Action dated Nov. 27, 2006 in U.S. Appl. No. 10/789,359.
Office Action dated Mar. 20, 2008 in U.S. Appl. No. 10/789,359.
Office Action dated May 17, 2007 in U.S. Appl. No. 11/077,759.
Office Action dated Jan. 5, 2010 in U.S. Appl. No. 11/078,232.
Office Action dated Dec. 31, 2009 in U.S. Appl. No. 11/077,714.
Office Action dated Jan. 27, 2010 in U.S. Appl. No. 11/077,714.
Office Action dated Sep. 2, 2009 in U.S. Appl. No. 11/078,072.
Office Action dated Feb. 18, 2010 in U.S. Appl. No. 11/078,072.
Office Action dated Jan. 21, 2010 in U.S. Appl. No. 11/157,365.
Office Action dated Aug. 25, 2009 in U.S. Appl. No. 11/334,876.
Office Action dated Oct. 29, 2009 in U.S. Appl. No. 11/360,819.
Office Action dated Feb. 23, 2010 in U.S. Appl. No. 12/113,508.
US 7,530,950, 5/2009, Brister et al. (withdrawn).
Bellucci et al. Jan. 1986. Electrochemical behaviour of graphite-epoxy composite materials (GECM) in aqueous salt solutions, Journal of Applied Electrochemistry, 16(1):15-22.
Bindra et al. 1991. Design and In Vitro Studies of a Needle-Type Glucose Senso for Subcutaneous Monitoring. Anal. Chem 63:1692-96.
Bobbioni-Harsch et al. 1993. Lifespan of subcutaneous glucose sensors and their performances during dynamic glycaemia changes in rats, J. Biomed. Eng. 15:457-463.
Brooks et al. "Development of an on-line glucose sensor for fermentation monitoring," Biosensors, 3:45-56 (1987/88).
Candas et al (1994). "An adaptive plasma glucose controller basedon a nonlinear insulin/glucose model." IEEE Transactions on Biomedical Engineering, 41(2): 116-124.
Davies, et al. 1992. Polymer membranes in clinical sensor applications. I. An overview of membrane function, Biomaterials, 13(14):971-978.
Heller, A. 1992. Electrical Connection of Enzyme Redox Centers to Electrodes. J. Phys. Chem. 96:3579-3587.
Hicks, 1985. In Situ Monitoring, Clinical Chemistry, 31(12):1931-1935.
Hu, et al. 1993. A needle-type enzyme-based lactate sensor for in vivo monitoring, Analytica Chimica Acta, 281:503-511.
Johnson et al. 1992. In vivo evaluation of an electroenzymatic glucose sensor implanted in subcutaneous tissue. Biosensors & Bioelectronics, 7:709-714.
Kawagoe et al. 1991. Enzyme-modified organic conducting salt microelectrode, Anal. Chem. 63:2961-2965.
Kerner et al. "The function of a hydrogen peroxide-detecting electroenzymatic glucose electrode is markedly impaired in human sub-cutaneous tissue and plasma," Biosensors & Bioelectronics, 8:473-482 (1993).
Lehmann et al. May 1994. Retrospective valication of a physiological model of glucose-iunsulin interaaction in tyhpe 1 diabetes mellitus, Med. Eng. Phys. 16:193-202.

(56) References Cited

OTHER PUBLICATIONS

Maidan et al. 1992. Elimination of Electrooxidizable Interferent-Produced Currents in Amperometric Biosensors, Analytical Chemistry, 64:2889-2896.
Mastrototaro et al. "An electroenzymatic glucose sensor fabricated on a flexible substrate," Sensors and Actuators B, 5:139-44 (1991).
McKean, et al. Jul. 7, 1988. A Telemetry Instrumentation System for Chronically Implanted Glucose and Oxygen Sensors. Transactions on Biomedical Engineering 35:526-532.
Moatti-Sirat et al. 1992. Towards continuous glucose monitoring: in vivo evaluation of a miniaturized glucose sensor implanted for several days in rat subcutaneous tissue. Diabetologia 35:224-230.
Murphy, et al. 1992. Polymer membranes in clinical sensor applications. II. The design and fabrication of permselective hydrogels for electrochemical devices, Biomaterials, 13(14):979-990.
Ohara, et al. Dec. 1993. Glucose electrodes based on cross-linked bis(2,2'-bipyridine)chloroosmium(+/2+) complexed poly(1-vinylimidazole) films, Analytical Chemistry, 65:3512-3517.
Pickup et al. "Implantable glucose sensors: choosing the appropriate sensor strategy," Biosensors, 3:335-346 (1987/88).
Pishko et al. "Amperometric glucose microelectrodes prepared through immobilization of glucose oxidase in redox hydrogels," Anal. Chem., 63:2268-72 (1991).
Reach et al. 1992. Can continuous glucose monitoring be used for the treatment of diabetes? Analytical Chemistry 64(5):381-386.
Sakakida et al. 1993. Ferrocene-Mediated Needle Type Glucose Sensor Covered with Newly Designed Biocompatible Membran, Sensors and Actuators B 13-14:319-322.
Shaw et al. "In vitro testing of a simply constructed, highly stable glucose sensor suitable for implantation in diabetic patients," Biosensors & Bioelectronics, 6:401-406 (1991).
Shichiri et al., 1989. Membrane Design for Extending the Long-Life of an Implantable Glucose Sensor. Diab. Nutr. Metab. 2:309-313.
Shults et al. 1994. A telemetry-instrumentation system for monitoring multiple subcutaneously implanted glucose sensors. IEEE Transactions on Biomedical Engineering 41(10):937-942.
Sternberg et al. 1988. Study and Development of Multilayer Needle-type Enzyme-based Glucose Microsensors. Biosensors 4:27-40.
Thomé-Duret et al. 1996. Modification of the sensitivity of glucose sensor implanted into subcutaneous tissue. Diabetes Metabolism, 22:174-178.
Thompson et al., In Vivo Probes: Problems and Perspectives, Department of Chemistry, University of Toronto, Canada, pp. 255-261, 1986.
Turner and Pickup, "Diabetes mellitus: biosensors for research and management," *Biosensors*, 1:85-115 (1985).
Updike et al. 1997. Principles of long-term fully implanted sensors with emphasis on radiotelemetric monitoring of blood glucose form inside a subcutaneous foreign body capsule (FBC). In Fraser, ed., Biosensors in the Body. New York. John Wiley & Sons, pp. 117-137.
Velho et al. 1989. Strategies for calibrating a subcutaneous glucose sensor. Biomed Biochim Acta 48(11/12):957-964.
von Woedtke et al. 1989. In situ calibration of implanted electrochemical glucose sensors. Biomed Biochim. Acta 48(11/12):943-952.
Wikipedia 2006. "Intravenous therapy," http://en.wikipedia.org/wiki/Intravenous_therapy, Aug. 15, 2006, 6 pp.
Official Communication in EP App. No. 05723951.9, dated Oct. 10, 2008.
European Search Report for App. No. 98908875.2 dated Apr. 29, 2004.
ISR and WO for PCT/US07/80848 filed Oct. 9, 2007.
Office Action dated Mar. 31, 2008 in U.S. Appl. No. 11/077,759.
Office Action dated Jul. 10, 2008 in U.S. Appl. No. 11/077,759.
Office Action dated Aug. 11, 2008 in U.S. Appl. No. 11/360,819.
Office Action dated Aug. 26, 2008 in U.S. Appl. No. 11/334,876.
Office Action dated Sep. 16, 2008 in U.S. Appl. No. 11/077,714.
Office Action dated Oct. 3, 2008 in U.S. Appl. No. 10/789,359.
Office Action dated Nov. 12, 2008 in U.S. Appl. No. 11/078,232.
Office Action dated Nov. 28, 2008 in U.S. Appl. No. 11/333,877.

Office Action dated Dec. 26, 2008 in U.S. Appl. No. 11/360,819.
Office Action dated Jan. 7, 2009 in U.S. Appl. No. 11/157,365.
Office Action dated Jan. 29, 2009, in U.S. Appl. No. 11/360,252.
Office Action dated Mar. 5, 2009 in U.S. Appl. No. 11/078,232.
Office Action dated Apr. 16, 2009 in U.S. Appl. No. 11/077,714.
Office Action dated May 26, 2009 in U.S. Appl. No. 11/077,759.
Office Action dated Jun. 29, 2009 in U.S. Appl. No. 11/333,837.
Office Action dated Jul. 21, 2009 in U.S. Appl. No. 11/078,232.
Office Action dated Jul. 21, 2009 in U.S. Appl. No. 11/157,365.
Office Action dated Jul. 23, 2009, in U.S. Appl. No. 11/360,252.
Abel et al. 2002. Biosensors for in vivo glucose measurement: can we cross the experimental stage. Biosens Bioelectron 17:1059-1070.
Armour et al. Dec. 1990. Application of Chronic Intravascular Blood Glucose Sensor in Dogs. Diabetes 39:1519-1526.
Aussedat et al. 1997. A user-friendly method for calibrating a subcutaneous glucose sensor-based hypoglycaemic alarm. Biosensors & Bioelectronics 12(11):1061-1071.
Baker et al. 1996. Dynamic delay and maximal dynamic error in continuous biosensors. Anal Chem 68(8):1292-1297.
Bani Amer, M. M. 2002. An accurate amperometric glucose sensor based glucometer with eliminated cross-sensitivity. J Med Eng Technol 26(5):208-213.
Bard et al. 1980. Electrochemical Methods. John Wiley & Sons, pp. 173-175.
Bland et al. 1986. Statistical methods for assessing agreement between two methods of clinical measurement. Lancet 1:307-310.
Bland et al. 1990. A note on the use of the intraclass correlation coefficient in the evaluation of agreement between two methods of measurement. Comput. Biol. Med. 20(5):337-340.
Bode et al. 1999. Continuous glucose monitoring used to adjust diabetes therapy improves glycosylated hemoglobin: A pilot study. Diabetes Research and Clinical Practice 46:183-190.
Bode, B. W. 2000. Clinical utility of the continuous glucose monitoring system. Diabetes Technol Ther, 2(Suppl 1):S35-41.
Bode et al. 2000. Using the continuous glucose monitoring system to improve the management of type 1 diabetes. Diabetes Technology & Therapeutics, 2(Suppl 1):S43-48.
Bolinder et al. 1992. Microdialysis measurement of the absolute glucose concentration in subcutaneous adipose tissue allowing glucose monitoring in diabetic patients. Diabetologia 35:1177-1180.
Bremer et al. 1999. Is blood glucose predictable from previous values? A solicitation for data. Diabetes 48:445-451.
Cass et al. "Ferrocene-mediated enzyme electrodes for amperometric determination of glucose," Anal. Chem., 36:667-71 (1984).
Chia et al. 2004. Glucose sensors: toward closed loop insulin delivery. Endocrinol Metab Clin North Am 33:175-95.
Choleau et al. 2002. Calibration of a subcutaneous amperometric glucose sensor implanted for 7 days in diabetic patients. Part 2. Superiority of the one-point calibration method. Biosensors and Bioelectronics 17:647-654.
Csöregi et al. 1994. Amperometric microbiosensors for detection of hydrogen peroxide and glucose based on peroxidase-modified carbon fibers. Electroanalysis 6:925-933.
Frost et al. 2002. Implantable chemical sensors for real-time clinical monitoring: Progress and challenges. Current Opinion in Chemical Biology 6:633-641.
Garg et al. 2004. Improved Glucose Excursions Using an Implantable Real-Time continuous Glucose Sensor in Adults with Type I Diabetes. Diabetes Care 27:734-738.
Gilligan et al. 2004, Feasibility of continuous long-term glucose monitoring from a subcutaneous glucose sensor in humans. Diabetes Technol Ther 6:378-386.
Guerci et al., Clinical performance of CGMS in type 1 diabetic patents treated by continuous subcutaneous insulin infusion using insulin analogs, Diabetes Care, 26:582-589, 2003.
Heller, "Electrical wiring of redox enzymes," Acc. Chem. Res., 23:128-134 (1990).
Heller, A. 1999. Implanted electrochemical glucose sensors for the management of diabetes. Annu Rev Biomed Eng 1:153-175.
Hunter, I., Jones, L., Kanigan, T., Brenan, C., Sanbol, L. Sosnowski, L. 2000. Minimally Invasive Glucose Sensor and Insulin Delivery System. MIT Home Automation and Healthcare Consortium. Progress Report No. 25.

(56) References Cited

OTHER PUBLICATIONS

Kerner, W. 2001. Implantable glucose sensors: Present status and future developments. Exp. Clin. Endocrinol. Diabetes 109(Suppl 2):S341-346.
Kiechle, F.L. 2001. The impact of continuous glucose monitoring on hospital point-of-care testing programs. Diabetes Technol Ther 3:647-649.
Koschinsky et al. 1998. New approach to technical and clinical evaluation of devices for self-monitoring of blood glucose. Diabetes Care 11(8): 619-619.
Kurnik et al. 1999. Application of the mixtures of experts algorithm for signal processing in a noninvasive glucose monitoring system. Sensors and Actuators B, 60:19-26.
Lerner et al. 1984. An implantable electrochemical glucose sensor. Ann. N. Y. Acad. Sci. 428:263-278.
Lynch et al. 2001. Estimation-based model predictive control of blood glucose in type I diabetics: A simulation study. Proceedings of the IEEE 27th Annual Northeast Bioengineering Conference, pp. 79-80.
March, W. F. 2002. Dealing with the delay. Diabetes Technol Ther 4(1):49-50.
Martin, R. F. 2000. General Deming regression for estimating systematic bias and its confidence interval in method-comparison studies. Clinical Chemistry, 46(1):100-104.
Moatti-Sirat, D et al. 1992. Evaluating in vitro and in vivo the interference of ascorbate and acetaminophen on glucose detection by a needle-type glucose sensor. Biosensors and Bioelectronics 7:345-352.
Monsod et al. 2002. Do sensor glucose levels accurately predict plasma glucose concentrations during hypoglycemia and hyperinsulinemia? Diabetes Care 25(5):889-893.
Pickup et al. "In vivo molecular sensing in diabetes mellitus: an implantable glucose sensor with direct electron transfer," Diabetologia, 32:213-217 (1989).
Poitout et al. 1993. A glucose monitoring system for on line estimation in man of blood glucose concentration using a miniaturized glucose sensor implanted in the subcutaneous tissue and a wearable control unit. Diabetologia 36:658-663.
Rebrin et al. "Automated feedback control of subcutaneous glucose concentration in diabetic dogs," Diabetologia, 32:573-76 (1989).
Rinken et al. 1998. Calibration of glucose biosensors by using pre-steady state kinetic data. Biosensors & Bioelectronics, 13:801-807.
Rivers et al., Central venous oxygen saturation monitoring in the critically ill patient, Current Opinion in Critical Care, 7:204-211, 2001.
Sansen et al. 1985. "Glucose sensor with telemetry system." In Ko, W. H. (Ed.). Implantable Sensors for Closed Loop Prosthetic Systems. Chap. 12, pp. 167-175, Mount Kisco, NY: Futura Publishing Co.
Selam, J. L. 1997. Management of diabetes with glucose sensors and implantable insulin pumps. From the dream of the 60s to the realities of the 90s. ASAIO J, 43:137-142.
Service et al. 1970. Mean amplitude of glycemic excursions, a measure of diabetic instability. Diabetes, 19: 644-655.
Shichiri et al. 1982. Wearable artificial endocrine pancrease with needle-type glucose sensor. Lancet 2:1129-1131.
Shichiri et al. 1983. Glycaemic Control in Pancreatectomized Dogs with a Wearable Artificial Endocrine Pancreas. Diabetologia 24:179-184.
Shichiri et al. 1985. Needle-type Glucose Sensor for Wearable Artificial Endocrine Pancreas in Implantable Sensors 197-210.
Shichiri et al. 1986. Telemetry Glucose Monitoring Device with Needle-Type Glucose Sensor: A Useful Tool for Blood Glucose Monitoring in Diabetic Individuals. Diabetes Care, Inc. 9(3):298-301.
Skyler, J. S. 2000. The economic burden of diabetes and the benefits of improved glycemic control: The potential role of a continuous glucose monitoring system. Diabetes Technology & Therapeutics 2 Suppl 1:S7-12.
Sokol et al. 1980, Immobilized-enzyme rate-determination method for glucose analysis, Clin. Chem. 26(1):89-92.
Sternberg et al. 1996. Does fall in tissue glucose precede fall in blood glucose? Diabetologia 39:609-612.
Tierney et al. 2000. Effect of acetaminophen on the accuracy of glucose measurements obtained with the GlucoWatch biographer. Diabetes Technol Ther 2:199-207.
Tilbury et al. 2000. Receiver operating characteristic analysis for intelligent medical systems—A new approach for finding confidence intervals. IEEE Transactions on Biomedical Engineering 47(7):952-963.
Trajanoski et al. 1998. Neural predictive controller for insulin delivery using the subcutaneous route. IEEE Transactions on Biomedical Engineering 45(9):1122-1134.
Unger et al. 2004. Glucose control in the hospitalized patient. Emerg Med 36(9):12-18.
Updike et al. 1979. Continuous glucose monitor based on an immobilized enzyme electrode detector. J Lab Clin Med, 93(4):518-527.
Updike et al. 1982. Implanting the glucose enzyme electrode: Problems, progress, and alternative solutions. Diabetes Care, 5(3):207-212.
Utah Medical Products Inc., Blood Pressure Tranducers product specifications. 6 pp. 2003-2006, 2003.
Van den Berghe 2004. Tight blood glucose control with insulin in "real-life" intensive care. Mayo Clin Proc 79(8):977-978.
Wagner et al. 1998. Continuous amperometric monitoring of glucose in a brittle diabetic chimpanzee with a miniature subcutaneous electrode. Proc. Natl. Acad. Sci. A, 95:6379-6382.
Ward et al. 1999. Assessment of chronically implanted subcutaneous glucose sensors in dogs: The effect of surrounding fluid masses. ASAIO Journal, 45:555-561.
Ward et al. 2000. Rise in background current over time in a subcutaneous glucose sensor in the rabbit: Relevance to calibration and accuracy. Biosensors & Bioelectronics, 15:53-61.
Wientjes, K. J. C. 2000. Development of a glucose sensor for diabetic patients (Ph.D. Thesis).
Wilkins et al. 1995. Glucose monitoring: state of the art and future possibilities. Med Eng Phys 18:273-288.
Wilkins et al. 1995. Integrated implantable device for long-term glucose monitoring. Biosens. Bioelectron 10:485-494.
Wilson et al. 1992. Progress toward the development of an implantable sensor for glucose. Clin. Chem. 38(9):1613-1617.
Zamzow et al. Development and evaluation of a wearable blood glucose monitor. pp. M588-M591, 1990.
Zhu et al. 2002. Planar amperometric glucose sensor based on glucose oxidase immobilized by chitosan film on prussian blue layer. Sensors, 2:127-136.
Office Action dated Sep. 30, 2002 in U.S. Appl. No. 09/636,369.
Office Action dated Jul. 15, 2008 in U.S. Appl. No. 10/633,367.
Office Action dated May 22, 2006 in U.S. Appl. No. 10/896,772.
Office Action dated Dec. 14, 2005 in U.S. Appl. No. 10/896,772.
Office Action dated Jul. 19, 2005 in U.S. Appl. No. 10/896,772.
Office Action dated Jan. 11, 2005 in U.S. Appl. No. 10/896,772.
Office Action dated Dec. 21, 2004 in U.S. Appl. No. 10/632,537.
Office Action dated Oct. 20, 2004 in U.S. Appl. No. 10/632,537.
Office Action dated Jun. 17, 2008 in U.S. Appl. No. 11/038,340.
Office Action dated May 29, 2008 in U.S. Reexam. No. 95/001,039.
Office Action dated Feb. 12, 2007 in U.S. Appl. No. 10/633,404.
Office Action dated Jun. 17, 2008 in U.S. Reexam. No. 95/001,038.
Office Action dated Jun. 12, 2008 in U.S. Appl. No. 10/633,329.
Office Action dated Feb. 4, 2008 in U.S. Appl. No. 10/633,329.
Office Action dated Jul. 30, 2007 in U.S. Appl. No. 10/633,329.
Office Action dated Mar. 26, 2007 in U.S. Appl. No. 10/633,329.
Office Action dated Oct. 5, 2006 in U.S. Appl. No. 10/633,329.
Office Action dated Jun. 24, 2008 n U.S. Appl. No. 11/007,920.
Office Action dated Jan. 27, 2006 in U.S. Appl. No. 11/007,635.
Office Action dated Nov. 28, 2007 in U.S. Appl. No. 10/991,966.
Office Action dated Jul. 22, 2008 in U.S. Appl. No. 10/991,966.
Office Action dated Jan. 15, 2008 in U.S. Appl. No. 11/034,344.
Office Action in U.S. Appl. No. 10/838,909 mailed Jun. 5, 2008.
Office Action dated May 5, 2008 in U.S. Appl. No. 11/078,232.
Office Action dated Jun. 1, 2007 in U.S. Appl. No. 11/077,740.
Office Action dated Nov. 1, 2007 in U.S. Appl. No. 11/077,740.
Office Action dated Feb. 7, 2008 in U.S. Appl. No. 11/077,740.
Office Action dated Dec. 31, 2007 in U.S. Appl. No. 11/077,765.

(56) References Cited

OTHER PUBLICATIONS

Office Action dated May 16, 2008 in U.S. Appl. No. 11/077,765.
Office Action dated Sep. 19, 2008 in U.S. Appl. No. 11/077,765.
Office Action dated Jul. 27, 2007 in U.S. Appl. No. 11/077,714.
Office Action dated Apr. 10, 2007 in U.S. Appl. No. 11/077,714.
Office Action dated Oct. 11, 2006 in U.S. Appl. No. 11/077,714.
Office Action dated Jan. 10, 2008 in U.S. Appl. No. 11/077,714.
Office Action dated Jun. 26, 2008 in U.S. Appl. No. 11/157,365.
Office Action dated Oct. 4, 2006 in U.S. Appl. No. 11/334,876.
Office Action dated Sep. 25, 2007 in U.S. Appl. No. 11/334,876.
Office Action dated May 2, 2008 in U.S. Appl. No. 11/334,876.
Office Action dated Jun. 30, 2008 in U.S. Appl. No. 11/360,252.
IPRP for PCT/US05/006301 filed Feb. 24, 2005.
ISR and WO for PCT/US05/006301 filed Feb. 24, 2005.
Official Communication in European App. No. 05723951.9, dated Nov. 21, 2007.
Jaffari et al., Recent advances in amperometric glucose biosensors for in vivo monitoring, Physiol. Meas. 16 (1995) 1-15.
Jobst et al., (1996) Thin-Film Microbiosensors for Glucose-Lactate Monitoring, Anal Chem. 8(18): 3173-3179.
Moussy et al. 1993. Performance of subcutaneously implanted needle-type glucose sensors employing a novel trilayer coating, Anal Chem. 85: 2072-2077.
Moussy, Francis (Nov. 2002) Implantable Glucose Sensor: Progress and Problems, Sensors, 1:270-273.
Pickup et al. 1993. Responses and Calibration of Amperometric Glucose Sensors Implanted in the Subcutaneous Tissue of Man. ACTA Diabetol, pp. 143-148.
Samuels, M.P. 2004. The effects of flight and altitude. Arch Dis Child. 89: 448-455.
EPO Communication dated Jan. 28, 2011 for EP 05723951.9, filed Feb. 24, 2005.
EPO Communication dated Aug. 3, 2010 for EP 10163654.6, filed Feb. 24, 2005.
EPO Communication dated Aug. 3, 2010 for EP 10163675.1, filed Feb. 24, 2005.
EPO Communication dated Mar. 17, 2011 for EP 10163671.1, filed Feb. 24, 2005.
IPRP dated Apr. 22, 2010 for PCT/US07/080848, filed Oct. 9, 2007.
JIPO Communication dated Aug. 17, 2010 in JP Application No. 2007-500777 filed Feb. 24, 2005.
Electronic File History of U.S. Appl. No. 10/789,359, filed Feb. 26, 2004 (now US Patent No. 7,591,801, issued Sep. 22, 2009) containing Office Action(s) dated Aug. 9, 2006, Nov. 27, 2006, Mar. 20, 2008, Oct. 3, 2008, Feb. 24, 2009, Mar. 30, 2009, Apr. 22, 2009, Apr. 23, 2009, and Jul. 15, 2009 and Applicant(s) Response(s) filed Aug. 31, 2006, Feb. 6, 2007, May 28, 2008, Nov. 24, 2008, Mar. 31, 2009, and Apr. 22, 2009.
Electronic File History of U.S. Appl. No. 12/536,852, filed Aug. 6, 2009 containing Office Action(s) dated Jun. 25, 2010, Oct. 18, 2010, and Feb. 25, 2011 and Applicant(s) Response(s) filed Aug. 3, 2010, Dec. 8, 2010, and May 11, 2011.
Berger et al. (1988), Proceedings of the Annual Symposium on Computer Applications in Medical Care, pp. 52-57. Computer Programs to Assist the Physician in the analysis of Se.
NewsRx (Aug. 3, 2003). Medical Letter on the CDC & FDA via NewsRx.com "Glucose Monitoring: FDA OKs new device to manage diabetes".
Renard, Eric (2002), Current Opinion in Pharmacology 2:708-716, Implantable closed-loop glucose sensing and insulin delivery: the future for insulin pump therapy.
American Diabetes Association. (Jan. 2007) Position Statement: Diagnosis and Classification of Diabetes Mellitus. Diabetes Care 30(Supp. 1):S42-S47.
American Diabetes Association. (Jan. 2007) Position Statement: Standards of Medical Care in Diabetes—2007; Diabetes Care 30(Supp. 1):S4-S41.
American Diabetes Association. (Jan. 2007) Summary of Revisions for the 2007 Clinical Practice Recommendations; Diabetes Care 30(Supp. 1): S3.
Aussedat et al. (2000) Interstitial glucose concentration and glycemia: Implications for continuous subcutaneous glucose monitoring; Am J Physiol Endocrinol Metab 278: E716-E728.
Chase et al. (2005) Targeted Glycemic Reduction in Critical Care Using Closed-Loop Control; Diab Tech Therap. 7(2): 274-282.
de Vos et al., Considerations for successful transplantation of encapsulated pancreatic islets, Diabetol. (2002) 45: 159-173.
Garg, Satish K. (2005) New Insulin Analogues; Diab Tech Therap. 7(5): 813-817.
Gough. (May 2001) The implantable glucose sensor: An example of bioengineering design. Introduction to Bioengineering, Chapter 3, pp. 57-66.
Hagvik, Joakim. (Mar. 2007) Glucose Measurment: Time for a Gold Standard; J Diab Scie Technol. 1(2): 169-172.
Heinemann et al. (2004) Review: Measurement of Insulin Absorption and Insulin Action. Diab Tech Therap. 6(5): 698-718.
Heinemann, Lutz. (2002) Review: Variability of Insulin Absorption and Insulin Action. Diab Tech Therap. 4(5): 673-682.
Heinemann, Lutz. (Mar. 2007) Measurement Quality of Blood Glucose Meters: Is there a need for an institution with an unbiased view? J Diab Scie Technol. 1(2): 178-180.
Hovorka et al. (2004) Closing the Loop: The Adicol Experience. Diab Tech Therap. 6(3): 307-318.
Hunsley et al. (Mar. 2007) Whole Blood Glucose Standard Is Key to Accurate Insulin Dosages. J Diab Scie Technol. 1(2): 173-177.
Jones et al. (2005) Optimal Insulin Pump Dosing and Postprandial Glycemia Following a Pizza Meal Using the Continuous Glucose Monitoring System; Diab Tech Therap. 7(2): 233-240.
Kizilel et al. (2005) Review: The Bioartificial Pancreas: Progress and Challenges; Diab Tech Therap. 7(6): 968-985.
Klonoff, David C. (2002) Editorial: Current, Emerging, and Future Trends in Metabolic Monitoring; Diab Tech Therap. 4(5): 582-588.
Koschinsky et al. (2003) Review: Glucose Sensors and the Alternate Site Testing-like Phenomenon: Relationship Between Rapid Blood Glucose Changes and Glucose Sensor Signals. Diab Tech Therap. 5(5): 829-842.
Lee et al. (May 2007) Combined Insulin Pump Therapy with Real-time Continuous Glucose Monitoring Significantly Improves Glycemic Control Compared to Multiple Daily Injection Therapy in Pump Naive Patients with Type 1 Diabetes; Single Center Pilot Study Experience; J Diab Scie Tech. 1(3): 400-404.
Rafael, Ehab, Cell Transplantation and Immunoisolation: Studies on a macroencapsulation device, Departments of Transplantation Surgery and Pathology, Karolinska Institutet, Huddinge Hospital, Stockholm, Sweden (1999) pp. 1-82.
Ristic et al. (2003) Review: Effets of Rapid-acting Insulin Analogs on Overall Glycemic Control in Type 1 and Type 2 Diabetes Mellitus; Diab Tech Therap. 5(1): 57-66.
Smith et al. 1991. A Comparison of Islet Transplantation and Subcutaneous Insulin Injections for the Treatment of Diabetes Mellitus, Comput Biol Med. 21(6): 417-427.
Street et al. Dec. 2004. Islet Graft Assessment in the Edmonton Protocol: Implications for Predicting Long-Term Clinical Outcome, Diabetes, 53: 3107-3114.
Thennadil et al. (2001) Comparison of Glucose Concentration in Interstitial Fluid, and Capillary and Venous Blood During Rapid Changes in Blood Glucose Levels; Diab Tech Therap. 3(3): 357-365.
Vesper et al. (2006) Assessment of Trueness of a Glucose Monitor Using Interstitial Fluid and Whole Blood as Specimen Matrix; Diab Tech Therap. 8(1): 76-80.
Wentholt et al. (2007) Relationship between Interstitial and Blood Glucose in Type 1 Diabetes Patients: Delay and the Push-pull Phenomenon Revisited; Diab Tech Therap. 9(2): 169-175.

\* cited by examiner

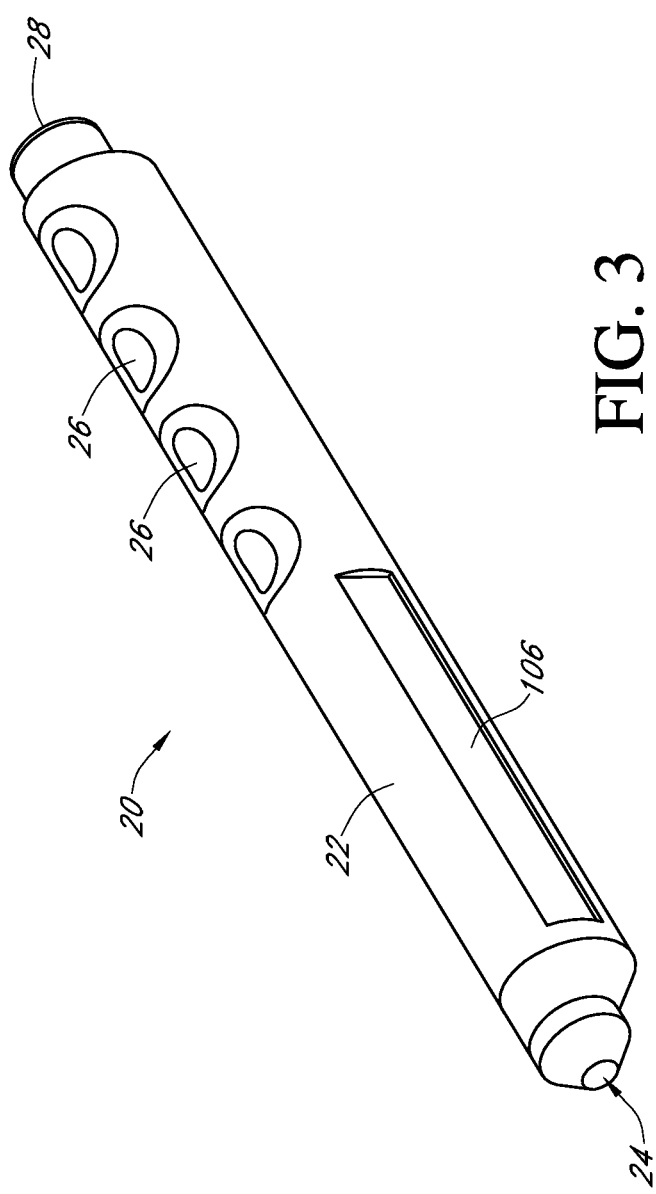

INTEGRATED MEDICAMENT DELIVERY DEVICE FOR USE WITH CONTINUOUS ANALYTE SENSOR

CROSS-REFERENCE TO RELATED APPLICATIONS

This application is a continuation-in-part of U.S. application Ser. No. 10/789,359 filed Feb. 26, 2004, and claims the benefit of U.S. Provisional Application No. 60/942,787 filed Jun. 8, 2007, the disclosures of which are hereby expressly incorporated by reference in their entirety and are hereby expressly made a portion of this application.

FIELD OF THE INVENTION

The present invention relates generally to systems and methods monitoring glucose in a host. More particularly, the present invention relates to an integrated medicament delivery device and continuous glucose sensor.

BACKGROUND OF THE INVENTION

Diabetes mellitus is a disorder in which the pancreas cannot create sufficient insulin (Type I or insulin dependent) and/or in which insulin is not effective (Type 2 or non-insulin dependent). In the diabetic state, the victim suffers from high blood sugar, which can cause an array of physiological derangements (for example, kidney failure, skin ulcers, or bleeding into the vitreous of the eye) associated with the deterioration of small blood vessels. A hypoglycemic reaction (low blood sugar) can be induced by an inadvertent overdose of insulin, or after a normal dose of insulin or glucose-lowering agent accompanied by extraordinary exercise or insufficient food intake.

Conventionally, a diabetic person carries a self-monitoring blood glucose (SMBG) monitor, which typically comprises uncomfortable finger pricking methods. Due to the lack of comfort and convenience, a diabetic will normally only measures his or her glucose level two to four times per day. Unfortunately, these time intervals are so far spread apart that the diabetic will likely find out too late, sometimes incurring dangerous side effects, of a hyper- or hypo-glycemic condition. In fact, it is not only unlikely that a diabetic will take a timely SMBG value, but the diabetic will not know if their blood glucose value is going up (higher) or down (lower) based on conventional methods, inhibiting their ability to make educated insulin therapy decisions.

Home diabetes therapy requires personal discipline of the user, appropriate education from a doctor, proactive behavior under sometimes-adverse situations, patient calculations to determine appropriate therapy decisions, including types and amounts of administration of insulin and glucose into his or her system, and is subject to human error. Technologies are needed that ease the burdens faced by diabetic patients, simplify the processes involved in treating the disease, and minimize user error which can cause unnecessarily dangerous situations in some circumstances.

SUMMARY OF THE INVENTION

Systems and methods for monitoring glucose are provided that offer one or more benefits and/or advantages, for example, easing the burdens faced by diabetic patients, simplifying the processes involved in treating diabetes, and minimizing user error which can cause unnecessarily dangerous situations in some circumstances.

Accordingly, in a first aspect, an integrated system for monitoring and treating diabetes is provided, the system comprising: a medicament injection pen configured and arranged for injecting an amount of a medicament into a host; and an integrated receiver configured and arranged to receive sensor data from a continuous glucose sensor, wherein the sensor data is indicative of a glucose concentration of the host in vivo wherein the integrated receiver comprises electronics configured and arranged to process the sensor data.

In an embodiment of the first aspect, the electronics are further configured to calculate at least one of time of medicament therapy and amount of medicament therapy.

In an embodiment of the first aspect, the integrated receiver comprises a housing, wherein the medicament injection pen is integrally formed with the housing.

In an embodiment of the first aspect, the integrated receiver comprises a housing, and wherein the medicament injection pen is detachably connectable to the housing.

In an embodiment of the first aspect, communication between the medicament injection pen and the receiver is initiated based at least in part on detachable connection of the medicament injection pen and the housing.

In an embodiment of the first aspect, the integrated system further comprises a user interface configured and arranged for at least one of input of host information, output of sensor data, and medicament therapy.

In an embodiment of the first aspect, the user interface is further configured to display a graphical representation of at least one of sensor data and medicament delivery data, wherein a solid line represents at least one of a target glucose concentration and a range.

In an embodiment of the first aspect, the integrated electronics are configured and arranged to require validation prior to injecting an amount of medicament into the host.

In an embodiment of the first aspect, the receiver is configured to communicate in at least one of wiredly with a single-point glucose monitor and wirelessly with a single-point glucose monitor.

In an embodiment of the first aspect, the medicament injection pen comprises a motor.

In an embodiment of the first aspect, the motor is configured to set the amount of medicament.

In an embodiment of the first aspect, the motor is configured to control a rate of medicament injection into a host.

In an embodiment of the first aspect, the receiver is configured to remotely control the motor.

In an embodiment of the first aspect, the medicament injection pen and the receiver each comprise mutually engaging electrical contacts, and wherein the mutually engaging electrical contacts are configured to allow communication between the medicament injection pen and the receiver.

In an embodiment of the first aspect, the system is configured to initiate communication between the medicament injection pen and the receiver in response to engagement of the electrical contacts.

In an embodiment of the first aspect, the system is configured to communicate medicament delivery data between the medicament injection pen and the receiver in response to engagement of the electrical contacts.

In an embodiment of the first aspect, the integrated system further comprises a receptacle configured and arranged to receive at least one of parts associated with the medicament injection pen and accessories associated with the medicament injection pen.

In an embodiment of the first aspect, at least one of the parts associated with the medicament injection pen and accessories associated with the medicament injection pen comprise a medicament cartridge.

In an embodiment of the first aspect, the integrated system further comprises a medicament injection pen kit, wherein the medicament injection pen kit is configured to receive the medicament injection pen, and wherein the medicament injection pen kit comprises a housing comprising a user interface, and wherein the integrated receiver is located within the housing and operably connected to the user interface.

In a second aspect an integrated system for monitoring and treating diabetes is provided, the system comprising: a receiver configured and arranged to receive sensor data from an operably connected continuous glucose sensor, wherein the continuous glucose sensor is configured and arranged to generate sensor data associated with a glucose concentration of a host; integrated electronics configured to process the sensor data and to generate a medicament therapy; and a medicament injection pen configured to inject an amount of medicament into the host.

In an embodiment of the second aspect, the medicament therapy comprises at least one of an amount of medicament therapy and a time of medicament therapy delivery.

In an embodiment of the second aspect, the receiver and the medicament injection pen are integrally formed.

In an embodiment of the second aspect, the integrated system further comprises a receptacle configured and arranged to receive at least one of parts associated with the medicament injection pen and accessories associated with the medicament injection pen.

In an embodiment of the second aspect, the medicament injection pen is detachably connectable to the receiver.

In an embodiment of the second aspect, the medicament injection pen and receiver each comprise mutually engaging electrical contacts, and wherein the mutually engaging electrical contacts are configured to allow communication between the medicament injection pen and the receiver.

In an embodiment of the second aspect, the system is configured to initiate communication between the medicament injection pen and the receiver in response to engagement of the mutually engaging electrical contacts.

In an embodiment of the second aspect, the system is configured to communicate the medicament therapy between the receiver and the medicament injection pen in response to engagement of the mutually engaging electrical contacts.

In an embodiment of the second aspect, the integrated system further comprises a housing integrally formed with the receiver, wherein the integrated electronics are located with the housing.

In an embodiment of the second aspect, the medicament injection pen is detachably connectable with the housing.

In an embodiment of the second aspect, the receiver further comprises a user interface, wherein the integrated electronics are configured to display at least one of sensor data and the medicament therapy thereon.

In an embodiment of the second aspect, the receiver comprises a housing, and wherein the user interface is located on the receiver housing.

In an embodiment of the second aspect, the integrated system further comprises a user interface configured to display at least one of the sensor data and the medicament therapy.

In an embodiment of the second aspect, the integrated electronics are further configured to display a representation of medicament delivery on the user interface, and wherein the representation of medicament delivery is substantially adjacent to substantially time-corresponding sensor data.

In an embodiment of the second aspect, the integrated electronics are further configured to display a representation of sensor data on the user interface, wherein the representation comprises at least one of a target glucose concentration and a range.

In an embodiment of the second aspect, the user interface comprises a flexible LED screen operably connected to at least one of the receiver and the medicament injection pen, and wherein the integrated electronics are configured to display continuous glucose sensor data on the flexible LED screen.

In an embodiment of the second aspect, the user interface comprises an image projection system configured to project continuous glucose sensor data onto a surface.

In an embodiment of the second aspect, the medicament injection pen comprises a motor.

In an embodiment of the second aspect, the motor is configured to automatically set the amount of medicament.

In an embodiment of the second aspect, the motor is configured to control a rate of medicament injection into the host.

In an embodiment of the second aspect, the receiver is configured to remotely control the motor.

In an embodiment of the second aspect, the integrated system further comprises a medicament injection pen kit comprising the receiver and the integrated electronics, wherein the medicament injection pen kit is configured to receive the medicament injection pen.

In an embodiment of the second aspect, the integrated system further comprises a user interface, wherein the integrated electronics are configured to display at least one of sensor data and the medicament therapy thereon.

In an embodiment of the second aspect, the medicament injection pen kit further comprises a receptacle configured and arranged to receive at least one of a medicament cartridge and a medicament injection pen needle.

In a third aspect, a method for monitoring and treating diabetes using an integrated diabetes monitoring and treatment device is provided, the method comprising: receiving sensor data from a continuous glucose sensor, wherein the sensor data is associated with a glucose concentration of a host; processing the sensor data; generating a medicament therapy; and injecting an amount of medicament into the host based at least in part on the generated medicament therapy.

In an embodiment of the third aspect, the step of generating a medicament therapy comprises determining at least one of an amount of medicament to be delivered and a time of medicament delivery.

In an embodiment of the third aspect, the step of injecting comprises setting the amount of medicament.

In an embodiment of the third aspect, the step of setting the amount of medicament comprises setting a medicament injection rate.

In an embodiment of the third aspect, the step of setting the amount of medicament comprises remotely setting the amount of medicament.

In a fourth aspect, an integrated system for monitoring and treating diabetes is provided, the system comprising: a sensor, the sensor comprising a continuous glucose sensor configured to continuously detect a signal associated with a glucose concentration of a host, a processor module configured and arranged to process the signal to generate a therapy, and a communication module configured and arranged to communicate the therapy instruction to a medicament delivery device; and at least one medicament delivery device configured and arranged to deliver a medicament therapy to the host based at least in part on the communicated therapy instruction.

In an embodiment of the fourth aspect, the medicament therapy comprises at least one of a medicament type, a medicament amount, and a delivery time.

In an embodiment of the fourth aspect, the sensor further comprises an input module configured to receive host information, and wherein the processor module is further configured to process the host information.

In an embodiment of the fourth aspect, the input module is configured to receive information from at least one of a user interface, a medicament delivery device, an infusion pump, a patient monitor, and a single-point glucose monitor.

In an embodiment of the fourth aspect, the integrated system further comprises a display module configured and arranged to display of host information, sensor data, the therapy instruction, an alert and/or an alarm.

In an embodiment of the fourth aspect, the communication module is configured to communication wirelessly with the medicament delivery device.

In an embodiment of the fourth aspect, the communication module is further configured to communicate the therapy instruction responsive to interrogation by the medicament delivery device.

In an embodiment of the fourth aspect, the medicament delivery device is configured for communication with a plurality of sensors.

In an embodiment of the fourth aspect, the medicament delivery device is configured for medicament delivery to a plurality of different hosts, based at least in part on a therapy instruction from a sensor.

In an embodiment of the fourth aspect, the medicament delivery device is a hand-held injector pen.

In an embodiment of the fourth aspect, the medicament delivery device is configured and arranged for aseptic medicament delivery to a plurality of hosts.

In an embodiment of the fourth aspect, at least one of the sensor and delivery device is configured transmit data to a data repository.

In a fifth aspect, a method for monitoring and treating diabetes using an integrated diabetes monitoring and treatment system is provided, the method comprising: continuously detecting a signal associated with a glucose concentration of a host; processing the signal; generating a therapy instruction; communicating the therapy instruction to at least one medicament delivery device; and delivering a medicament therapy to the host based at least in part on the communicated therapy instruction.

In an embodiment of the fifth aspect, the method further comprises receiving and processing host information.

In an embodiment of the fifth aspect, the method further comprises remotely programming the system.

In an embodiment of the fifth aspect, the step of generating the therapy instruction comprises determining at least one of a type of medicament, a medicament amount, and a delivery time.

In an embodiment of the fifth aspect, the method further comprises receiving information from at least one of a user interface, a medicament delivery device, an infusion pump, a patient monitor, and a single-point glucose monitor.

In an embodiment of the fifth aspect, the method further comprises displaying at least one of host information, sensor data, the therapy instruction, an alert, and an alarm.

In an embodiment of the fifth aspect, the step of communicating further comprises communicating wirelessly.

In an embodiment of the fifth aspect, the step of communicating further comprises communicating the therapy instruction based at least in part on interrogation by the medicament delivery device.

In an embodiment of the fifth aspect, the step of communicating further comprises communicating to a medicament delivery device configured for medicament delivery to a plurality of hosts, based at least in part on a therapy instruction communicated by an integrated system worn by each host.

In an embodiment of the fifth aspect, the step of communicating further comprises communicating to a hand-held injector pen.

In an embodiment of the fifth aspect, the step of communicating further comprises communicating to a medicament delivery device configured and arranged for aseptic medicament delivery to a plurality of hosts.

In an embodiment of the fifth aspect, the step of communicating further comprises transmitting data to a data repository.

In a sixth aspect, a medicament delivery device for monitoring and treating at least one of a plurality of hosts is provided, the medicament delivery device comprising: a communication module configured to interrogate a continuous glucose sensor and to receive sensor data therefrom, wherein the sensor data comprises a signal associated with an analyte concentration of a host; a processor module configured to process the sensor data and calculate a medicament therapy, wherein the processor module comprises programming for calculating the medicament therapy based at least in part on the sensor data; and a hand-held injector pen configured and arranged to deliver a medicament to the host, based at least in part on the medicament therapy.

In an embodiment of the sixth aspect, the medicament delivery device further comprises a user interface configured and arranged for at least one of input of at least some medical information and display of at least some medical information, wherein medical information comprises at least one of host information, received sensor data, processed sensor data, the calculated medicament therapy, a delivered medicament therapy, an instruction, an alert, an alarm, and a failsafe.

In an embodiment of the sixth aspect, the user interface is detachably connected to the hand-held injector pen.

In an embodiment of the sixth aspect, host information comprises at least one of a host information, type of medicament to be delivered, a glucose target, predicted hypoglycemia, predicted hypoglycemia, a therapy protocol, an alert, and an alarm.

In an embodiment of the sixth aspect, the processor module is further configured for validation of the medicament therapy.

In an embodiment of the sixth aspect, the medicament therapy comprises at least one of a type of medicament to be delivered, an amount of medicament to be delivered and a time of delivery.

In an embodiment of the sixth aspect, the communication module is further configured to communicate treatment information to a central monitor, wherein the treatment information comprises at least one of host information, sensor data, the medicament therapy, and delivered medicament information.

In an embodiment of the sixth aspect, the communication module is configured for wireless communication.

In an embodiment of the sixth aspect, the wireless communication is selected from the group consisting of RF communication, IR communication, Bluetooth communication, and inductive coupling.

In an embodiment of the sixth aspect, the communication module and the medicament delivery device are integrally formed.

In an embodiment of the sixth aspect, the communication module and the medicament delivery device are detachably connected.

In an embodiment of the sixth aspect, the injector pen is configured for aseptic medicament delivery to a plurality of hosts.

In an embodiment of the sixth aspect, the injector pen is configured and arranged for pneumatic aseptic medicament delivery.

In an embodiment of the sixth aspect, the injector pen comprises a cartridge comprising a plurality of single-use needles.

In an embodiment of the sixth aspect, the cartridge is configured and arranged for automatic installation of a clean needle after a medicament delivery.

In a seventh aspect, a method for monitoring and treating diabetes in one of a plurality of hosts is provided, the method comprising: interrogating a continuous glucose sensor; receiving sensor data from the continuous glucose sensor, wherein the sensor data comprises a signal associated with an analyte concentration of a first host; processing the sensor data; calculating a medicament therapy based at least in part on the sensor data; and delivering an amount of a medicament to the first host, based at least in part on the calculated medicament therapy.

In an embodiment of the seventh aspect, the steps of interrogating, receiving, processing, calculating and delivering are repeated with a second host.

In an embodiment of the seventh aspect, the method further comprises a step of at least one of inputting at least some medical information and displaying at least some medical information, wherein medical information comprises at least one of host information, received sensor data, processed sensor data, the calculated medicament therapy, a delivered medicament therapy, an instruction, an alert, an alarm, and a failsafe.

In an embodiment of the seventh aspect, the method further comprises detachably connecting a user interface.

In an embodiment of the seventh aspect, the method further comprises validating the medicament therapy.

In an embodiment of the seventh aspect, the method further comprises communicating treatment information to a central monitor, wherein the treatment information comprises at least one of host information, sensor data, the medicament therapy, and delivered medicament information.

In an embodiment of the seventh aspect, the step of communicating comprises communicating wirelessly.

In an embodiment of the seventh aspect, the steps of interrogating and receiving comprise communicating wirelessly.

In an embodiment of the seventh aspect, the step of delivering comprises aseptically delivering the medicament to a plurality of hosts.

In an embodiment of the seventh aspect, the step of delivering comprises pneumatically aseptically delivering the medicament.

In an embodiment of the seventh aspect, the step of delivering comprises automatically installing a clean needle after medicament delivery.

In an eighth aspect, an integrated system for monitoring and treating diabetes is provided, the system comprising: a receiver configured and arranged to receive continuous glucose sensor data from a continuous glucose sensor; a processor module configured to process the continuous glucose sensor data and to provide first and second medicament dosing information based at least in part on the continuous glucose sensor data; and a communication module configured and arranged to communicate the medicament dosing information with a first integrated medicament delivery device and a second integrated medicament delivery device.

In an embodiment of the eighth aspect, the first medicament dosing information comprises a basal medicament dose and the first integrated medicament delivery device comprises a basal medicament delivery device.

In an embodiment of the eighth aspect, the basal medicament delivery device comprises a medicament pump configured to infuse a first medicament.

In an embodiment of the eighth aspect, the processor module comprises programming to calculate a basal dose based at least in part on the continuous glucose sensor data.

In an embodiment of the eighth aspect, the second medicament dosing information comprises a bolus medicament dose and the second integrated medicament delivery device comprises a bolus medicament delivery device.

In an embodiment of the eighth aspect, the processor module comprises programming to calculate a bolus dose based at least in part on the continuous glucose sensor data.

In an embodiment of the eighth aspect, the bolus medicament delivery device comprises a hand-held medicament injection pen configured to infuse a second medicament.

In an embodiment of the eighth aspect, the bolus medicament delivery device comprises a motor configured to automatically set the amount of medicament and the medicament dosing information comprises an instruction for the medicament delivery device to automatically portion out the bolus dose, whereby the portioned out bolus dose can be manually delivered by the host.

In an embodiment of the eighth aspect, the bolus medicament delivery device comprises a motor to control a rate of medicament injection into the host.

In an embodiment of the eighth aspect, the integrated system further comprises a user interface configured and arranged to display at least one of continuous glucose sensor data and medicament dosing information.

In an embodiment of the eighth aspect, the user interface is further configured for input of at least one of host information and medicament delivery device information.

In an embodiment of the eighth aspect, the host information comprises at least one of host identity, host physical state, target glucose concentration and type of medicament to be delivered.

In an embodiment of the eighth aspect, the medicament delivery information comprises at least one of host identity, identification of a functionally connected medicament delivery device, a type of medicament to be delivered, a medicament delivery profile, a medicament delivery protocol, and a failsafe.

In an embodiment of the eighth aspect, the communication module comprises a communication module configured and arranged to interrogate and/or provide medicament dosing information to the first medicament delivery device and the second medicament delivery device.

In an embodiment of the eighth aspect, the receiver comprises the communication module and the processor module, and wherein the receiver wirelessly communicates with the first and second medicament delivery devices.

In an embodiment of the eighth aspect, the receiver comprises the communication module and the processor module, and wherein the receiver is physically connected to at least one of the first medicament delivery device and the second medicament delivery device.

In a ninth aspect, a method of self-monitoring and self-treating diabetes is provided, the method comprising: receiving continuous glucose sensor data from an operably connected continuous glucose sensor; processing the continuous glucose sensor data; calculating medicament dosing information for at least two integrated medicament delivery devices based at least in part on the continuous glucose sensor data; and communicating the medicament dosing information with the integrated medicament delivery devices.

In an embodiment of the ninth aspect, the step of calculating medicament dosing information comprises calculating a basal dose based at least in part on the continuous glucose sensor data.

In an embodiment of the ninth aspect, the step of communicating comprises communicating the basal medicament dose to a medicament pump.

In an embodiment of the ninth aspect, the method further comprises infusing the basal medicament dose.

In an embodiment of the ninth aspect, the step of providing medicament dosing information comprises calculating a bolus dose based at least in part on the continuous glucose sensor data.

In an embodiment of the ninth aspect, the step of communicating comprises communicating the bolus medicament dose to a hand-held injector pen.

In an embodiment of the ninth aspect, the step of delivering comprises injecting the bolus medicament dose.

In an embodiment of the ninth aspect, the step of communicating the bolus dose further comprises providing an instruction to automatically set at least one of the amount of medicament and rate of delivery based at least in part on the medicament dosing information.

In an embodiment of the ninth aspect, the step of delivering the bolus dose further comprises automatically setting the amount of medicament based at least in part on the provided instruction.

In an embodiment of the ninth aspect, the step of delivering the bolus dose further comprises automatically setting the rate of delivery based at least in part on the provided instruction.

In an embodiment of the ninth aspect, the method further comprises displaying at least one of continuous glucose sensor data and medicament dosing information.

In an embodiment of the ninth aspect, the method further comprises inputting at least one of host information and medicament delivery device information.

In an embodiment of the ninth aspect, the step of communicating comprises wirelessly communicating.

In an embodiment of the ninth aspect, the step of wirelessly communicating comprises interrogating and/or providing medicament dosing information.

BRIEF DESCRIPTION OF THE DRAWINGS

FIG. 3 is a perspective view of an integrated system in one embodiment, showing an LCD screen on a hand-held medicament injection pen housing.

DETAILED DESCRIPTION OF THE PREFERRED EMBODIMENT

Figure 1:
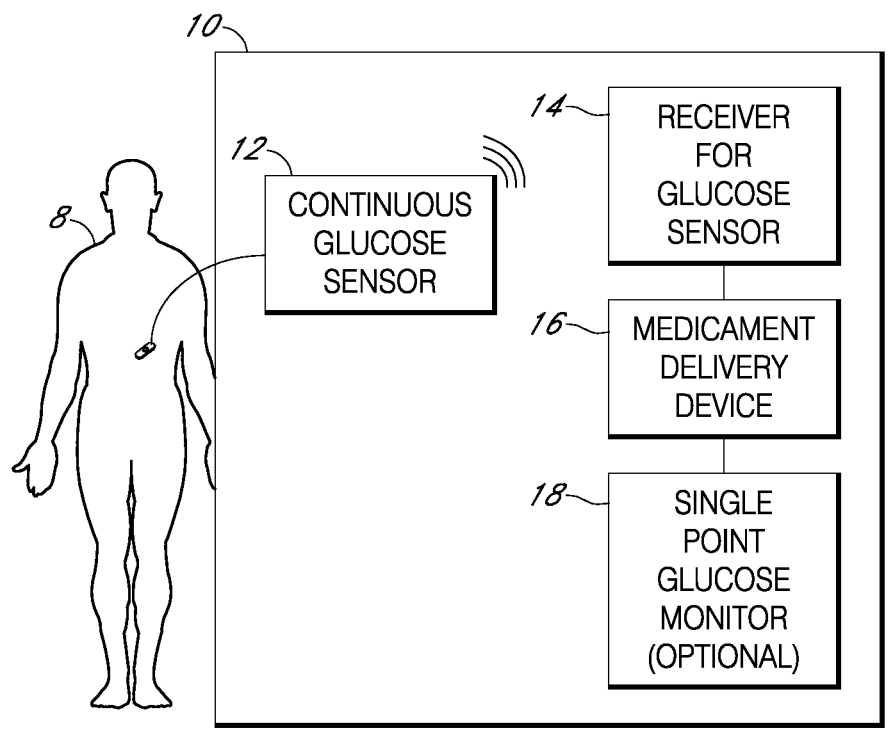
FIG. 1 is a block diagram of an integrated system of the preferred embodiments, including a continuous glucose sensor, a receiver for processing and displaying sensor data, a hand-held medicament injection pen, and an optional single point glucose-monitoring device.

The following description and examples illustrate some exemplary embodiments of the disclosed invention in detail. Those of skill in the art will recognize that there are numerous variations and modifications of this invention that are encompassed by its scope. Accordingly, the description of a certain exemplary embodiment should not be deemed to limit the scope of the present invention.

Definitions

In order to facilitate an understanding of the preferred embodiments, a number of terms are defined below.

The term "algorithm" as used herein is a broad term, and is to be given its ordinary and customary meaning to a person of ordinary skill in the art (and is not to be limited to a special or customized meaning), and refers without limitation to a computational process (for example, programs) involved in transforming information from one state to another, for example, by using computer processing.

The term "basal," as used herein is a broad term, and is to be given its ordinary and customary meaning to a person of ordinary skill in the art (and is not to be limited to a special or customized meaning), and refers without limitation to the minimum required rate or other value for something to function. For example, in the case of medicament therapy, the term "basal rate" can refer to a regular (e.g., in accordance with fixed order or procedure, such as regularly scheduled for/at a fixed time), periodic or continuous delivery of low levels of medicament, such as but not limited to throughout a 24-hour period.

The term "basal profile," as used herein is a broad term, and is to be given its ordinary and customary meaning to a person of ordinary skill in the art (and is not to be limited to a special or customized meaning), and refers without limitation to a medicament delivery schedule that includes one or more blocks of time (e.g., time blocks), wherein each block is associated with a maximum medicament delivery rate.

The term "biological sample" as used herein is a broad term, and is to be given its ordinary and customary meaning to a person of ordinary skill in the art (and is not to be limited to a special or customized meaning), and refers without limitation to sample of a host body, for example blood, interstitial fluid, spinal fluid, saliva, urine, tears, sweat, or the like.

The term "bolus," as used herein is a broad term, and is to be given its ordinary and customary meaning to a person of ordinary skill in the art (and is not to be limited to a special or customized meaning), and refers without limitation to a single dose of medicament, usually given over a short, defined period of time. In one exemplary embodiment, a bolus of medicament is calculated and/or estimated to be sufficient to cover an expected rise in blood glucose, such as the rise that generally occurs during/after a meal.

The term "continuous (or continual) analyte sensing" as used herein is a broad term, and is to be given its ordinary and customary meaning to a person of ordinary skill in the art (and is not to be limited to a special or customized meaning), and refers without limitation to the period in which monitoring of analyte concentration is continuously, continually, and or intermittently (regularly or irregularly) performed, for example, about every 5 to 10 minutes.

The phrase "continuous glucose sensing" as used herein is a broad term, and is to be given its ordinary and customary meaning to a person of ordinary skill in the art (and is not to be limited to a special or customized meaning), and refers without limitation to the period in which monitoring of plasma glucose concentration is continuously or continually performed, for example, at time intervals ranging from fractions of a second up to, for example, 1, 2, or 5 minutes, or longer.

The term "count" as used herein is a broad term, and is to be given its ordinary and customary meaning to a person of ordinary skill in the art (and is not to be limited to a special or customized meaning), and refers without limitation to a unit of measurement of a digital signal. For example, a raw data stream or raw data signal measured in counts is directly related to a voltage (for example, converted by an A/D converter), which is directly related to current from the working electrode.

The term "electrochemically reactive surface" as used herein is a broad term, and is to be given its ordinary and customary meaning to a person of ordinary skill in the art (and is not to be limited to a special or customized meaning), and refers without limitation to the surface of an electrode where an electrochemical reaction takes place. For example, a working electrode measures hydrogen peroxide produced by the enzyme-catalyzed reaction of the analyte detected, which reacts to create an electric current. Glucose analyte can be detected utilizing glucose oxidase, which produces $H_2O_2$ as a byproduct. $H_2O_2$ reacts with the surface of the working electrode, producing two protons ($2H^+$), two electrons ($2e^-$) and one molecule of oxygen ($O_2$), which produces the electronic current being detected.

The term "electronic connection" as used herein is a broad term, and is to be given its ordinary and customary meaning to a person of ordinary skill in the art (and is not to be limited to a special or customized meaning), and refers without limitation to any electronic connection known to those in the art. In one exemplary embodiment, a connection is between the sensing region electrodes and the electronic circuitry of a device that provides electrical communication, such as mechanical (for example, pin and socket) or soldered electronic connections.

The term "host" as used herein is a broad term, and is to be given its ordinary and customary meaning to a person of ordinary skill in the art (and is not to be limited to a special or customized meaning), and refers without limitation to mammals, particularly humans.

The term "host information" as used herein is a broad term, and is to be given its ordinary and customary meaning to a person of ordinary skill in the art (and is not to be limited to a special or customized meaning), and refers without limitation to information related to the host, such as a patient using an integrated system of the preferred embodiments, such as but not limited to a continuous glucose sensor, a medicament delivery device, and/or receiving medicament therapy. In some embodiments, the medicament is insulin or another injectable diabetes medicament, such as but not limited to pramlintide, exenatide, amylin, glucagon, and the like. In some embodiments, host information includes but is not limited to information relating to the host and his/her therapy, such as but not limited to information used to identify the host (e.g., in a clinical setting), such as a host identification number and/or code, host physical characteristics, host health information (e.g., medical conditions, diseases, illnesses), host exercise information, a therapy protocol, such as but not limited to a medicament therapy protocol assigned to the host, including but not limited to one or more types of medicament the host is to receive and/or target glucose concentration(s), an alarm, an alert and/or an instruction.

The term "integrated," as used herein is a broad term, and is to be given its ordinary and customary meaning to a person of ordinary skill in the art (and is not to be limited to a special or customized meaning), and refers without limitation to united, bringing together processes or functions.

The term "interrogate," as used herein is a broad term, and is to be given its ordinary and customary meaning to a person of ordinary skill in the art (and is not to be limited to a special or customized meaning), and refers without limitation to give or send out a signal to (e.g., as a transponder) for triggering an appropriate response to obtain data or information from (a device, database, etc.).

The term "medicament therapy," as used herein is a broad term, and is to be given its ordinary and customary meaning to a person of ordinary skill in the art (and is not to be limited to a special or customized meaning), and refers without limitation to an identity, an amount and/or schedule of a medicament to be delivered to the host. In some embodiments, the medicament is a diabetes-treating medicament formulated for injection, such as but not limited to insulin, pramlintide, exenatide, amylin, glucagon, derivatives thereof, and the like. In other embodiments, the medicament is one for treating another disease and is formulated for injection.

The terms "operatively connected," "operatively linked," "operably connected," and "operably linked" as used herein are broad terms, and are to be given their ordinary and customary meaning to a person of ordinary skill in the art (and are not to be limited to a special or customized meaning), and refer without limitation to one or more components linked to one or more other components. The terms can refer to a mechanical connection, an electrical connection, or a connection that allows transmission of signals between the components (e.g., including a wireless connection). For example, one or more electrodes can be used to detect the amount of analyte in a sample and to convert that information into a signal; the signal can then be transmitted to a circuit. In such an example, the electrode is "operably linked" to the electronic circuitry.

The terms "processor module" and "processor" as used herein are broad terms, and are to be given their ordinary and customary meaning to a person of ordinary skill in the art (and are not to be limited to a special or customized meaning), and refer without limitation to a computer system, state machine, processor, or the like designed to perform arithmetic or logic operations using logic circuitry that responds to and processes the basic instructions that drive a computer. In some embodiments, the term processor includes storage, e.g., ROM and RAM.

The term "range," as used herein is a broad term, and is to be given its ordinary and customary meaning to a person of ordinary skill in the art (and is not to be limited to a special or customized meaning), and refers without limitation to a sequence, series, or scale between limits (e.g., maximum and minimum values). For example, a range of glucose concentrations can include glucose concentrations from 60 mg/dl to 200 mg/dl. In another example, a range of medicament delivery rates can include rates from about 0.01 U/hr to about 40 U/hr. In some embodiments, a range is a single value.

The terms "sensor," "sensing region" as used herein are broad terms, and are to be given their ordinary and customary meaning to a person of ordinary skill in the art (and are not to be limited to a special or customized meaning), and refer without limitation to the component or region of a device by which an analyte can be quantified.

The terms "smoothing" and "filtering" as used herein are broad terms, and are to be given their ordinary and customary meaning to a person of ordinary skill in the art (and are not to be limited to a special or customized meaning), and refer without limitation to modification of a set of data to make it smoother and more continuous or to remove or diminish outlying points, for example, by performing a moving average.

The term "single point glucose monitor" as used herein is a broad term, and is to be given its ordinary and customary meaning to a person of ordinary skill in the art (and is not to be limited to a special or customized meaning), and refers without limitation to a device that can be used to measure a glucose concentration within a host at a single point in time, for example, a finger stick blood glucose meter. It should be understood that single point glucose monitors can measure multiple samples (for example, blood or interstitial fluid); however only one sample is measured at a time and typically requires some user initiation and/or interaction.

The term "target range," as used herein is a broad term, and is to be given its ordinary and customary meaning to a person of ordinary skill in the art (and is not to be limited to a special or customized meaning), and refers without limitation to a range of glucose concentrations within which a host is to try to maintain his blood sugar. In general, a target range is a range of glucose concentrations considered to be euglycemic. Euglycemic glucose concentrations are discussed in detail in the section entitled "Programming and Processing."

The term "therapy instruction," as used herein is a broad term, and is to be given its ordinary and customary meaning to a person of ordinary skill in the art (and is not to be limited to a special or customized meaning), and refers without limitation to an instruction to a medicament delivery device, such as a medicament injection pen or and medicament pump, to deliver a medicament therapy to a host, including but not limited to an amount of medicament to be delivered and/or a time of medicament delivery.

The terms "substantial" and "substantially" as used herein are broad terms, and are to be given their ordinary and customary meaning to a person of ordinary skill in the art (and are not to be limited to a special or customized meaning), and refer without limitation to a sufficient amount that provides a desired function. In some embodiments, the term "substantially" includes an amount greater than 50 percent, an amount greater than 60 percent, an amount greater than 70 percent, an amount greater than 80 percent, and/or an amount greater than 90 percent. In some embodiments, the integrated electronics are configured to display a representation of medicament delivery on the user interface substantially adjacent to substantially time-corresponding sensor data, wherein "substantially adjacent" refers to a location sufficiently near by or close to the relevant data to create an association, for example.

Overview

FIG. 1 is a block diagram of an integrated system 10 of the preferred embodiments, including a continuous glucose sensor 12, a receiver 14 for processing and displaying sensor data, a medicament delivery device 16, and optionally a single point glucose-monitoring device 18. The integrated diabetes management system 10 of the preferred embodiments provides improved convenience and accuracy thus affording a host 8 with improved convenience, functionality, and safety in the care of their disease.

FIG. 1 shows a continuous glucose sensor 12 that measures a concentration of glucose or a substance indicative of the concentration or presence of the glucose. In some embodiments, the glucose sensor 12 is an invasive, minimally invasive, or non-invasive device, for example a subcutaneous, transdermal, or intravascular device, as described elsewhere herein. In some embodiments, the sensor 12 can analyze a plurality of intermittent biological samples. The glucose sensor can use any method of glucose-measurement, including enzymatic, chemical, physical, electrochemical, spectrophotometric, polarimetric, calorimetric, radiometric, or the like. In alternative embodiments, the sensor 12 can be any sensor capable of determining the level of an analyte in the body, for example oxygen, lactase, insulin, hormones, cholesterol, medicaments, viruses, or the like. The glucose sensor 12 uses any known method to provide an output signal indicative of the concentration of the glucose. The output signal is typically a raw data stream that is used to provide a useful value of the measured glucose concentration to a patient or doctor, for example.

A receiver 14 is provided that receives and processes the raw data stream, including calibrating, validating, and displaying meaningful glucose values to a host, such as described in more detail below. Although the receiver is shown as wirelessly communicating with the sensor, the receiver can be physically connected to the sensor and/or sensor electronics and/or housed within the medicament delivery device and/or single point monitor, thereby removing the wireless connection. A medicament delivery device 16 is further provided as a part of the integrated system 10. In some preferred embodiments, the medicament delivery device 16 is a medicament injection pen or jet-type injector for injecting a medicament (e.g., insulin). In some preferred embodiments, the medicament delivery device 16 is a medicament delivery pump, also referred to as an infusion pump, for medicament infusion (e.g., insulin). In some embodiments, both a hand-held medicament injection pen and an infusion pump are used to deliver one or more types of medicament to the host, as described elsewhere herein in greater detail. In some embodiments, an optional single point glucose monitor 18 is further provided as a part of the integrated system 10, for example a self-monitoring blood glucose meter (SMBG), non-invasive glucose meter, or the like, integrated into a receiver housing and/or a medicament delivery device housing.

Conventionally, each of these devices separately provides valuable information and/or services to diabetic patients. Thus, a typical diabetic patient has numerous individual devices, which they track and consider separately. In some cases, the amount of information provided by these individual devices may require complex understanding of the nuances and implications of each device, for example types and amounts of medicament (e.g., insulin) to deliver. Typically, each individual device is a silo of information that functions as well as the data provided therein, therefore when the devices are able to communicate with each other, enhanced functionality and safety can be realized. For example, when a continuous glucose monitor functions alone (for example, without data other than that which was gathered by the device), sudden changes in glucose level are tracked, but may not be fully understood, predicted, preempted, or otherwise considered in the processing of the sensor data; however, when the continuous glucose sensor is provided with information about time, amount, and type of medicament injections, calories consumed, time or day, meal time, or like, more meaningful, accurate and useful glucose estimation, prediction, and other such processing can be provided, such as described in more detail herein. By integrating these devices, the information from each component can be leveraged to increase the intelligence, benefit provided, convenience, safety, and functionality of the continuous glucose sensor and the other integrated components. Therefore, it would be advantageous to provide a device that aids the diabetic patient in integrating these individual devices in the treatment of his/her disease.

Sensor

The preferred embodiments relate to the use of an analyte sensor 12 that measures a concentration of analyte of interest or a substance indicative of the concentration or presence of the analyte. In some embodiments, the sensor is a continuous device, for example a subcutaneous, transdermal (e.g., transcutaneous), or intravascular device. The analyte sensor can use any method of analyte-sensing, including enzymatic, chemical, physical, electrochemical, spectrophotometric, polarimetric, calorimetric, radiometric or the like.

The analyte sensor uses any method, including invasive, minimally invasive, and non-invasive sensing techniques, to provide an output signal indicative of the concentration of the analyte of interest. The output signal, which is associated with the analyte concentration of the host, is typically a raw signal that is used to provide a useful value of the analyte of interest to a user, such as a patient or physician, who can be using the device. Accordingly, appropriate smoothing, calibration, and/or evaluation methods can be applied to the signal and/or system as a whole to provide relevant and acceptable estimated analyte data to the user.

Figure 2A:
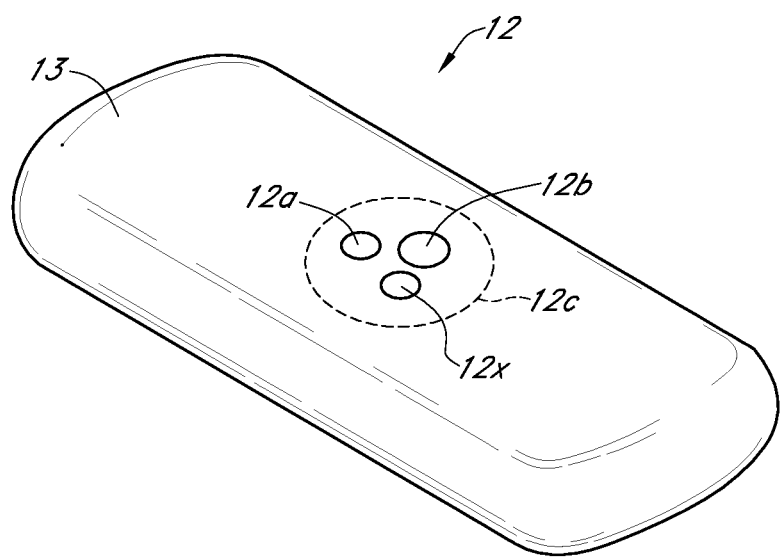
FIG. 2A is a perspective view of a wholly implantable continuous glucose sensor, in one embodiment.

FIG. 2A illustrates the continuous glucose sensor 12, in one embodiment, an implantable glucose sensor such as described in U.S. Patent Publication No. 2005-0245799, which is incorporated by reference in its entirety. In this embodiment, a body 13 and a sensing region include the electrodes and a membrane 12c. Sensor electronics (not shown) are located within the body 13. The three electrodes, including but not limited to a working electrode 12a, a reference electrode 12b, and an auxiliary, counter or second working electrode 12x, within the sensing region are operably connected to the sensor electronics and are covered by a sensing membrane 12c and an optionally biointerface membrane (not shown), which are described elsewhere herein. The body 13 is preferably formed from epoxy molded around the sensor electronics, however the body can be formed from a variety of materials, including metals, ceramics, plastics, or composites thereof U.S. Pat. No. 7,134,999, which is incorporated by reference in its entirety, discloses suitable configurations suitable for the body 13. In one embodiment, the sensing region 12c comprises three electrodes including a platinum working electrode 12a, a platinum counter electrode 12x, and a silver/silver chloride reference electrode 12b, for example. However a variety of electrode materials and configurations can be used with the implantable glucose sensor of the preferred embodiments. The top ends of the electrodes are in contact with an electrolyte phase (not shown), which is a free-flowing fluid phase disposed between the sensing membrane and the electrodes. In one embodiment, a counter electrode 12x is provided to balance the current generated by the species being measured at the working electrode. In the case of a glucose oxidase based glucose sensor, the species being measured at the working electrode is $H_2O_2$. Glucose oxidase catalyzes the conversion of oxygen and glucose to hydrogen peroxide and gluconate according to the following reaction:

$$Glucose+O_2 \rightarrow Gluconate+H_2O_2$$

The change in $H_2O_2$ can be monitored to determine glucose concentration because for each glucose molecule metabolized, there is a proportional change in the product $H_2O_2$. Oxidation of $H_2O_2$ by the working electrode is balanced by reduction of ambient oxygen, enzyme generated $H_2O_2$, or other reducible species at the counter electrode. The $H_2O_2$ produced from the glucose oxidase reaction further reacts at the surface of working electrode and produces two protons ($2H^+$), two electrons ($2e^-$), and one oxygen molecule ($O_2$). In an alternative embodiment, the continuous glucose sensor comprises a continuous glucose sensor such as described with reference to U.S. Pat. No. 6,579,690 to Bonnecaze et al. or U.S. Pat. No. 6,484,046 to Say et al. In another alternative embodiment, the continuous glucose sensor comprises a refillable subcutaneous sensor such as described with reference to U.S. Pat. No. 6,512,939 to Colvin et al. All of the above patents and/or patent applications are incorporated in their entirety herein by reference.

Figure 2C:
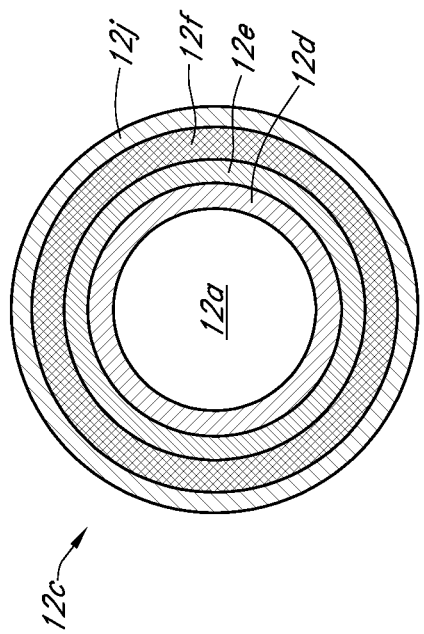
FIG. 2C is a cross-section of the continuous glucose sensor of FIG. 2B, taken on line 2C-2C, in one embodiment.
Figure 2B:
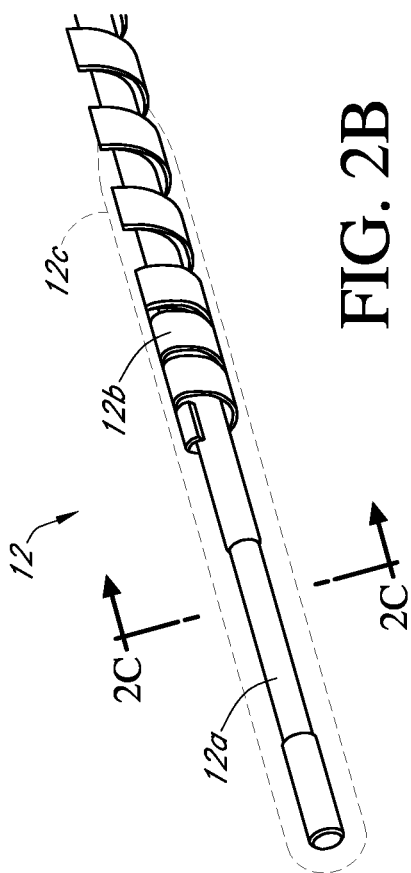
FIG. 2B is a perspective view of an in vivo portion of a continuous glucose sensor, in one embodiment.

FIG. 2B illustrates the continuous glucose sensor in another embodiment; the glucose sensor is described in more detail in U.S. Patent Publication No. US-2006-0020187-A1, U.S. Patent Publication No. US-2006-0142651-A1, U.S. Patent Publication No. US-2006-0270923-A1, U.S. Patent Publication No. US-2007-0027370-A1, U.S. Patent Publication No. US-2005-0143635-A1, U.S. Patent Publication No. US-2007-0027385-A1, U.S. Patent Publication No. US-2007-0213611-A1, and U.S. Patent Publication No. US-2008-0083617-A1, which are each incorporated herein by reference in their entirety. FIG. 2B is a perspective view of an in vivo portion of the continuous glucose sensor 12, in one embodiment. In this embodiment, the in vivo portion of the sensor includes at least one working electrode 12a and a reference electrode 12b and a sensing membrane 12c (dashed line). In one alternative embodiment, the continuous glucose sensor comprises a glucose sensor such as described in U.S. Pat. No. 6,565,509 to Say et al., U.S. Pat. No. 6,360,888 to McIvor et al. and/or U.S. Pat. No. 6,424,847 to Mastrototaro et al. All of the above patents and/or patent applications are incorporated in their entirety herein by reference.

FIG. 2C is a cross-section of the sensor shown in FIG. 2B, taken on line 2C-2C. In preferred embodiments, the membrane 12c (e.g., a biointerface and/or sensing membrane) includes at least an enzyme domain 12f having an enzyme configured to detect the analyte, such as but not limited to glucose oxidase (e.g., GOX). In some preferred embodiments, the sensing membrane 12c can include one or more additional domains, such as but not limited to an electrode domain 12d, an interference domain 12e, a resistance domain 12j, a cell disruptive domain and/or a cell impermeable domain, for example. Additional sensor and membrane configurations can be found in U.S. Patent Publication No. US-2006-0020187-A1, U.S. Patent Publication No. US-2005-0031689-A1, U.S. Patent Publication No. US-2007-0027370-A1, U.S. Patent Publication No. US-2006-0229512-A1, U.S. Patent Publication No. US-2006-0253012-A1, U.S. Patent Publication No. US-2007-0197890-A1, U.S. Patent Publication No. US-2007-0244379, and U.S. Patent Publication No. US-2007-0235331-A1, each of which is incorporated herein by reference in its entirety.

Figure 2D:
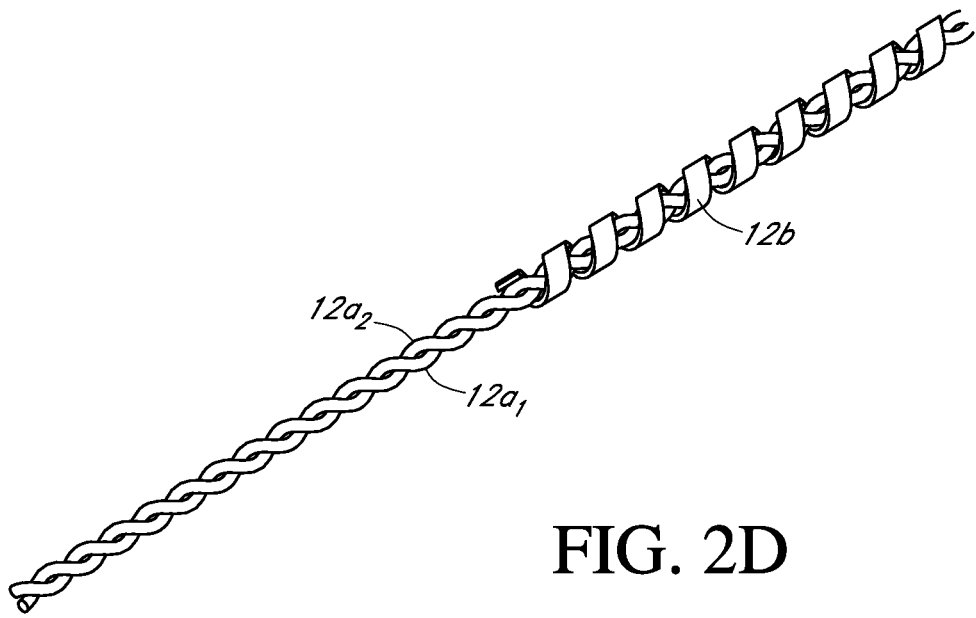
FIG. 2D is a perspective view of an in vivo portion of a continuous glucose sensor including two working electrodes, in one embodiment.

FIG. 2D illustrates the continuous glucose sensor in another embodiment, a glucose sensor having first and second working electrodes (e.g., dual-electrode), such as described in U.S. Patent Publication No. US-2007-0027385-A1, U.S. Patent Publication No. US-2007-0213611-A1, and U.S. Patent Publication No. US-2008-0083617-A1, U.S. Pat. No. 7,366,556, and co-pending U.S. patent application Ser. No. 12/111,062, filed Apr. 28, 2008 and entitled "Dual Electrode System for a Continuous Analyte Sensor," each of which are incorporated herein by reference in their entireties. In some preferred embodiments, the dual-electrode continuous glucose sensor includes a first working electrode $12a_1$ and a second working electrode $12a_2$, and a reference electrode 12b, and a membrane system (not shown), wherein the membrane located over the first working electrode comprises active enzyme and the located over the second working electrode comprises no enzyme or inactive enzyme. Accordingly, a total signal detected by the first working electrode comprises analyte-related (e.g., glucose) and non-analyte-related signal components, while the second working electrode detects a signal comprising only the non-analyte-related signal components. A substantially analyte-only signal can be determined algorithmically, such as, but not limited to, by subtracting the non-analyte-related signal component (detected by the second working electrode) from the total signal (e.g., detected by the first working electrode), thereby providing a substantially "noise-free" analyte signal.

Figure 2E:
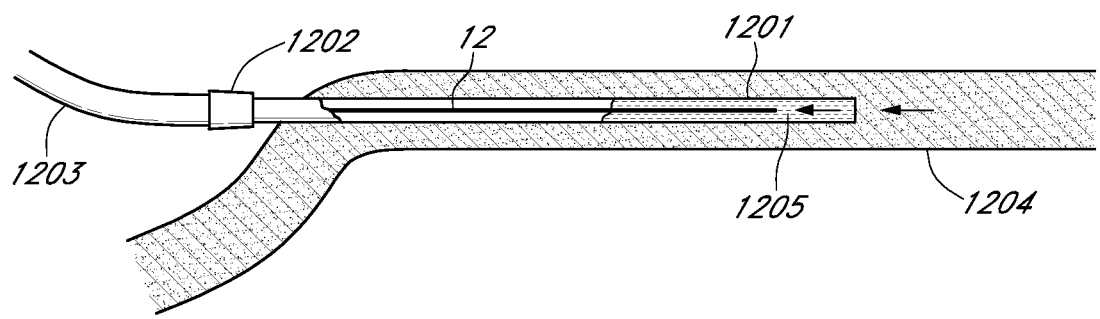
FIG. 2E illustrates a continuous glucose sensor implanted in a vein/artery, in one embodiment.

FIG. 2E illustrates the continuous glucose sensor in yet another embodiment, a continuous glucose sensor configured for implantation into a host's circulatory system, in fluid communication with a host's circulatory system, and/or into an extracorporeal circulatory device. As shown in FIG. 2E, in some embodiments, the continuous glucose sensor 12 is disposed within a catheter 1201 inserted into a vein 1204 or artery of the host. The catheter 1201 is attached to IV tubing 1203 via a connector 1202, such as a Leur lock. In the embodiment illustrated in FIG. 2E, the sensor 12 is exposed to samples of the host's circulatory system (e.g., blood 1205) by withdrawing a blood sample into the catheter lumen such that the sensing portion of the sensor is exposed to the sample. In some alternative embodiments, the sensor 12 is disposed within the fluid connector or other portion of the IV tubing in fluid communication with the host's circulatory system. In this embodiment, after generation of a signal associated with the concentration of glucose in the blood sample, the sample is expelled from the catheter (e.g., back into the circulatory system) and the sensor is washed and calibrated. Additional embodiments are described in greater detail in co-pending U.S. patent application Ser. No. 11/543,396, filed Oct. 4, 2006 and entitled "Analyte Sensor," co-pending U.S. patent application Ser. No. 12/055,114, filed Mar. 25, 2008 and entitled "Analyte Sensor," and U.S. Patent Publication No. US-2008-0108942-A1. In an alternative embodiment, the continuous glucose sensor comprises an intravascular sensor such as described with reference to U.S. Pat. No. 6,477,395 to Schulman et al. In another alternative embodiment, the continuous glucose sensor comprises an intravascular sensor such as described with reference to U.S. Pat. No. 6,424,847 to Mastrototaro et al. All of the above patents and/or patent applications are incorporated in their entirety herein by reference.

The methods and devices of preferred embodiments can be employed in a continuous glucose sensor that measures a concentration of glucose or a substance indicative of a concentration or a presence of glucose. However, certain methods and devices of preferred embodiments are also suitable for use in connection with non-continuous (e.g., single point measurement or finger stick) monitors, such as the One-Touch® system manufactured by LifeScan, Inc., or monitors as disclosed in U.S. Pat. No. 5,418,142; U.S. Pat. No. 5,515,170; U.S. Pat. No. 5,526,120; U.S. Pat. No. 5,922,530; U.S. Pat. No. 5,968,836; and U.S. Pat. No. 6,335,203. In some embodiments, the device can analyze a plurality of intermittent biological samples, such as blood, interstitial fluid, or the like. The glucose sensor can use any method of glucose-measurement, including calorimetric, enzymatic, chemical, physical, electrochemical, spectrophotometric, polarimetric, calorimetric, radiometric, or the like. In alternative embodiments, the sensor can be any sensor capable of determining the level of an analyte in the body, for example oxygen, lactase, hormones, cholesterol, medicaments, viruses, or the like.

Although a few exemplary embodiments of continuous glucose sensors are illustrated and described herein, it should be understood that the disclosed embodiments are applicable to any device capable of single analyte, substantially continual or continuous measurement of a concentration of analyte of interest and providing an output signal that represents the concentration of that analyte.

Medicament Delivery Device

Some preferred embodiments provide an integrated system 10, which includes a medicament delivery device 16 for administering a medicament to a host 8. An integrated medicament delivery device can be designed for bolus injection, continuous injection, inhalation, transdermal absorption, other method for administering medicament, or any combinations thereof. The term medicament includes any substance used in therapy for a host 8 using the system 10, for example, insulin, pramlintide, exenatide, amylin, glucagon, derivatives thereof, and the like. PCT International Publication No. WO02/43566 describes glucose, glucagon, and vitamins A, C, or D that can be used with the preferred embodiments. U.S. Pat. No. 6,051,551 and U.S. Pat. No. 6,024,090 describe types of insulin suitable for inhalation that can be used with the preferred embodiments. U.S. Pat. No. 5,234,906, U.S. Pat. No. 6,319,893, and European Pat. No. 760677 describe various derivatives of glucagon that can be used with the preferred embodiments. U.S. Pat. No. 6,653,332 describes a combination therapy that can be used with the preferred embodiments. U.S. Pat. No. 6,471,689 and PCT International Publication No. WO81/01794 describe insulins useful for delivery pumps that can be used with the preferred embodiments. U.S. Pat. No. 5,226,895 describes a method of providing more than one type of insulin that can be used with the preferred embodiments. All of the above patents and publications are incorporated herein by reference in their entirety and can be useful as the medicament(s) in the preferred embodiments.

In some embodiments, the medicament delivery device is configured for injection and/or infusion of the medicament. For example, in some embodiments, a medicament delivery device is an infusion pump, such as but not limited to a bedside or a portable infusion pump. In one embodiment, the infusion is a portable medicament pump, as described elsewhere herein. In one preferred embodiment, the medicament delivery device 16 is a medicament pump designed for basal and/or bolus infusion of medicament. The medicament pump of the preferred embodiments includes any portable or bedside (e.g., non-portable) infusion devices, such as is appreciated by one skilled in the art. A few examples of medicament infusion devices (e.g., pumps) that can be used with the preferred embodiments include U.S. Pat. No. 5,389,078, U.S. Pat. No. 6,471,689, U.S. Pat. No. 6,656,148, U.S. Pat. No. 6,749,587, U.S. Pat. No. 6,999,854, U.S. Pat. No. 7,060,059, U.S. Pat. No. 7,109,878, U.S. Pat. No. 7,267,665, U.S. Pat. No. 7,291,133, U.S. Pat. No. 7,311,691, U.S. Pat. No. 7,374,556 U.S. Pat. No. 7,303,549, PCT International Publication No. WO 81/01794, European Patent No. 1281351 and co-pending U.S. patent application Ser. No. 12/055,114, filed Mar. 25, 3008 and entitled "Analyte Sensor," all of which are incorporated herein by reference in their entirety.

In some embodiments, a medicament delivery device 16 is a hand-held medicament injection pen, such as but not limited to a syringe, medicament injection pen or a pneumatic injection device. In some embodiments, the hand-held medicament injection pen is configured for single-use (e.g., disposed of after use). In other embodiments, the hand-held medicament injection pen is a multi-use injection device having single-use, disposable parts. For example, a medicament injection pen can be configured to use single-use, disposable needles that are thrown away after one use. In one exemplary embodiment, the medicament injection pen is configured for use with a cartridge of a plurality of single-use, disposable needles, such that each used needle can be changed and/or removed, such as but not limited to by ejecting a used needle and installing an unused (e.g., sterile) needle. In still other embodiments, the hand-held medicament injection pen is a multi-use device configured to sequentially deliver (e.g., aseptically) medicament doses to each of a plurality of hosts. For example, in one embodiment, the hand-held medicament injection pen is a pneumatic injection device.

In one preferred embodiment, the integrated medicament delivery device 16 is a hand-held medicament injection pen (e.g., insulin pen) designed for bolus injection. The hand-held medicament injection pen of the preferred embodiments includes any pen-type injector, such as is appreciated by one skilled in the art. A few examples of a hand-held medicament injection pens that can be used with the preferred embodiments include U.S. Pat. No. 4,865,591, U.S. Pat. No. 5,104,380, U.S. Pat. No. 5,226,895, U.S. Pat. No. 5,308,340, U.S. Pat. No. 5,383,865, U.S. Pat. No. 5,536,249, U.S. Pat. No. 6,192,891, U.S. Pat. No. 7,169,132, U.S. Pat. No. 7,195,616, U.S. Pat. No. 7,291,132, U.S. Patent Publication No. US-2001-0051792-A1, U.S. Patent Publication No. US-2007-0061674-A1 and U.S. Patent Publication No. US-2008-0015511-A1, each of which is incorporated herein by reference in their entirety.

In some embodiments, a medicament delivery device (e.g., hand-held medicament injection pen) is provided, which includes a processor and a wired or wireless connection to a receiver, which are described in more detail elsewhere herein. In some embodiments, the device includes programming that receives instructions from the receiver 14 regarding type and amount of medicament to administer. In some embodiments, wherein the medicament delivery device is an injection device (e.g., a pen) that includes more than one type of medicament, the receiver provides the necessary instructions to determine which type or types of medicament to administer, and can provide instructions necessary for mixing the one or more medicaments. In some embodiments, the receiver provides the glucose trend information (for example, concentration, rate-of-change, acceleration, or other user input information) and the injection device includes programming necessary to determine appropriate medicament delivery. In some embodiments, the receiver, user interface, and/or integrated electronics are incorporated into and/or integral with the pen. However, any of the electronics (including hardware, firmware and/or software/programming) associated with the receiver, medicament delivery device and/or optional single point monitor can be located in any one or a combination of the receiver, medicament delivery device and/or optional single point monitor.

In some embodiments, the receiver and/or hand-held medicament injection pen is configured to calculate medicament usage and/or a remaining on-board medicament amount. In some embodiments, the integrated electronics (e.g., in the receiver and/or medicament delivery device) are configured to receive sensor data and calculate an amount of time remaining with the current medicament on-board the delivery device (e.g., the amount of medicament within the medicament device's reservoir/cartridge) based on historic, current, estimated, and/or predicted glucose data. In some embodiments, integrated electronics include electronics associated with a receiver and a pen, which can be configured for two-way communication there between, such as described in more detail elsewhere herein.

In some embodiments, the pen includes programming to send information regarding the amount, type, and time of medicament delivery administered to the receiver 14 for processing. The receiver 14 can use this information received from the pen, in combination with the continuous glucose data obtained from the sensor, to monitor and determine the host's glucose patterns, such as to measure his response to each medicament delivery. Knowing the host's individual response to each type and amount of medicament delivery can be useful in adjusting or optimizing the host's therapy. It is noted that individual metabolic profiles (for example, medicament sensitivity) are variable from host to host and time to time. While not wishing to be bound by theory, it is believed that once the receiver has learned (or as the receiver continuously learns) the individual's metabolic patterns, including glucose trends and associated medicament deliveries, the receiver can be programmed to adjust and optimize the therapy recommendations for the host's individual physiology to maintain their glucose levels within a desired target range. In some embodiments, the receiver (including user interface and integrated electronics) is integral with and/or incorporated into the pen.

In some embodiments, the receiver includes algorithms that use parameters provided by the continuous glucose sensor, such as glucose concentration, rate-of-change of the glucose concentration, and acceleration of the glucose concentration to more particularly determine the type, amount, and time of medicament administration, can be applied to the integrated system 10, such as described herein. However, the integrated system additionally provides convenience by automation (for example, data transfer through operable connection) and reduced opportunity for human error than may be experienced with the conventional therapy.

In some embodiments, integrated electronics, which are described in more detail elsewhere herein, include programming that requires at least one of the receiver 14, the single point glucose monitor 18, and the hand-held medicament injection pen 16 to be validated or confirmed by another of the components to provide a fail safe accuracy check; in these embodiments, the validation includes algorithms programmed into any one or more of the components. In some embodiments, the integrated electronics include programming that requires at least one of the receiver 14 and the hand-held medicament injection pen 16 (e.g., hand-held medicament injection pen such as a pen) to be validated or confirmed by a human (for example, to confirm the amount and/or type of medicament). In these embodiments, validation provides a means by which the receiver can be used adjunctively, when the host or doctor would like to have more control over the host's therapy decisions, for example. See FIGS. 15 and 16 for exemplary processes that can be implemented herein.

In some embodiments, the hand-held medicament injection pen 16 includes a motor configured for electronic control of at least a portion of the hand-held medicament injection pen. In some embodiments, a motor is configured to automatically set an amount of medicament to be delivered to the host, such as but not limited to a medicament bolus amount, for example, using a step motor. In some embodiments, a motor is configured to control a rate of medicament injection into the host. In some embodiments, the integrated electronics (e.g., the receiver), described in more detail elsewhere herein, are configured to remotely control at least one motor, such as those described above. In some embodiments, the integrated electronics are configured to provide a recommended therapy amount (e.g., medicament bolus amount), which can be communicated to the hand-held medicament injection pen (or which can be integral with the pen); in some such embodiments, the integrated electronics and/or hand-held medicament injection pen electronics are configured to automatically set the bolus amount using the motor (e.g., a step motor), however, in some embodiments, a validation step can be required. In some embodiments, the integrated electronics and/or the hand-held medicament injection pen electronics are configured to automatically inject the medicament at a controlled speed and/or rate. Preferably, the system is configured to inject the medicament at an optimum rate to reduce tissue damage and optimize the medicament absorption, which are believed to enable the effectiveness of the medicament to be more consistent over time. In some embodiments, actuation (or control) of setting a bolus amount(s) and/or injection of the medicament is controlled by a receiver operably connected to the hand-held medicament injection pen, for example by actuation (or selection) of a button, a user selectable menu item, or on a touch screen. In alternative embodiments, actuation (or control) of setting a bolus amount(s) and/or injection of the medicament is controlled by the hand-held medicament injection pen, for example by actuation (or selection) of a button, a user selectable menu item, or on a touch screen.

Although much of this description and the exemplary embodiments are drawn to an integrated hand-held medicament injection pen, the integration concepts described herein are applicable to a variety of other medicament devices, including inhalation devices, transdermal patches, and the like.

Receiver

The preferred embodiments provide an integrated system 10, which includes a receiver 14 that receives and processes the raw data stream from the continuous glucose sensor 12. The receiver can perform all or some of the following operations: a calibration, converting sensor data, updating the calibration, evaluating received reference and sensor data, evaluating the calibration for the analyte sensor, validating received reference and sensor data, displaying a meaningful glucose value to a user, calculating therapy recommendations, validating recommended therapy, adaptive programming for learning individual metabolic patterns, and prediction of glucose values, for example. Some complementary systems and methods associated with the receiver are described in more detail with reference to co-pending U.S. Patent Publication No. US-2005-0027463-A1, which is incorporated herein by reference in its entirety.

In some embodiments, the receiver 14 is a PDA- or pager-sized housing, for example, and comprises a user interface 96 that has a plurality of buttons 108 and a liquid crystal display (LCD) screen, which can include a backlight. In some embodiments, the receiver can take other forms, for example a hand-held medicament injection pen case, a hand-held medicament injection pen kit, a hand-held medicament injection pen housing, a medicament delivery device housing and/or receiver, a computer, a server, a cell phone, a personal digital assistant (PDA), or other such device capable of receiving and processing the data such as described herein. Additionally or alternatively, the user interface can include a keyboard, a speaker, a scroll wheel, and/or a vibrator such as described with reference to FIG. 13. The receiver 14 comprises systems (for example, electronics) necessary to receive, process, and display sensor data from the glucose sensor 12, such as described in more detail with reference to FIG. 13. The receiver 14 processes data from the continuous glucose sensor 12 and additionally processes data associated with at least one of the hand-held medicament injection pen 16, a single point glucose meter 16, and a host 8 (user).

In some embodiments, the receiver is integral with (physically connected to) the sensor. In some embodiments, the receiver 14 is integrally formed with a medicament delivery device 16 and/or a single point glucose monitor 18. In some embodiments, the receiver 14, the medicament delivery device 16 and/or a single point glucose monitor 18 are detachably connected, so that one or more of the components can be individually detached and attached at the user's convenience. In some embodiments, the receiver 14, the medicament delivery device 16, and/or a single point glucose monitor 18 are separate from, detachably connectable to, or integral with each other; and one or more of the components are operably connected through a wired or wireless connection, allowing data transfer and thus integration between the components. In some embodiments, the receiver 14 and the medicament delivery device 16 (e.g., a hand-held medicament injection pen) each comprise mutually engaging electrical contacts, which are configured to allow communication between the hand-held medicament injection pen and the receiver. In a further embodiment, the integrated system is configured to initiate communication between the receiver and the hand-held medicament injection pen, in response to engagement of the electrical contacts. Upon engagement of the electrical contacts, the system is configured to communicate medicament delivery data between the receiver and the hand-held medicament injection pen.

In some embodiments, the receiver 14 includes a housing and a user interface 196 located on the receiver housing. In some embodiments, a hand-held medicament injection pen is provided and includes a housing, wherein the user interface 196 is located on the hand-held medicament injection pen housing. In some embodiments, a housing is provided, wherein the housing is configured to receive a hand-held medicament injection pen and wherein the housing includes a user interface 196. In some embodiments, a hand-held medicament injection pen kit is provided, wherein the hand-held medicament injection pen kit is configured to receive the hand-held medicament injection pen (and can be configured to receive other accessories, such as medicament cartridges, needles, and the like), wherein the user interface 196 is located on the hand-held medicament injection pen kit. In some embodiments, a receiver, integrated electronics, and a hand-held medicament injection pen are integrally formed into one housing.

In some alternative embodiments, a flexible LED screen is provided as a user interface (or a component thereof), wherein the flexible LED screen is physically located on at least one of the receiver and the hand-held medicament injection pen and/or operably connected to at least one of the receiver and the hand-held medicament injection pen, and wherein the integrated electronics are configured to display sensor data on the flexible LED screen.

In some alternative embodiments, an image projection system is provided, wherein the integrated electronics are configured to project data onto a surface (e.g., wall, skin, and the like) as a user interface (or a component thereof). For example, the image projection system can be provided on the receiver, hand-held medicament injection pen, and/or any housing associated therewith, wherein the image projection system is configured to project an image such as alphanumeric data, icons, pictures, and the like, similar to that conventionally seen on an LCD screen, for example. In use, the image can be projected automatically or in response to actuation by a user, wherein the image includes data such as glucose concentration and/or glucose trend, therapy recommendations, event markers, and the like.

Single Point Glucose Monitor

In some embodiments, the integrated system is configured and arrange for operable communication with a single point glucose monitor 18, such as but not limited to a meter for measuring glucose within a biological sample, including a sensing region that has a sensing membrane impregnated with an enzyme, similar to the sensing membrane described with reference to U.S. Pat. No. 4,994,167 and U.S. Pat. No. 4,757,022, which are incorporated herein in their entirety by reference. In some embodiments, the single point glucose monitor includes a conventional finger stick device. However, in alternative embodiments, the single point glucose monitor can use other measurement techniques including enzymatic, chemical, physical, electrochemical, spectrophotometric, polarimetric, calorimetric, radiometric, and the like. In some embodiments, the single point glucose monitor is configured for wired or wireless communication with a component of the integrated system (e.g., automatic and/or semi-automatic communication), such as but not limited to the receiver. However, in other embodiments, the single point glucose monitor is not configured for operable communication with the integrated system, such that the host must manually input the single point glucose monitor data (e.g., into the receiver). It is noted that the meter is optional in that a separate meter can be used and the glucose data downloaded or input by a user into the receiver.

Integrated System Design

In preferred embodiments, an integrated system 10 includes a receiver 14 (e.g., including user interface and integrated electronics), a medicament delivery device 16, and optionally a single point glucose meter 18, wherein the integrated electronics are configured to process and display continuous glucose data from a continuous glucose sensor 12, including trend graphs, glucose concentration, rate of change information (e.g., directional arrow(s)), high and low glucose alarms, and/or the like, on the user interface. In some embodiments, the integrated electronics are configured to process and display information from the medicament delivery device (e.g., hand-held medicament injection pen). The user interface and integrated electronics can be included in and/or on the hand-held medicament injection pen, a hand-held medicament injection pen kit, the receiver, housings associated therewith, and/or combinations thereof.

In some embodiments, an integrated hand-held medicament injection pen kit is provided, including for example, a case configured to hold a hand-held medicament injection pen, one or more medicament cartridges, one or more needles, etc., as is appreciated by one skilled in the art. In some embodiments, the integrated hand-held medicament injection pen kit additionally includes a user interface (e.g., an LCD screen), for example on an outside (or an inside) of the case, configured to display continuous glucose data such as described elsewhere herein. In these embodiments, the kit includes electronics, operatively connected to the user interface, including programming configured to perform all or some of the following operations: calibrating and displaying the continuous glucose sensor data, calculating therapy recommendations (e.g., using a bolus-type calculator), validating (e.g., by a user) recommended therapy, and adaptive algorithms configured for learning individual metabolic patterns (e.g., response to therapies administered by the pen), for example.

FIG. 3 is a perspective view of an integrated system 20 in one embodiment, showing an LCD screen 106 on a hand-held medicament injection pen housing 22. In this exemplary embodiment, the hand-held medicament injection pen 20 includes a hand-held medicament injection pen housing 22, a receiver, integrated electronics, and an LCD screen 106, all of which are integrally formed therewith and/or incorporated therein. The hand-held medicament injection pen housing 22 further includes a port 24 configured to receive medicament cartridges and/or needles, and which an end cap can cover. The LCD screen 106 is configured to display data from the continuous glucose sensor and/or the hand-held medicament injection pen, as described in more detail elsewhere herein. An ergonomic handhold includes indentations 26 configured to allow a user's fingers to rest or hold during actuation of the hand-held medicament injection pen via insertion button 28, for example. While not shown, in some embodiments, sensor and/or medicament delivery electronics can be located partially or wholly with the receiver, with the sensor and/or with the medicament delivery device(s). In some embodiments, the electronics are distributed between the receiver, the sensor and/or the medicament delivery device(s).

In one exemplary embodiment the integrated system 10 is configured and arranged for monitoring and treating diabetes, and includes a medicament delivery device 16 configured and arranged for injecting an amount of medicament into a host 8 and an integrated receiver 14 configured and arranged to receive sensor data from a continuous glucose sensor 12, wherein the sensor data is indicative of a glucose concentration of the host in vivo wherein the integrated receiver comprises electronics configured and arranged to process the sensor data. In some embodiments, the electronics are further configured to calculate an amount of medicament therapy (e.g., a deliverable medicament dose, such as but not limited to a bolus dose to be delivered to the host) and/or a time of medicament therapy delivery. As is appreciated by one skilled in the art, the integrated electronics can be located entirely within the receiver 14, or one or more portions of the electronics can be located with the continuous glucose sensor 12 and/or the medicament delivery device 16 or combinations thereof. Similarly, in some embodiments, the receiver 14 (including integrated electronics) is a separate unit from the sensor 12 and/or hand-held medicament injection pen 16, while in other embodiments, the receiver (in part or in whole) can be integrated with sensor and/or hand-held medicament injection pen, as is described in greater detail herein. For example, in some embodiments, the integrated receiver includes a housing and the hand-held medicament injection pen is integrally formed with the housing.

In another exemplary embodiment, an integrated system 10 for monitoring and treating diabetes is provided, the system comprising a receiver 14 configured and arranged to receive sensor data from an operably connected continuous glucose sensor 12, wherein the continuous glucose sensor is configured and arranged to generate sensor data associated with a glucose concentration of a host; integrated electronics configured to process the sensor data and to generate a medicament therapy (e.g., insulin therapy, pramlintide therapy, exenatide therapy, combinations thereof), and an integrated hand-held medicament injection pen 16 for injecting an amount of the corresponding medicament into the host based at least in part on the medicament therapy. The medicament therapy includes but is not limited to a medicament identity, an amount of medicament therapy and/or a time of medicament therapy delivery. In some further embodiments, the receiver and the hand-held medicament injection pen are integrally formed. However, in some other further embodiments, the receiver and hand-held medicament injection pen are detachably connectable, as described elsewhere herein.

In a further embodiment of a detachably connectable hand-held medicament injection pen 16 (e.g., an insulin, pramlintide or exenatide pen) and receiver 14 housing, the system 10 is configured to initiate communication between the hand-held medicament injection pen and the receiver in response to (detachable) connection of the hand-held medicament injection pen and the housing. For example, in some embodiments, the hand-held medicament injection pen and the housing can include mutually engaging contacts (e.g., electrical contacts) that mate (e.g., make an electrical connection) when the hand-held medicament injection pen is connected to the housing and initiate communication between the receiver and the hand-held medicament injection pen. Upon initiation of communication, the receiver and the hand-held medicament injection pen can transmit data. For example, an amount of medicament therapy (e.g., calculated by the integrated electronics), such as but not limited to a bolus medicament dose (e.g., an amount and type of medicament to be delivered), and a time of medicament therapy can be communicated to the hand-held medicament injection pen, such that the medicament therapy can be delivered to (e.g., injected into) the host. Similarly, the hand-held medicament injection pen can communicate information to the receiver, such as but not limited the amount of medicament delivered to the host, the time the medicament was delivered, the amount of medicament remaining in the hand-held medicament injection pen to be used, the type of medicament contained in the hand-held medicament injection pen, and the like. In some embodiments, wireless communication between the hand-held medicament injection pen and the receiver can be initiated by engagement of the contacts or by host actuation of a switch, button, or the like. In some embodiments, communication between the hand-held medicament injection pen and the receiver is initiated after connection by actuation of a switch, button or the like, such as by the host or by attachment of the two devices. For example, in one embodiment, when the hand-held medicament injection pen is inserted into the receiver housing, an external surface of the hand-held medicament injection pen comes into an adjacent parallel orientation with respect to an internal surface of the receiver housing, which results in depression of a communication actuation button on the interior of the receiver housing. One skilled in the art can appreciate alternative configurations.

In a further embodiment, the integrated system includes a user interface 196, which is configured an arranged for input of host information and/or output of sensor data and/or medicament delivery data, such as, for example, the LCD screens 106 illustrated in FIGS. 3-12. For example, the user interface can include a keyboard 198, buttons 108 and/or a touch screen for input of host information, selection from menus, and the like. The host information includes any information related to the host and his/her medicament therapy, such as but not limited to a host identification (e.g., host ID code/number), physical characteristics of the host, a type of medicament to be injected into the host, a target blood glucose range/level, a protocol for the medicament therapy assigned to the host, an alert, an alarm, and the like. For example, in an embodiment useful in a clinical setting, a caretaker (e.g., nurse, doctor, physician's assistant) can enter a host's ID number and glucose concentration via the user interface, which enables the integrated electronics to calculate a deliverable medicament dose (e.g., according to the medicament therapy protocol assigned to that host ID number), which in turn enables the nurse to deliver an appropriate bolus medicament dose to the host at the bedside. In some embodiments, when the nurse is within a communication distance of the host and his/her implanted continuous glucose sensor, the receiver is configured to interrogate the sensor for the host information and/or sensor data associated with the host's glucose concentration.

In preferred embodiments, the integrated system is configured and arranged to require validation prior to injection an amount of medicament into the host. For example, in some embodiments, the integrated system can prompt the user (e.g., a caretaker, such as a nurse or doctor, or the host himself) to validate (e.g., verify) via the user interface (e.g., via the speaker 100, vibrator 102 or screen) the host ID, the host's assigned medicament therapy protocol and/or they type of medicament on board the hand-held medicament injection pen. Additionally, the integrated system can display information to the nurse, such as the host ID, sensor data received from the continuous glucose sensor, processed sensor data, medicament delivery data (e.g., data related to a medicament therapy to be delivered to the host), and the like.

Figure 4:
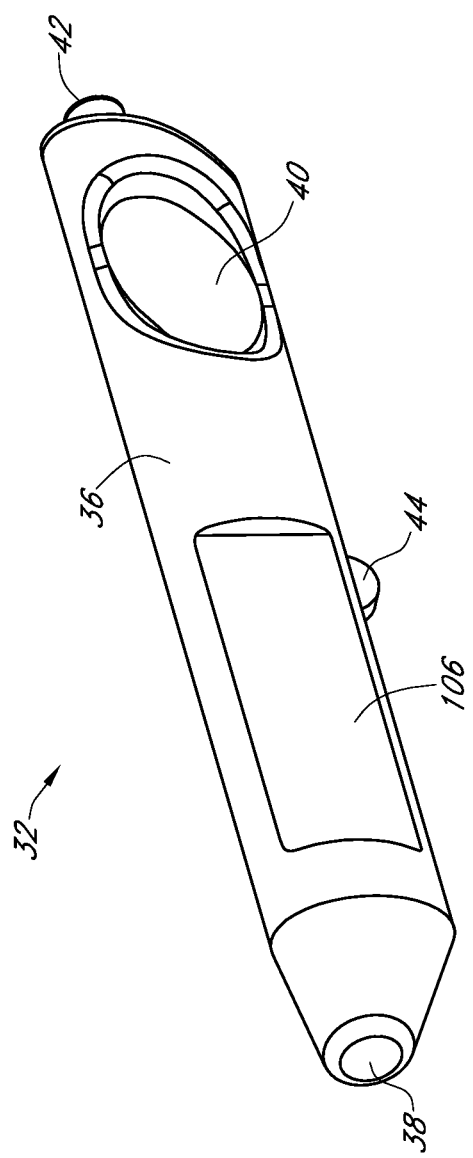
FIG. 4 is a perspective view of an integrated system in another embodiment, showing an LCD screen on a hand-held medicament injection pen housing.

FIG. 4 is a perspective view of an integrated system 32 in another embodiment, showing an LCD screen 106 on a hand-held medicament injection pen housing 36. In this exemplary embodiment, the hand-held medicament injection pen housing 36 includes a hand-held medicament injection pen, a receiver, integrated electronics, and an LCD screen, all of which are integrally formed therewith and/or incorporated therein. The hand-held medicament injection pen housing 36 further includes a port 38 configured to received medicament cartridges and/or needles, and which an end cap can cover. The LCD screen 106 is configured to display data from the continuous glucose sensor and/or the hand-held medicament injection pen, as described in more detail elsewhere herein. An ergonomic handhold includes a thumb hold 40 configured to allow a user's thumb to rest or hold during actuation of the hand-held medicament injection pen via insertion button 42, for example. Additionally, a scroll wheel 44 (also referred to as a jog wheel, thumb wheel, jog encoder, or rotary encoder) is provided that allows for scrolling through menus, data (e.g., numbers), and/or options, for example, and selection of the menus, data and/or options. In one such embodiment, the scroll wheel enables the user to view a variety of menu driven screens or options for initiating a sensor, displaying glucose data, displaying therapy recommendations, modifying therapy recommendations, and the like, by scrolling up or down on the wheel; additionally, the scroll wheel enables the user to select from the screens or options by depressing the scroll wheel. It is believed that incorporation of a scroll wheel into the integrated system enables a more compact system design with good ergonomics, usability, and reliability. In some embodiments, one or more buttons and/or toggles are included (alternatively or in addition to a scroll wheel) for moving through menus, data, options and the like.

Figure 5:
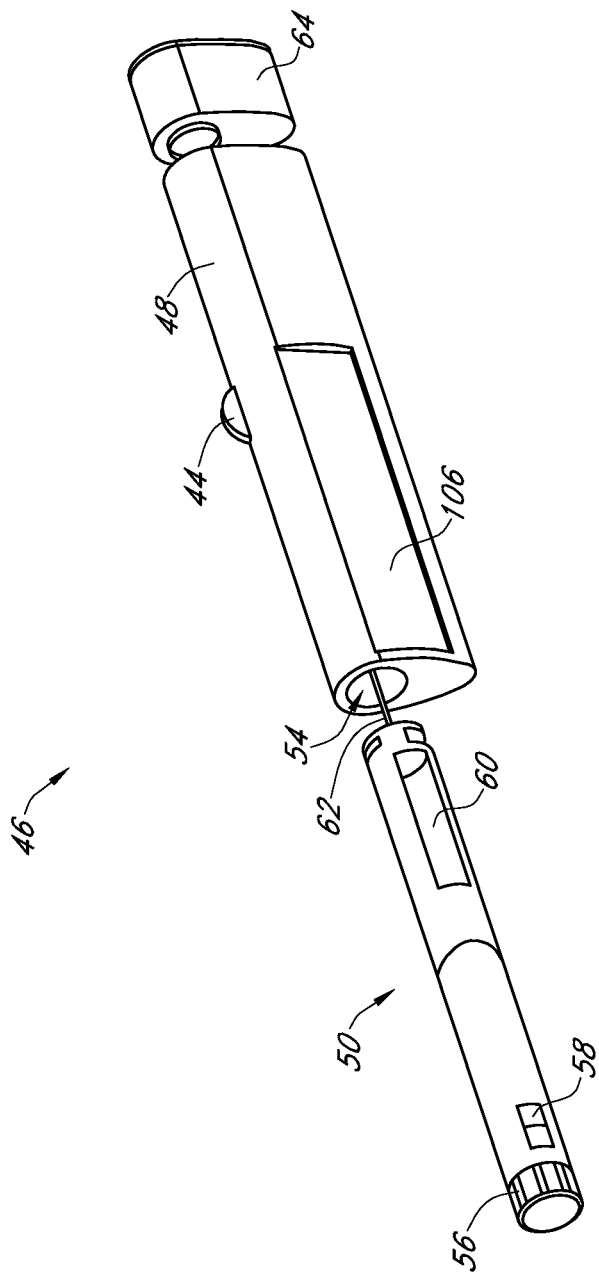
FIG. 5 is a perspective view of an integrated system in another embodiment, showing a housing configured to receive a hand-held medicament injection pen, wherein the housing includes an LCD screen thereon.

FIG. 5 is a perspective view of an integrated system 46 in another embodiment, showing a housing 48 configured to receive a hand-held medicament injection pen 50 wherein the housing includes an LCD screen 106 thereon. In this exemplary embodiment, the housing 48 includes a receiver, integrated electronics, and an LCD screen 106 integrally formed therewith and/or incorporated therein. Additionally, the housing includes an opening 54 configured to receive the hand-held medicament injection pen 50. The illustrated hand-held medicament injection pen shows a dial 56 for setting the medicament bolus amount, a screen 58 for viewing the medicament bolus amount (e.g., from about 0 to about 70 units of medicament in some embodiments) while turning the dial 56, a medicament cartridge holder/receptacle 60 and a needle 62; however, any known hand-held medicament injection pen configured can be used, as is appreciated by one skilled in the art, and as described in more detail elsewhere herein. In some embodiments, the integrated system includes a receptacle configured and arranged to receive and medicament cartridge, thereby medicament can be delivered to the host. In some embodiments, wherein the pen and the housing are separate, the receptacle 60 is included in the hand-held medicament injection pen, as illustrated in FIG. 5. However, in embodiments wherein the pen and the housing are integrally formed, the receptacle can be integrally formed with the housing. The integrated system is configured such that the hand-held medicament injection pen is at least partially received, and can be substantially fully received by the housing 48. In some embodiments, an end cap 64 is provided to protect the end of the hand-held medicament injection pen and/or for with a storage compartment for storing hand-held medicament injection pen accessories (e.g., needles, medicament cartridges, and the like). The illustrated housing 48 includes an LCD screen 106 and a scroll wheel 44, which are described in more detail elsewhere herein.

In some embodiments, such as the embodiment illustrated in FIG. 5, the hand-held medicament injection pen is detachably connectable to the receiver. In some embodiments, wherein integrated system 46 includes a housing configured to receive the hand-held medicament injection pen, mutually engaging contacts are provided on the hand-held medicament injection pen and on the housing (e.g., receiver, case, etc), such that when the pen is received by (detachably connected to) the housing (e.g., in a predetermined position), direct communication between the pen and the housing (e.g., receiver and/or integrated electronics housed therein) can occur. In some embodiments, the integrated system is configured to detect when the pen is received by the housing and subsequently upload and/or download information there between. In some embodiments, the integrated system is configured to initiate communication between the hand-held medicament injection pen and the housing (e.g., receiver and/or integrated electronics) in response to mutual engagement of the electrical contacts. In some embodiments, the integrated system is configured communicate data (e.g., recommended medicament bolus amount, actual amount of medicament delivered, and time of medicament delivery, glucose data, and the like) between the hand-held medicament injection pen and the housing (e.g., receiver and/or integrated electronics) in response to engagement of the electrical contacts.

Figure 6:
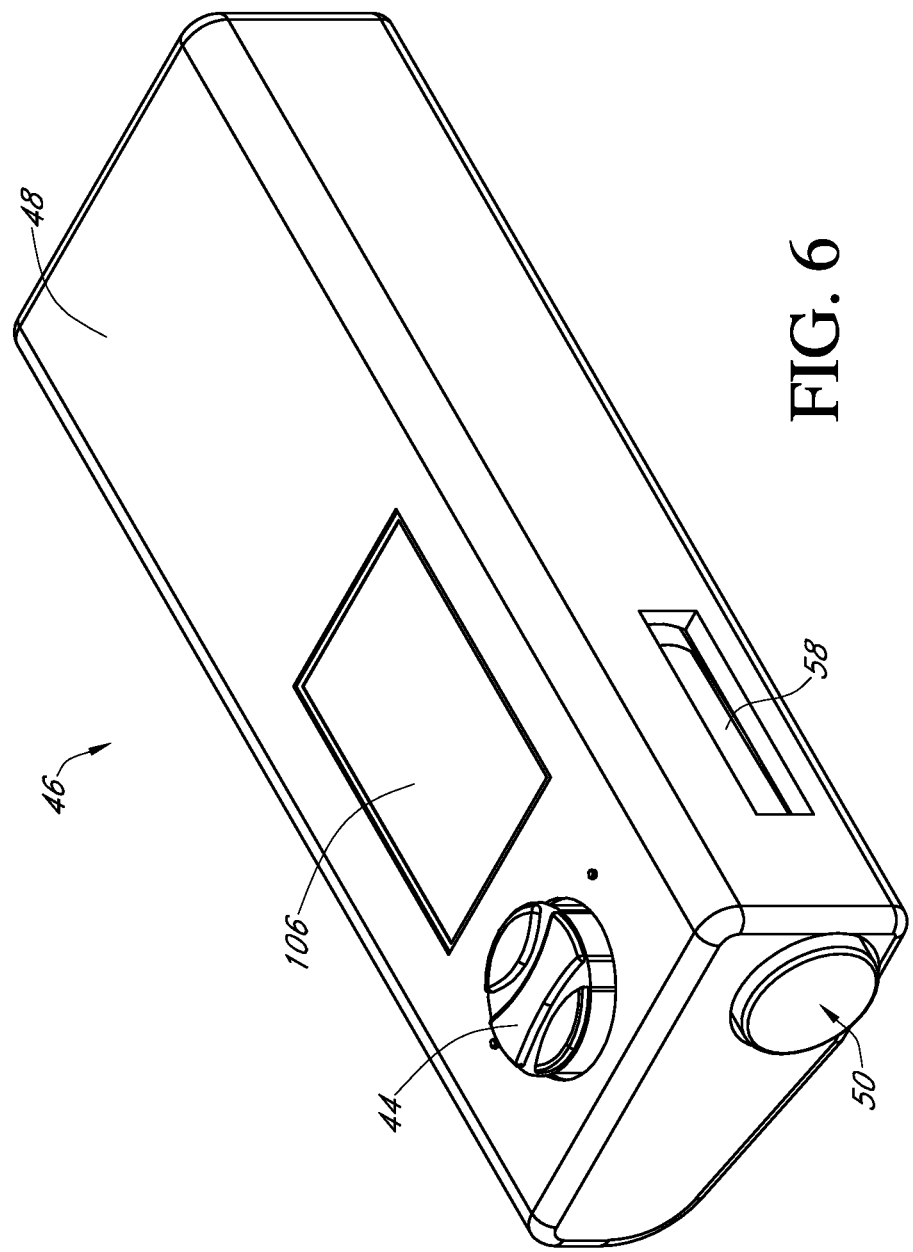
FIG. 6 is a perspective view of an integrated system in another embodiment, showing a housing configured to receive a hand-held medicament injection pen, wherein the housing includes an LCD screen thereon.

FIG. 6 is a perspective view of an integrated system 46 in yet another embodiment, wherein the integrated receiver 14 includes a housing 48 configured to receive a hand-held medicament injection pen 50 wherein the housing includes an LCD screen 106 thereon. In this exemplary embodiment, the housing 48 includes a receiver, integrated electronics, and an LCD screen 106 integrally formed therewith and/or incorporated therein. The illustrated hand-held medicament injection pen 50 shows a screen 58 for viewing the medicament bolus amount, which can be selected using actuation button 44 located on the housing. Actuation button 44 can also be used to toggle/scroll through menus on LCD screen 106. In some embodiments, the hand-held medicament injection pen includes contacts that mate with contacts of the housing, such that the integrated electronics can automatically set a bolus dose, such as a calculated medicament therapy, that can then be manually delivered by the host. Accordingly, in some embodiments, the hand-held medicament injection pen 16 is detachably connectable to the housing. For example, the hand-held medicament injection pen can be connected to the housing and then removed/separated from the housing. For example, in some embodiments, the hand-held medicament injection pen is disposable and a first hand-held medicament injection pen is removed and thrown away, followed by connection of a second (e.g., new, unused) hand-held medicament injection pen. In another example, the hand-held medicament injection pen is not disposable, but uses disposable cartridges of medicament received in a receptacle. Accordingly, in this example, the hand-held medicament injection pen can be disconnected from the housing, for medicament cartridge replacement, followed by reconnection of the pen to the housing.

Figure 7:
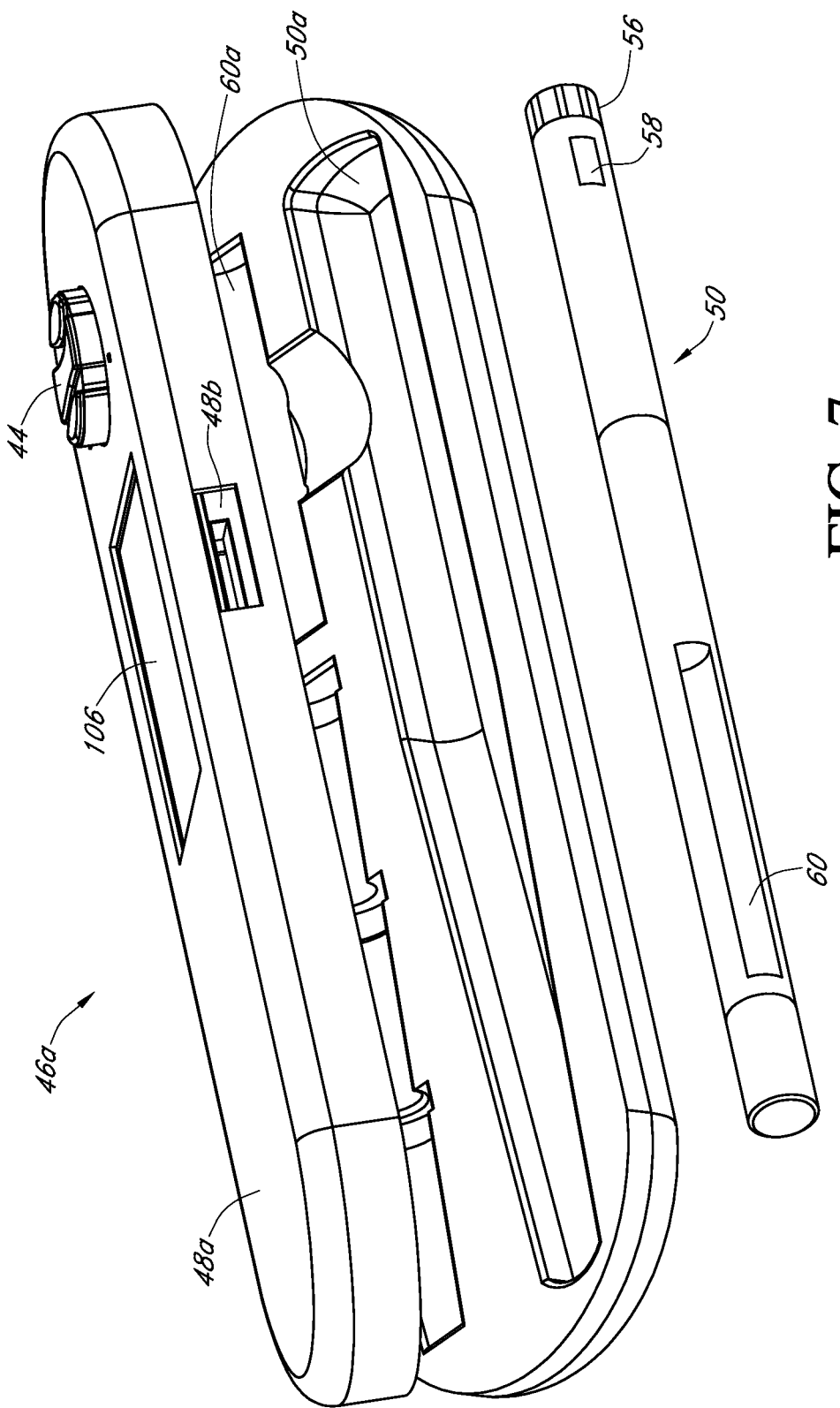
FIG. 7 is a perspective view of an integrated system in another embodiment, showing a housing configured to receive a hand-held medicament injection pen, a receiver, integrated electronics, and a user interface.

FIG. 7 is a perspective view of an integrated system 46a in yet another embodiment, in which the integrated receiver 14 includes a housing 48a, such as but not limited to a hand-held medicament injection pen kit, configured to receive a hand-held medicament injection pen 50, wherein the receiver housing includes an LCD screen 106 and an actuation button 44 thereon. In this exemplary embodiment, the system is configured and arranged as a hand-held medicament injection pen kit having a two-part housing configured to open in a clam-shell manner, with a hinge at one edge. While the device illustrated in FIG. 7 includes top and bottom portions connected by a hinge structure, the device can include more than two portions or the portions can be in different orientations from that depicted in FIG. 7. For example, in some embodiments, the housing has three hingeably-connected portions (e.g., top, middle and bottom). In other embodiments, the portions could open from side to side or from front to back, or any combination thereof. In still other embodiments, a portion of the housing is removably connected (e.g., a battery compartment cover) or is configured to slide/pop out of the housing, such as a drawer.

In the illustrated embodiment (FIG. 7), the receiver housing is configured with a top portion including a user interface 196 (e.g., the LCD screen 106 (e.g., for display of sensor data and/or the medicament therapy) and an actuation button 44) located thereon, and a bottom portion configured with compartments 50a and 60a configured to hold (e.g., store) the hand-held medicament injection pen 50 as well as one or more accessories (e.g., medicament cartridges, needles, alcohol wipes, etc.). In some embodiments, display a representation of medicament delivery on the user interface, wherein the representation of medicament delivery is substantially adjacent to substantially time-corresponding sensor data, such at that described elsewhere with reference to FIG. 14. In some embodiments, the user interface includes a flexible LED screen operably connected to at least one of the receiver and the hand-held medicament injection pen, such as, for example, a fold-out or unrolling flexible screen that can be folded up and/or rolled up for storage when not in use. Accordingly, the integrated electronics are configured to display continuous glucose sensor data on the flexible LED screen. In other embodiments, the user interface includes an image projection system configured to project continuous glucose sensor data onto a surface, such as but not limited to a wall, a table top, a book, and the like.

In some embodiments, such as the illustrated embodiment FIG. 7, the hand-held medicament injection pen is detachably connectable to the receiver housing. For example, the hand-held medicament injection pen and the recess for receiving the hand-held medicament injection pen can include mutually engaging electrical contacts that engage when the hand-held medicament injection pen is put away in the housing. Similarly to the hand-held medicament injection pen, in some embodiments, the receiver is connected to the housing (either detachably or non-detachably). However, in preferred embodiments, the receiver (e.g., including integrated electronics) is integrally formed with the housing. In some embodiments, the system is configured to initiate communication between the hand-held medicament injection pen and the receiver in response to engagement of the mutually engaging electrical contacts (e.g., when the pen is put away in the housing), such that data/information (e.g., the medicament therapy) can be communicated between the receiver and hand-held medicament injection pen. The housing includes the receiver and integrated electronics, as well as a connector 48b, for connection of a power cable (e.g., to re-charge an included battery) and/or a data cable (e.g., for connection to a single-point glucose monitor for calibration and/or for connection to a computer, such as for data transfer and/or battery charging). In some embodiments, the hand-held medicament injection pen (e.g., motorized) and the interior of the housing comprise mutually engaging contacts, whereby, when the pen is installed in the housing and the pen and housing contacts are engaged, the integrated electronics can set a bolus dose (on the pen) to be delivered to the host.

Figure 8:
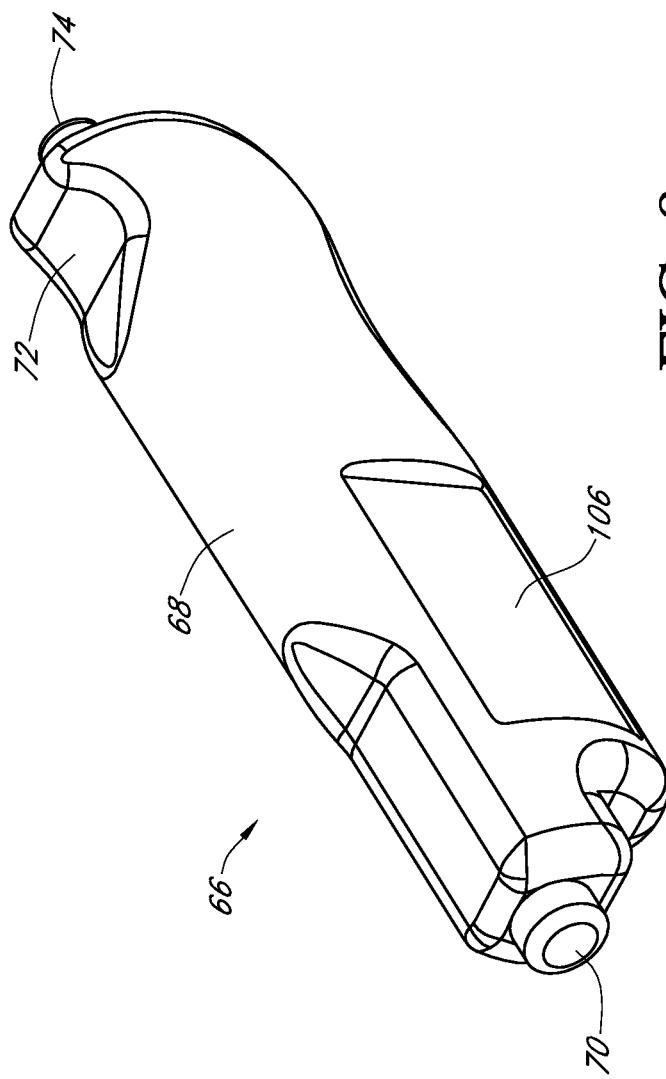
FIG. 8 is a perspective view of an integrated system in another embodiment, showing a hand-held medicament injection pen, a receiver, integrated electronics, and a user interface integrally formed and/or incorporated therein.

FIG. 8 is a perspective view of an integrated system 66 in another embodiment, showing a hand-held medicament injection pen housing 68, a receiver, integrated electronics, a user interface and a hand-held medicament injection pen integrally formed and/or incorporated therein. The hand-held medicament injection pen housing 68 further includes a port 70 configured to received medicament cartridges and/or needles, and which an end cap can cover. The LCD screen 106 is configured to display data from the continuous glucose sensor and/or the hand-held medicament injection pen, as described in more detail elsewhere herein. An ergonomic handhold includes an indentation 72 configured to allow a user's index finger to rest or hold during actuation of the hand-held medicament injection pen via an insertion button 74, for example.

Figure 9:
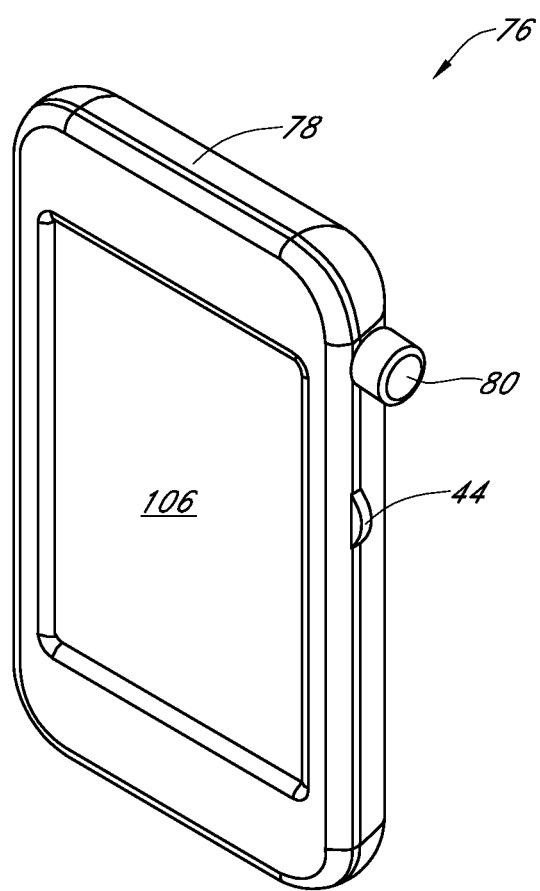
FIG. 9 is a perspective view of an integrated system in another embodiment, showing a receiver housing including a receiver, integrated electronics, a user interface, and a hand-held medicament injection pen integrally formed therewith and/or incorporated therein.

FIG. 9 is a perspective view of an integrated system 76 in another embodiment, showing a receiver housing 78 including a receiver, integrated electronics, a user interface and a hand-held medicament injection pen integrally formed therewith and/or incorporated therein. An actuation button 80 (e.g., for actuation of the hand-held medicament injection pen) is incorporated into the integrated receiver housing; the receiver housing further includes a port on an opposing side (e.g., to the actuation button, not shown in FIG. 9) configured to receive medicament cartridges and/or needles, and which an end cap can cover. In some embodiments, the hand-held medicament injection pen is integrally formed with and/or incorporated into the receiver housing; however, alternative embodiments include an opening in the receiver housing configured to receive a hand-held medicament injection pen similar to that illustrated in FIG. 5 (e.g., such that is detachably connectable thereto). The LCD screen 106 is configured to display data from the continuous glucose sensor and/or the hand-held medicament injection pen, as described in more detail elsewhere herein. The illustrated housing further includes a scroll wheel 44, which is described in more detail elsewhere herein. It is believed that the illustrated configuration of FIG. 9 enables a low profile device, wherein a user can wear or carry the integrated system discretely.

Figure 10:
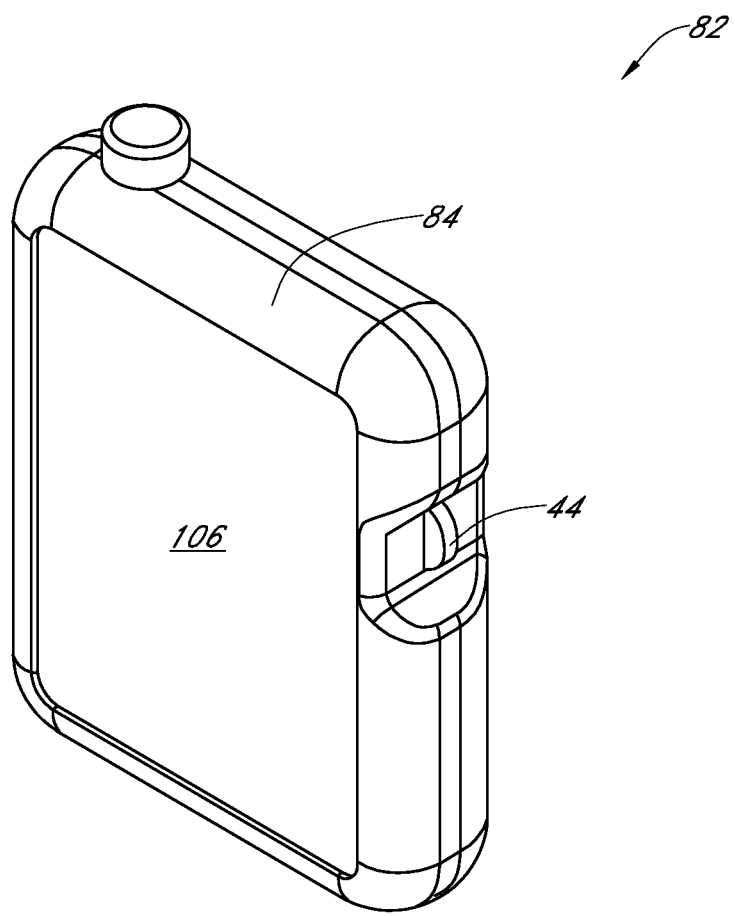
FIG. 10 is a perspective view of an integrated system in another embodiment, showing a receiver housing including a receiver, integrated electronics, a user interface, and a hand-held medicament injection pen integrally formed therewith and/or incorporated therein.

FIG. 10 is a perspective view of an integrated system 82 in another embodiment, showing a receiver housing 84 including a receiver, integrated electronics, a user interface, and a hand-held medicament injection pen integrally formed therewith and/or incorporated therein. The illustrated embodiment of FIG. 10 is substantially similar to FIG. 9; however the integrated hand-held medicament injection pen is rotated 90 degrees within the design of the housing.

Figure 11:
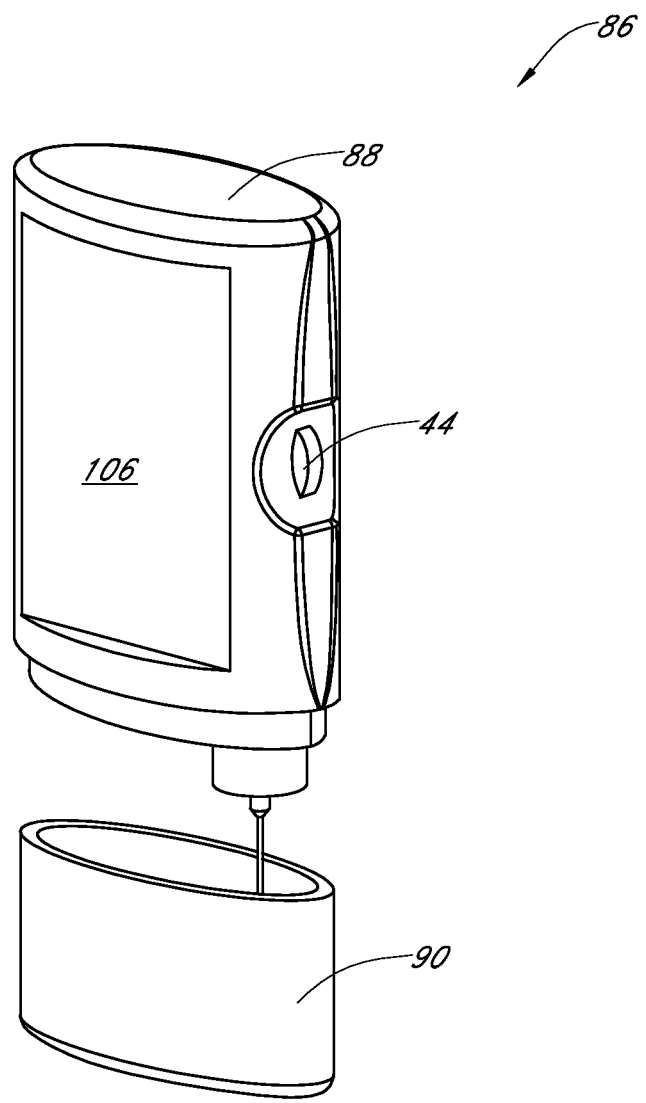
FIG. 11 is a perspective view of an integrated system showing an integrated housing including a receiver, integrated electronics, a user interface, and a hand-held medicament injection pen, wherein the housing further includes a cap for the hand-held medicament injection pen.

FIG. 11 is a perspective view of an integrated system 80 showing an integrated housing 88 including a receiver, integrated electronics, a user interface, and a hand-held medicament injection pen, wherein the housing further includes a cap for the hand-held medicament injection pen. This illustrated embodiment is similar to that of FIGS. 6 and 7, however further includes a cap 90 configured to protect the end of the hand-held medicament injection pen and/or for with a storage compartment for storing hand-held medicament injection pen accessories (e.g., needles, medicament cartridges, and the like).

Figure 12:
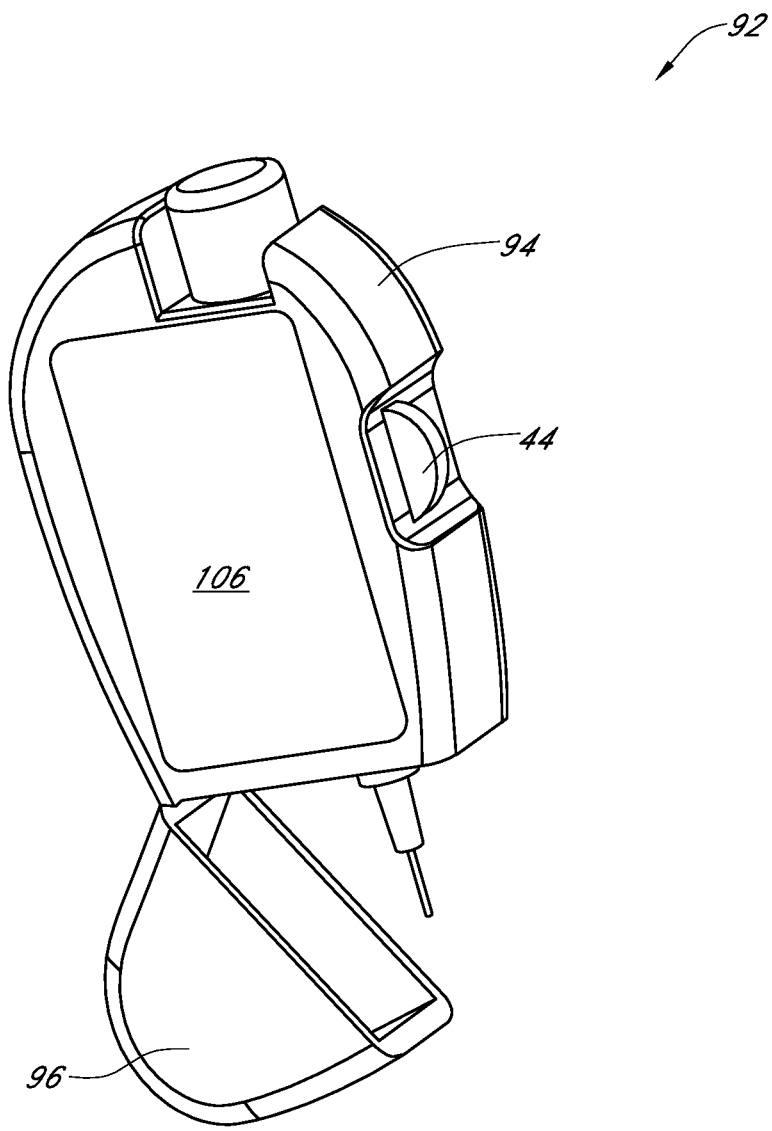
FIG. 12 is a perspective view of an integrated system showing an integrated housing including a receiver, integrated electronics, a user interface, and a hand-held medicament injection pen, wherein the housing further includes a cap.

FIG. 12 is a perspective view of an integrated system 92 showing an integrated housing 94 including a receiver, integrated electronics, a user interface, and a hand-held medicament injection pen, wherein the housing further includes a cap for the hand-held medicament injection pen. This illustrated embodiment is similar to that of FIG. 11, however includes a hinged end cap 96 and can enable a design with a reduced volume/size to encourage patient acceptance and/or use.

Integrated Electronics

Figure 13:
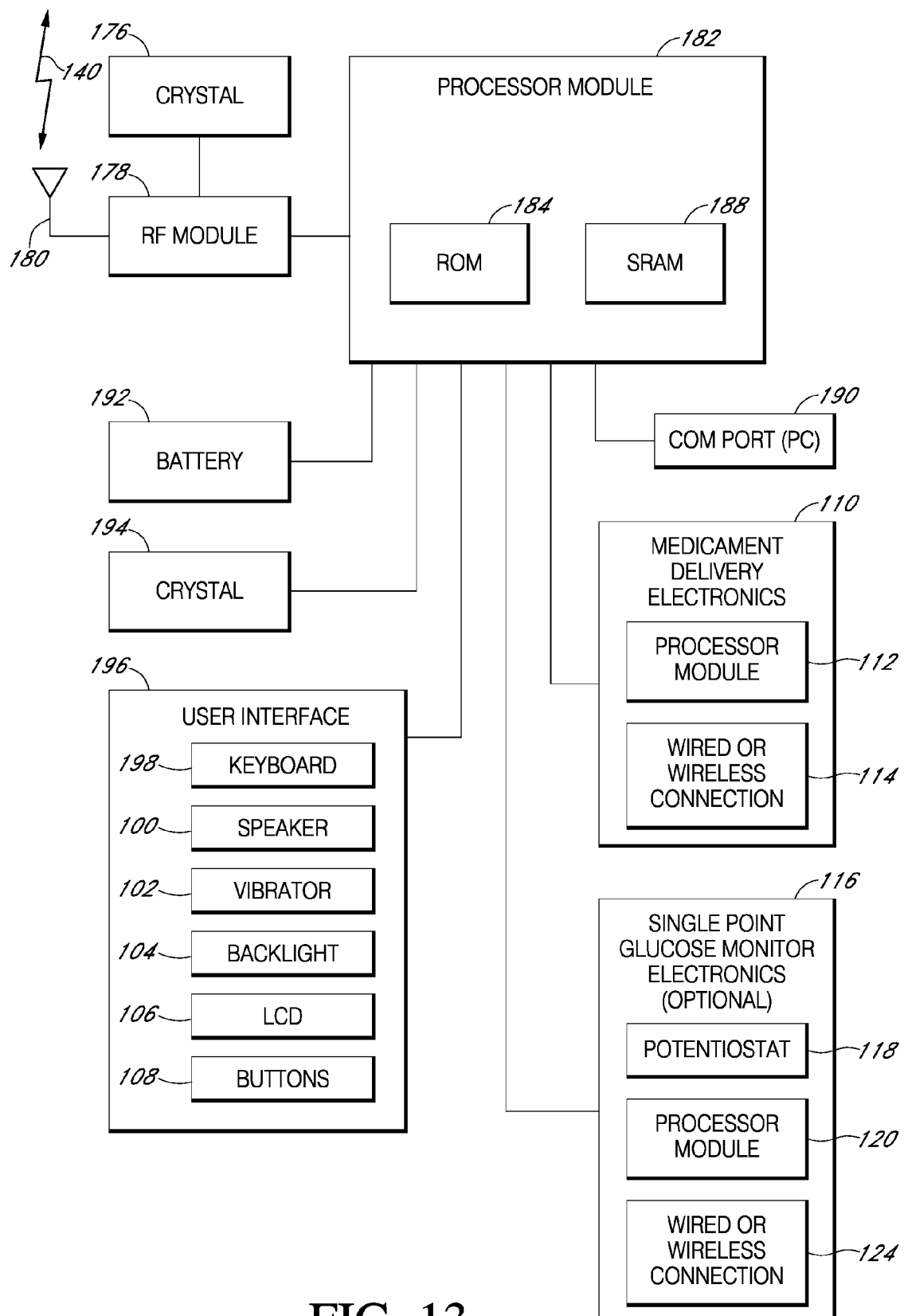
FIG. 13 is a block diagram that illustrates integrated electronics in one embodiment.

FIG. 13 is a block diagram that illustrates integrated system electronics in one embodiment. One embodiment is described wherein the processor within the receiver performs much of the processing, however it is understood that all or some of the programming and processing described herein can be accomplished within the continuous glucose sensor, the receiver, a single point glucose monitor, and/or the delivery device, or any combination thereof. Similarly, displays, alarms and other user interface functions can be incorporated into any of the individual components of the integrated delivery device.

In some embodiments, the receiver includes a housing with integrated electronics located within the receiver housing. In some embodiments, a hand-held medicament injection pen comprises a housing, and wherein the integrated electronics are located within the hand-held medicament injection pen housing. In some embodiments, a housing is configured to receive a hand-held medicament injection pen, wherein the housing includes integrated electronics therein. In some embodiments, a hand-held medicament injection pen kit is provided, wherein the hand-held medicament injection pen kit is configured to receive the hand-held medicament injection pen (and can be configured to receive other accessories, such as medicament cartridges, needles, and the like), wherein the integrated electronics are located within the hand-held medicament injection pen kit. In some embodiments, a receiver, integrated electronics and hand-held medicament injection pen are integrally formed into one housing.

A quartz crystal 176 is operably connected to an RF transceiver 178 that together function to receive and synchronize data streams via an antenna 180 (for example, transmission 140). Once received, a processor module 182 processes the signals, such as described below. However other methods of wired or wireless communication can be substituted for the RF communication described herein.

The processor (or processor module) 182 is the central control unit that performs the processing, such as storing data, analyzing a continuous glucose sensor data stream, analyzing single point glucose values, accuracy checking, checking clinical acceptability, calibrating sensor data, downloading data, recommending therapy instructions, calculating medicament delivery amount, type and time, learning individual metabolic patterns, and controlling the user interface, by providing prompts, messages, warnings and alarms, and the like. The processor (or processor module) can include hardware and software that performs the processing described herein, including for example, read only memory (ROM), such as flash memory, provides permanent or semi-permanent storage of data, storing data such as sensor ID, receiver ID, and programming to process data streams (for example, programming for performing estimation and other algorithms described elsewhere herein), and random access memory (RAM) stores the system's cache memory and is helpful in data processing.

In some embodiments, the processor 182 monitors the continuous glucose sensor data stream 140 to determine a preferable time for capturing glucose concentration values, using the single point glucose monitor electronics 116 for calibration of the continuous sensor data stream. For example, when sensor glucose data (for example, observed from the data stream) changes too rapidly, a single point glucose monitor reading may not be sufficiently reliable for calibration during unstable glucose changes in the host; in contrast, when sensor glucose data are relatively stable (for example, relatively low rate of change), a single point glucose monitor reading can be taken for a reliable calibration. In some additional embodiments, the processor can prompt the user via the user interface to obtain a single point glucose value for calibration at predetermined intervals. In some additional embodiments, the user interface can prompt the user to obtain a single point glucose monitor value for calibration based upon certain events, such as meals, exercise, large excursions in glucose levels, faulty or interrupted data readings, and the like. In some embodiments, certain acceptability parameters can be set for reference values received from the single point glucose monitor. For example, in one embodiment, the receiver only accepts reference glucose data between about 40 and about 400 mg/dL.

In some embodiments, the processor 182 monitors the continuous glucose sensor data to determine a preferable time for medicament delivery, including type, amount, and time. In some embodiments, the processor is programmed to detect impending clinical risk and can request data input, a reference glucose value from the single point glucose monitor, and the like, in order to confirm a therapy recommendation. In some embodiments, the processor is programmed to process continuous glucose data and medicament therapies, to adaptively adjust to an individual's metabolic patterns. In some embodiments, the processor is programmed to project glucose trends based on data from the integrated system (for example, medicament delivery information, user input, and the like). In some embodiments, the processor is programmed to calibrate the continuous glucose sensor based on the integrated single point glucose monitor 18. Numerous other programming can be incorporated into the processor, as is appreciated by one skilled in the art, as is described in cited patents and patent applications here, and as is described with reference to flowcharts of FIGS. 15 and 16.

A battery 192 is operably connected to the processor 182 and provides power for the receiver. In one embodiment, the battery is a standard AAA alkaline battery, however any appropriately sized and powered battery can be used. In some embodiments, a plurality of batteries can be used to power the system. In some embodiments, a power port (not shown) is provided permit recharging of rechargeable batteries. A quartz crystal 194 is operably connected to the processor 182 and maintains system time for the computer system as a whole.

A PC communication (com) port 190 can be provided to enable communication with systems, for example, a serial communications port, allows for communicating with another computer system (for example, PC, PDA, server, or the like). In one exemplary embodiment, the receiver is configured to download historical data to a physician's PC for retrospective analysis by the physician. The PC communication port 190 can also be used to interface with other medical devices, for example pacemakers, implanted analyte sensor patches, infusion devices, telemetry devices, and the like.

A user interface 196 includes a keyboard 198, a speaker 100, a vibrator 102, a backlight 104, a liquid crystal display (LCD) 106, one or more buttons 108, and/or a scroll wheel 44 (shown in FIG. 4, for example). The components that comprise the user interface 196 provide controls to interact with the user. The keyboard 198 can allow, for example, input of user information about himself/herself, such as mealtime, exercise, medicament administration, and reference glucose values. The speaker 100 can provide, for example, audible signals or alerts for conditions such as present and/or predicted hyper- and hypoglycemic conditions. The vibrator 102 can provide, for example, tactile signals or alerts for reasons such as described with reference to the speaker, above. The backlight 104 can be provided, for example, to aid the user in reading the LCD in low light conditions. The LCD 106 can be provided, for example, to provide the user with visual data output. In some embodiments, the LCD is a touch-activated screen. The buttons 108 and/or scroll wheel 44 (see FIGS. 4 and 6, for example) can provide for toggle, menu selection, option selection, mode selection, and reset, for example. In some alternative embodiments, a microphone can be provided to allow for voice-activated control.

Figure 14:
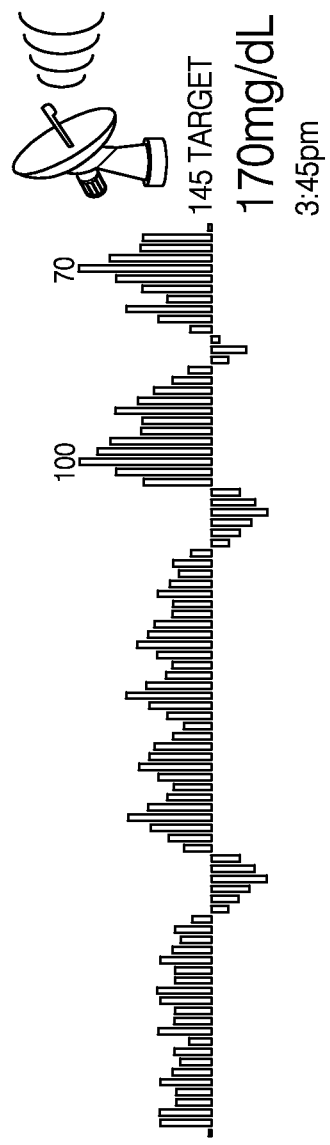
FIG. 14 is graphical representation of integrated data that can be displayed on an LCD screen, for example, in one embodiment.

The user interface 196, which is operably connected to the processor 182, serves to provide data input and output for both the continuous glucose sensor, the hand-held medicament injection pen, and/or for the single point glucose monitor. Data output includes a numeric estimated analyte value, an indication of directional trend of analyte concentration, a graphical representation of the measured analyte data over a period of time, alarms/alerts, therapy recommendations, actual therapy administered, event markers, and the like. In some embodiments, the integrated electronics are configured to display a representation of a target glucose value or target glucose range on the user interface. Some additional data representations are disclosed in Published U.S. Patent Application No. 2005-0203360, which is incorporated herein by reference in its entirety FIG. 14 is a graphical representation of integrated data that can be displayed on an LCD screen 106, for example, in one embodiment. In this embodiment, the integrated electronics are configured to display a representation of a value of the sensor data (illustrated by bars in this illustration) above or below the target glucose value (illustrated by a line at "145" (mg/dL) in FIG. 14) or target glucose range (not shown) on the user interface. In the illustrated embodiment, the x-axis represents time and the y-axis represents glucose concentration in mg/dL. Glucose concentration is graphed over time according to its value as compared to a target (e.g., above and/or below the target). For example, if a target glucose concentration is set at 145 mg/dL and the actual glucose concentration is 180 mg/dL, then the bar value represents 35 mg/dL (180 mg/dL-145 mg/dL) above the target glucose concentration for that glucose measurement. While FIG. 14 shows the glucose concentration as a series of black bars, the data can be shown using a variety of symbols. For example, in one embodiment, the bars are colored, with green bars above the target and red bars below the target. In another embodiment using colored bars, the bars are colored as a gradient, wherein the bars within the target range are green, changing to yellow and then red as the host's glucose concentration is farther and farther away from the target range. In another embodiment, dots, circles, squares and the like are used instead of bars. In still another embodiment, stars, hearts, a thumbs-up graphic, and/or smiley-faces (colored and/or black and white) can be added to the graph to denote periods of time during which the host was within the target. In a further embodiment, the stars, hearts, a thumbs-up graphic, and/or smiley-faces can blink or flash as an award for staying within the target. In still another embodiment, instead of using colors, portions of the graph are made to blink/flash. For example, in one embodiment, a series of dots plot out the host's glucose concentration, with the most recent concentration blinking.

In some embodiments, the integrated electronics are configured to display a representation of medicament delivery on the user interface adjacent to substantially time-corresponding sensor data, which is illustrated as "10U" and "7U" in FIG. 14, representing the units of medicament delivered in a bolus. In these embodiments, the representation of medicament delivery is located substantially adjacent to a glucose value measured at substantially the same time as the medicament delivery. It is believed that by providing a representation of medicament delivery on the user adjacent to substantially time-corresponding sensor data, a user can see the affect of the therapy (e.g., medicament bolus) on their glucose concentration and/or achievement of target glucose concentration.

In some embodiments, the integrated electronics are configured to display glucose data on the user interface for 1 hour, 3 hours, 6 hours, 9 hours, 1 day, 3 days, 5 days, 7 days, 1 month, 3 months, year-to-date, 1 year, 2 years, 5 years, and the like for example, which provides the user with actual, averaged or estimated glucose values over that time period. In some embodiments, the integrated electronics are configured to display glucose trend data (e.g., charts or graphs) on the user interface, including a graphical representation of glucose values as they change over time. In some embodiments, the integrated electronics are configured to display comparison data for two periods (e.g., charts or graphs) on the user interface, including a trend-related finding between two specific periods of time. In some embodiments, the integrated electronics are configured to display modal day data (e.g., charts or graphs) on the user interface, including glucose summary data based on mealtimes. In some embodiments, the integrated electronics are configured to display modal week data (e.g., charts or graphs) on the user interface, including glucose summary data based on days of the week. In some embodiments, the integrated electronics are configured to display medicament dosage and effects data (e.g., charts or graphs) on the user interface, including medicament regimen information and changes in base medicament pattern. In some embodiments, the integrated electronics are configured to display hypoglycemia and hyperglycemia episode data (e.g., charts or graphs) on the user interface, including information regarding very low and very high glucose readings and/or glucose readings outside of a target range (which can be defined by the user in some embodiments). In some embodiments, the integrated electronics are configured to display rapid swings data (e.g., charts or graphs) on the user interface, including incidents of rapid swings between low and high blood glucose levels, which levels can be pre-programmed or settable by a user, for example.

In some embodiments, prompts or messages can be displayed on the user interface to convey information to the user, such as malfunction, outlier values, missed data transmissions, or the like, for the continuous glucose sensor. Additionally, prompts can be displayed to guide the user through calibration of the continuous glucose sensor. Even more, calibrated sensor glucose data can be displayed, which is described in more detail with reference to co-pending U.S. Patent Publication No. US-2005-0027463-A1 and U.S. Patent Publication No. US-2005-0203360-A1, each of which is incorporated herein by reference in their entirety.

In some embodiments, prompts or messages about the hand-held medicament injection pen can be displayed on the user interface to inform or confirm to the user type, amount, and time of medicament delivery. In some embodiments, the user interface provides historical data and analytes pattern information about the medicament delivery, and the host's metabolic response to that delivery, which may be useful to a patient or doctor in determining the level of effect of various medicaments.

Referring again to FIG. 13, electronics 110 associated with the delivery device 16 are operably connected to the processor 182 and include a processor 112 for processing data associated with the delivery device 16 and include at least a wired or wireless connection 114 for transmission of data between the processor 182 of the receiver 14 and the processor module 112 of the delivery device 16. In some embodiments, the delivery device electronics 110 are at least partially or fully incorporated into the integrated electronics, such that electronics 110 may not be required. Other electronics associated with any of the delivery devices cited herein, or other known delivery devices, can be implemented with the delivery device electronics 110 described herein, as is appreciated by one skilled in the art.

In some embodiments, the processor module 112 comprises programming for processing the delivery information in combination with the continuous sensor information. In some alternative embodiments, the processor 182 comprises programming for processing the delivery information in combination with the continuous sensor information. In some embodiments, both processors 182 and 112 mutually process information related to each component.

In some embodiments, the hand-held medicament injection pen 16 further includes a user interface (not shown), which can include a display and/or buttons, for example. U.S. Pat. No. 6,192,891, U.S. Pat. No. 5,536,249, and U.S. Pat. No. 6,471,689 describe some examples of incorporation of a user interface into a hand-held medicament injection pen, as is appreciated by one skilled in the art.

Electronics 116 associated with the optional single point glucose monitor 18 are operably connected to the processor module 120 and include a potentiostat 118, in one embodiment, that measures a current flow produced at the working electrode when a biological sample is placed on the sensing membrane, such as described above.

Algorithms

Figure 15:
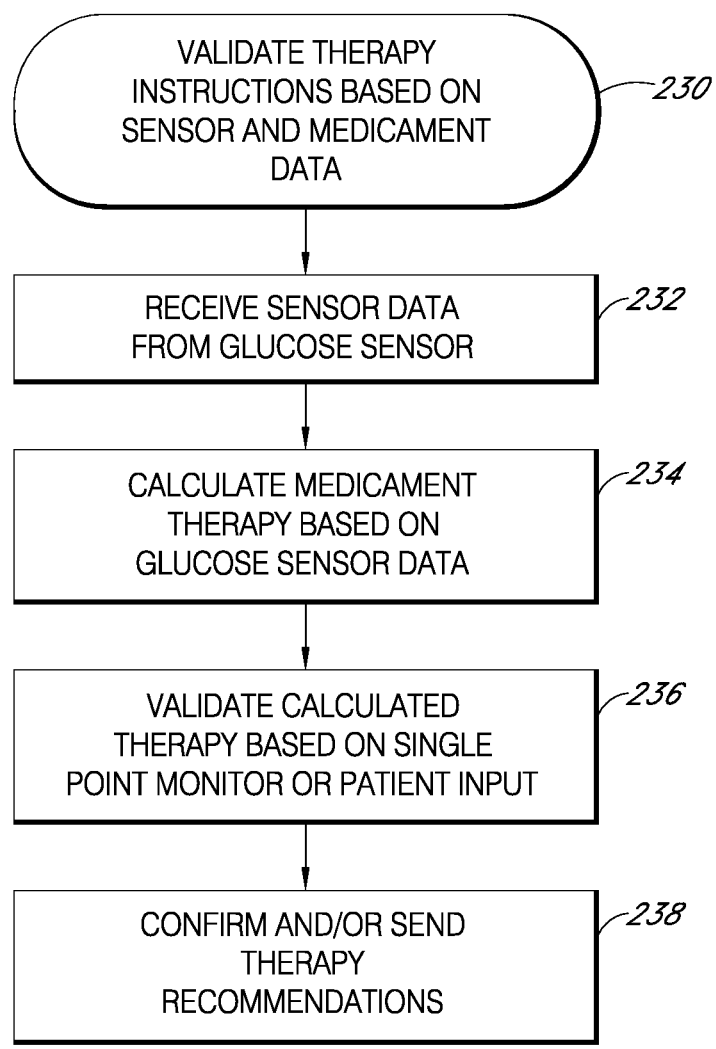
FIG. 15 is a flow chart that illustrates the process of validating therapy instructions prior to medicament delivery in one embodiment.

FIG. 15 is a flow chart that illustrates the process 230 of validating therapy instructions prior to medicament delivery, in one embodiment. In some embodiments, the system is configured with programming that provides for validation of therapy recommendations. In some embodiments, the therapy recommendations include a suggestion, on the user interface, of time, amount, and type of medicament to delivery. In some embodiments, therapy instructions include calculating a time, an amount, and/or a type of medicament delivery to administer, and optionally transmitting those instructions to the delivery device. In some embodiments, therapy instructions include that portion of a closed loop system wherein the determination and delivery of medicament is accomplished, as is appreciated by one skilled in the art.

In some embodiments, the therapy recommendations are displayed on a user interface (e.g., of an integrated housing) by representative icons, such as a syringe, a medicament pen, a medicament pump, an apple, orange juice, candy bar, or any icon representative of eating, drinking, or administering therapy, for example. Additionally or alternatively, the therapy recommendations can be preset alphanumeric messages, for example, "3.0 Units," "consume carbohydrates," "inject medicament" or "no therapy required", and can include brand names, amounts, times, acronyms, codes and the like. In response to the recommendation of therapy displayed on the user interface, the user can confirm, modify, and/or cancel the recommended therapy, after which, the integrated hand-held medicament injection pen is configured to administer the appropriate therapy.

Although computing and processing of data is increasingly complex and reliable, there are circumstances in which the therapy recommendations necessitate human intervention. Some examples include when a user is about to alter his/her metabolic state, for example due to a behavior such as exercise, meal, pending manual medicament delivery, and the like. In such examples, the therapy recommendations determined by the programming may not have considered present or upcoming behavior, which can change the recommended therapy. Numerous such circumstances can occur, such that a validation can be advantageous in order to ensure that therapy recommendations are appropriately administered.

At block 232, a sensor data receiving module, also referred to as the sensor data module, receives sensor data (e.g., a data stream), including one or more time-spaced sensor data points, from a sensor via the receiver, which can be in wired or wireless communication with the sensor. The sensor data point(s) can be raw or smoothed, such as described in U.S. Patent Publication No. US-2005-0043598-A1, which is incorporated herein by reference in its entirety.

At block 234, a medicament calculation module, which is a part of a processor module, calculates a recommended medicament therapy based on the received sensor data. A variety of algorithms can be used to calculate a recommended therapy as is appreciated by one skilled in the art.

At block 236, a validation module, which is a part of the processor module, optionally validates the recommended therapy. The validation can include a request, from the user or another component of the integrated system 10, for additional data to ensure safe and accurate medicament recommendation or delivery. In some embodiments, the validation module requests and/or considers additional input, such as time of day, meals, sleep, calories, exercise, sickness, or the like. In some embodiments, the validation module is configured to request this information from the user. In some embodiments, the validation module is responsive to a user inputting such information.

In some embodiments, when the integrated system 10 is in a fully automated mode, the validation module is triggered when a potential risk is evaluated. For example, when a clinically risky discrepancy is evaluated, when the acceleration of the glucose value is changing or is low (indicative of a significant change in glucose trend), when it is near a normal meal, exercise or sleep time, when a medicament delivery is expected based on an individual's dosing patterns, and/or a variety of other such situations, wherein outside influences (meal time, exercise, regular medicament delivery, or the like) may require additional consideration in the therapy instructions. These conditions for triggering the validation module can be pre-programmed and/or can be learned over time, for example, as the processor module monitors and patterns an individual's behavior patterns.

In some embodiments, the system can be programmed to request additional information from the user regarding outside influences unknown to the integrated system prior to validation. For example, exercise, food or medicament intake, rest, and the like can be input into the receiver for incorporation into a parameter of the programming (algorithms) that processes the therapy recommendations.

At block 238, the receiver confirms and sends (for example, displays, transmits and/or delivers) the therapy recommendations. In some embodiments, the receiver can simply confirm and display the recommended therapy, for example. In some embodiments, the receiver can confirm, transmit, and optionally deliver instructions, to the delivery device, regarding the recommended therapy, for example. In some embodiments, the receiver can confirm and ensure the delivery of the recommended therapy, for example. In some embodiments, a glucose value measured by the single point glucose monitor is used to validate the therapy recommendation. It is noted that these examples are not meant to be limiting and there are a variety of methods by which the receiver can confirm, display, transmit, and/or deliver the recommended therapy, within the scope of the preferred embodiments.

Figure 16:
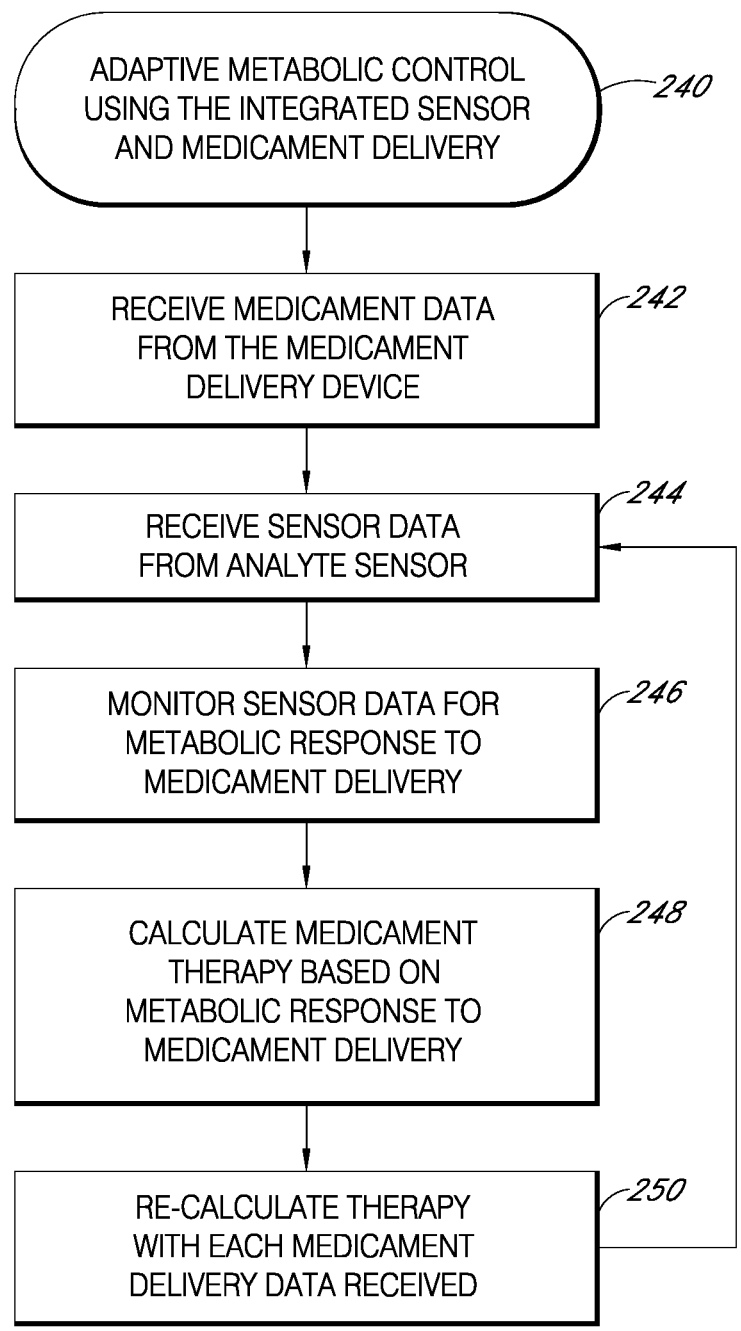
FIG. 16 is a flow chart that illustrates the process of providing adaptive metabolic control using an integrated sensor and hand-held medicament injection pen in one embodiment.

FIG. 16 is a flow chart 240 that illustrates the process of providing adaptive metabolic control using an integrated system, in one embodiment. In this embodiment, the integrated system is programmed to learn the patterns of the individual's metabolisms, including metabolic response to medicament delivery.

In some embodiments, the system is configured with programming that provides therapy recommendations based on at least one of the following: glucose concentration, glucose trend information (e.g., rate of change, acceleration, etc), predicted glucose values, food intake (e.g., carbohydrates), exercise, illness, sleep, time of day, and the like. In one such example, the system is configured to request carbohydrate and exercise information, from the user, which is used in combination with data from the continuous glucose sensor to calculate a recommended dose of medicament for injection (e.g., with a hand-held medicament injection pen). In some embodiments, when the user's glucose concentration falls outside of a target range (or is predicted to fall outside of a target range), a recommended therapy is displayed on the user interface (e.g., of an integrated pen as described above), wherein the user has an opportunity to validate the therapy recommendation prior to injection of medicament. After the user has injected the medicament, the amount (and type, etc) of medicament, which is stored in the integrated system, is analyzed, in combination with the user's metabolic response (i.e., continuous glucose data) over a predetermine time period (e.g., minutes to hours after injection), to determine whether the amount (and/or type) of medicament administered affected a desired change (e.g., glucose concentration within a target range). Preferably, the system's programming is configured to process the medicament delivery information and the continuous glucose sensor information, to adaptively adjust therapy recommendations to an individual's metabolic patterns. Namely, with each medicament injection and/or over multiple medicament injections, the system is configured to adaptively learn how a user responds to various therapies and to adaptively adjust the calculation of therapy recommendations accordingly.

At block 242, a medicament data receiving module, which can be programmed within the receiver 14 and/or medicament delivery device 16, receives medicament delivery data, including time, amount, and/or type. In some embodiments, the user is prompted to input medicament delivery information into the user interface. In some embodiments, the medicament delivery device 16 sends the medicament delivery data to the medicament data-receiving module.

At block 244, a sensor data receiving module, also referred to as the sensor data module, receives sensor data (e.g., a data stream), including one or more time-spaced sensor data points, from a sensor via the receiver, which can be in wired or wireless communication with the sensor.

At block 246, the processor module, which can be programmed into the receiver 14 and/or the delivery device 16, is programmed to monitor the sensor data from the sensor data module 242 and medicament delivery data from the medicament delivery module 244 to determine an individual's metabolic profile, including their response to various times, amounts, and/or types of medicaments. The processor module can use any pattern recognition-type algorithm, as is appreciated by one skilled in the art, to quantify the individual's metabolic profile.

At block 248, a medicament calculation module, which is a part of a processor module, calculates the recommended medicament based on the sensor glucose data, medicament delivery data, and/or the host's individual's metabolic profile. In some embodiments, the recommended therapy is validated such as described with reference to FIG. 15, above. In some embodiments, the recommended therapy is manually, semi-automatically, or automatically delivered to the host.

At block 250, the process of monitoring and evaluation a host's metabolic profile is repeated with each receipt of new medicament delivery data, wherein the processor monitors the sensor data and the associated medicament delivery data to determine the individual's metabolic response, in order to adaptively adjust to newly determined metabolic profile or patterns, if necessary. This process can be continuous throughout the life of the integrated system, can be initiated based on conditions met by the continuous glucose sensor, can be triggered by a patient or doctor, and/or can be provided during a start-up or learning phase.

While not wishing to be bound by theory, it is believed that by adaptively adjusting the medicament delivery based on an individual's metabolic profile, including response to medicaments, improved long-term patient care and overall health can be achieved.

Integrated Systems for Clinical Settings

Figure 17:
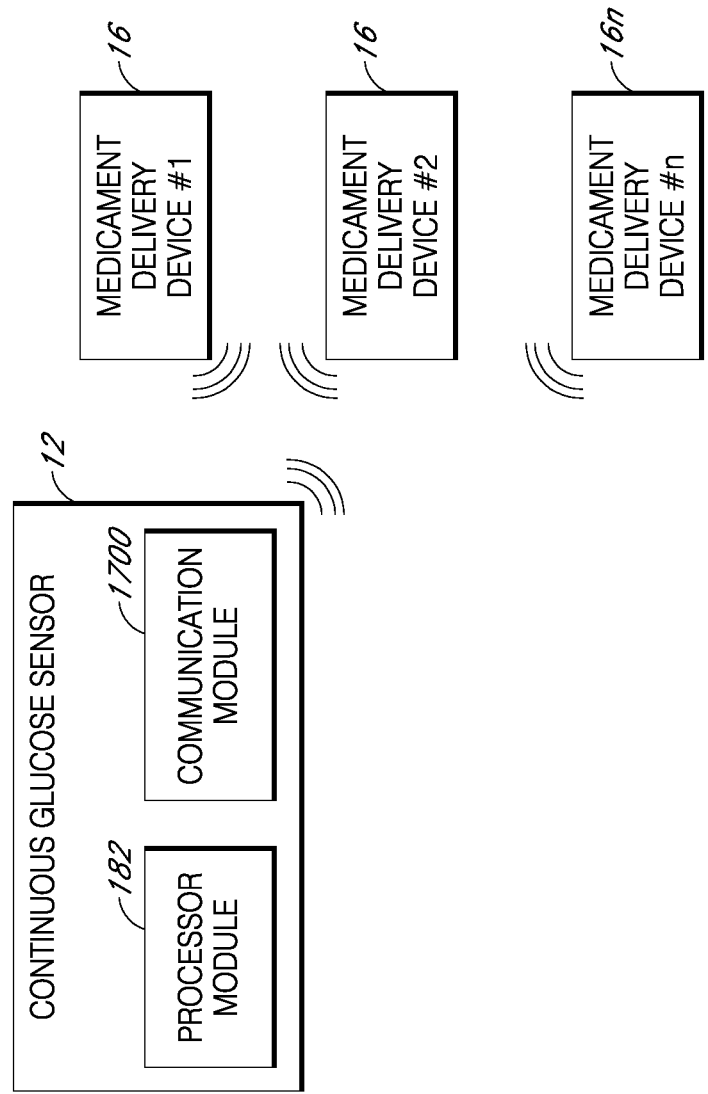
FIG. 17 is a block diagram illustrating an integrated system, in one embodiment, including a continuous glucose sensor and a plurality of hand-held medicament injection pens, in one embodiment.

FIG. 17 is a block diagram illustrating an integrated diabetes monitoring and treatment system for use in a clinical setting, in one embodiment. The integrated system includes a continuous glucose sensor 12 configured to continuously detect a signal associated with a glucose concentration of a host, a processor module 182 configured and arranged to process the signal to generate sensor data and a therapy instruction, wherein the therapy instruction comprises a deliverable medicament dose in some embodiments, and a communication module 1700 configured and arranged to communicate the therapy instruction between the processor module and a medicament delivery device 16, such as one or more hand-held medicament injection pens. Although much of the description is related to hand-held medicament injection pens, the preferred embodiments can be applied to any such medicament delivery device configured for bolus therapy, such as medicament inhalers, and/or the like. In one exemplary embodiment, the glucose sensor is implanted in a host. In some embodiments, a processor module 182 associated with the sensor, processes the sensor data to calculate and medicament therapy (e.g., a medicament dose to be delivered to the host) and a communication module 1700 communicates the medicament therapy instruction to the hand-held medicament injection pen 16, such as but not limited to via wireless communication. In some embodiments, the processor continually calculates a deliverable medicament dose that can be transmitted to a hand-held medicament injection pen within range of the communication module. In other embodiments, the processor module calculates the medicament therapy in response to interrogation by a hand-held medicament injection pen, such as via wireless communication. For example, a caretaker can use a hand-held medicament injection pen 16 to interrogate the patient's continuous glucose sensor 12, to receive the medicament therapy instruction (e.g., identification of the host and a deliverable medicament dose calculated by the processor module 182; communicated to the hand-held medicament injection pen by the communication module 1700). In some preferred embodiments, the continuous glucose sensor includes the processor module configured to determine a medicament therapy instruction. However, in some embodiments, the system is configured such that at least a portion of the processor module is disposed within the hand-held medicament injection pen, such that the medicament device performs at least some of the calculations to generate the medicament therapy instruction. In some embodiments, the continuous glucose sensor includes only the minimal electronics necessary to collect the sensor data and (optionally) process the collected data into a data packet that is then communicated to the hand-held medicament injection pen, wherein the hand-held medicament injection pen includes a processor module and processes the data received to generate the medicament therapy instruction. Various intermediate configurations can be appreciated by one skilled in the art.

After receiving the medicament therapy instruction, the caretaker can deliver the medicament dose to the patient, simply by actuating the medicament injection pen. As shown in FIG. 17, the continuous glucose sensor 12 is configured and arranged to communicate with a plurality of hand-held medicament injection pens (16n), such that in a clinical setting, such as a hospital, each caretaker can carry a hand-held medicament injection pen and use that hand-held medicament injection pen to deliver medicament to the patient (host) as a part of the normal course of patient care, similar to the practice of measuring the patient's temperature, pulse, blood pressure, respiration, $pO_2$, urine output, and the like, at regular intervals as determined by hospital protocol.

In preferred embodiments, the processor module 182 includes an input module configured for the input of host information and/or a therapy instruction. Preferably, the device is configured and arranged to be programmed (e.g., operated) by an external programmer, such as a caretaker. Such information can be input into the device when the continuous glucose sensor 12 is implanted in the host. For example, in some embodiments, the input module is configured to receive information from a user interface, a hand-held medicament injection pen, an infusion pump, a patient monitor, a single-point glucose monitor, a receiver, and the like. In some embodiments, the information can be input via a user interface incorporated into the continuous glucose sensor or via the hand-held medicament injection pen, which can include a user interface. In other embodiments, the information can be input via a tertiary device having a user interface and configured for communication with the communication module, such as but not limited to a computer, patient monitor, PDA and the like.

In preferred embodiments, host information that can be input via an input module associated with the continuous glucose sensor and/or the hand-held medicament injection pen, wherein the host information includes but is not limited to a host ID, such as a unique identifying code assigned to a patient, host physical characteristics, a type of medicament to be delivered to the host, a therapy protocol assigned to the host, and the like. A therapy instruction includes but is not limited to selection of a therapy protocol and/or portions thereof, including but not limited to a target host blood glucose concentration and/or range of concentrations, selection of an alert to be sounded if the host meets a predetermined criterion, and the like. In preferred embodiments, the therapy instruction comprises at least one of a type of medicament, a medicament dose, and a delivery time. The integrated electronics are further configured and arranged to process host information and/or a therapy instruction. For example, the integrated electronics can process the continuous glucose sensor data in the context of a selected protocol, such that medicament therapies are calculated to maintain the host within a target blood glucose concentration range (e.g., 100-140 mg/dl blood glucose), for example. In preferred embodiments, the device includes a display module configured and arranged for display of the host information, sensor data, the therapy instruction, the deliverable medicament dose, an alert and/or an alarm.

In some embodiments, the system is configured for communication with a data repository system and/or device (e.g., portable and/or remotely located) configured to receive host information, sensor data, the therapy instruction, the deliverable medicament dose, an alert, an alarm, a predictive alarm, and the like. For example, in some embodiments, the communication module is configured to transmit information related to the host and his/her treatment to a data repository that records and tracks the host's condition and/or enters the data into the host's patient chart. For example, the data can be electronically entered into the host's patient chart remotely, such as in medical records. In another embodiment, the information can be monitored remotely by the patient's physician using a data repository device integrated into a display device, such as a personal computer, cell phone, PDA and the like, which enables the physician to receive predictive alarms of upcoming problems/events or alarms/alerts related to the host's current physical state. Similarly, when the physician visits the host, he can use a portable data repository to collect pertinent data from the continuous glucose sensor. In one exemplary embodiment, the continuous glucose sensor is configured to communicate data and information related to the medicament therapy to a separate and/or remote data repository, for example, wherein the sensor is configured to transmit this information to a remote monitor carried by the physician or at the nurse's station, or to a remote location (e.g., medical records) for storage and/or monitoring. In another exemplary embodiment, the hand-held medicament injection pen (e.g., insulin pen) is configured to communicate data received from the continuous glucose sensor (e.g., via the communication module) and information related to medicament therapy delivered to the host to the separate and/or remote data repository, for example, by transmitting this information to a remote monitor carried by the physician or at the nurse's station, or to a remote location (e.g., medical records) for storage and/or monitoring.

As shown in FIG. 17, the integrated system includes a hand-held medicament injection pen 16, configured to communicate with the continuous glucose sensor 12 (e.g., and vice versa) and to deliver a medicament to the host. In some embodiments, the system is configured to communicate with a plurality of hand-held medicament injection pens 16n. For example, in one embodiment, the system is configured such that a host wearing a continuous glucose sensor can be monitored and/or treated by a plurality of caretakers, each of whom carries a hand-held medicament injection pen. For example, the host's sensor is configured to communicate with a first caretaker's hand-held medicament injection pen, then a second caretaker's hand-held medicament injection pen, and so on. As a non-limiting example, for a host in the hospital, at the initiation of each work shift, a new nurse can check the host's glucose level (e.g., via communication between the host's sensor and the nurse's hand-held medicament injection pen, as described herein) and deliver insulin, if needed. Accordingly, the continuous glucose sensor and the hand-held medicament injection pen(s) can communicate with each other when operably connected, to allow wired and/or wireless communication therebetween.

Figure 18:
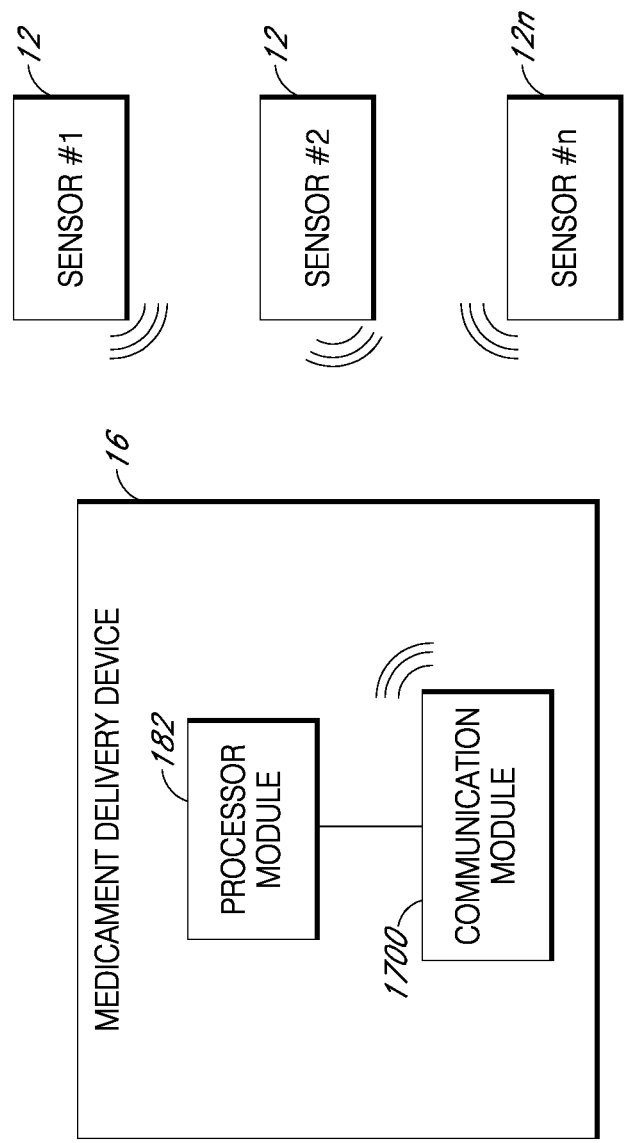
FIG. 18 is a block diagram illustrating an integrated system, in one embodiment, including a plurality of continuous glucose sensors and a hand-held medicament injection pen, in one embodiment.

FIG. 18 is a block diagram illustrating a medicament delivery device for monitoring and treating diabetes in one or more host, such as but not limited to in a clinical setting, in another embodiment. Although much of the description is related to hand-held medicament injection pens, the preferred embodiments can be applied to any such medicament delivery device configured for bolus therapy, such as medicament inhalers, and/or the like. The medicament delivery device 16 includes a communication module 1700 configured to interrogate an operably connected continuous glucose sensor 12 and to receive sensor data (e.g., a signal associated with a glucose concentration of a host) therefrom, a processor module 182 configured to process the sensor data and calculate a medicament therapy, and a hand-held medicament injection pen (e.g., configured to receive a cartridge of medicament for injection) configured and arranged to deliver medicament based at least in part on the medicament therapy. In some embodiments, the system is configured for use with a continuous glucose sensor configured and arranged for transcutaneous implantation in the host, such as for use in the general wards, in which case the signal generated by the glucose sensor can be measured in the interstitial fluid, for example. In other embodiments, the system is configured for use with a continuous glucose sensor configured and arranged for implantation in the host's circulatory system (e.g., via an artery or vein) or in an extracorporeal blood circulation device, in which case the signal generated by the glucose sensor is associated with a glucose concentration of a sample of the host's circulatory system.

In one embodiment, the communication module 1700, which can be integrally formed with the hand-held medicament injection pen or in wired or wireless communication therewith or detachably connected to the hand-held medicament injection pen, is configured to receive information from an operably connected continuous glucose sensor when the hand-held medicament injection pen interrogates it. The hand-held medicament injection pen and the continuous glucose sensor can be operably connected using any method known in the art, such as but not limited to by wired and/or wireless communication. In one embodiment, the caretaker can simply hold the hand-held medicament injection pen within a predetermined communication range, such that the hand-held medicament injection pen and continuous glucose sensor can communicate with each other by wireless communication, such as RF, IR, Bluetooth, and the like. In another embodiment, the system is configured such that the hand-held medicament injection pen can communicate with the sensor via inductive coupling communication when the caretaker holds the pen adjacent to the sensor or touches the pen to the sensor. A variety of alternative useful communication methodologies are appreciated by one skilled in the art.

In some embodiments, the hand-held medicament injection pen 16 includes a processor module 182 that includes programming for calculating the medicament therapy based at least in part on the sensor data, as described elsewhere herein. For example, the programming directs use of algorithms for calculating an amount of medicament to be delivered to the host, based at least in part on the sensor data received from the host's continuous glucose sensor. In preferred embodiments, the processor module calculates dosing information (e.g., a type of medicament to be delivered, an amount of medicament to be delivered and a time of delivery, and/or the like) using one or more algorithms described elsewhere herein. While the embodiment shown in FIG. 18 depicts the processor module 182 disposed within the hand-held medicament injection pen, in some embodiments, some or all of the processor electronics and/or functions can reside within the continuous analyte sensor(s) 12$n$. For example, in some embodiments, the electronics/components/modules (e.g., processor module, communication module, and the like) of receiver 14, as depicted in FIG. 18, can be distributed among other integrated system components, such as but not limited to the continuous analyte sensor 12 and the hand-held medicament injection pen.

In some embodiments, the processor module 182 is configured for validation of the dosing information. For example, the processor module can request validation of a calculated medicament dose and/or identification of the host prior to injection of the dose into the host. In some embodiments, the system is configured to disallow/prevent injection unless at least the dose (e.g., medicament identity, amount of medicament to be delivered and/or time of delivery) and/or host information has been validated. For example, the hand-held medicament injection pen can interrogate a first continuous glucose sensor, calculate a medicament dose and request validation prior to allowing the caretaker to inject the calculated dose into the host. The caretaker can move on to a second host and repeat the process. Accordingly, accidental injection (e.g., of one host's medicament dose into another host) can be avoided.

Preferably, the hand-held medicament injection pen includes a user interface, such as that described with reference to FIG. 13, configured and arranged for input and/or display of at least some medical information, wherein medical information comprises at least one of host information, received sensor data, processed sensor data, the calculated medicament therapy, a delivered medicament therapy, an instruction, an alert, an alarm and a failsafe. Host information includes at least one of a host ID, type of medicament to be received, a target glucose level and/or range, predicted hypoglycemia/hypoglycemia, a therapy protocol, an alert, and an alarm. In some embodiments, the user interface is detachably connected to the hand-held medicament injection pen, such as via mutually engaging contacts that allow communication therebetween then the user interface is connected with the hand-held medicament injection pen. However, in other embodiments, the user interface (in part or in its entirety) is integrally formed with the hand-held medicament injection pen.

In some embodiments, the hand-held medicament injection pen includes a communication module 1700 configured to communicate treatment information (e.g., host information, continuous glucose information, the therapy protocol, dosing information, medicament type, medicament delivered and time of medicament delivery) to a central monitor. A central monitor can be a device configured to receive information communicated from one or more hand-held medicament injection pens, such as a computerized device including a user interface for display of received information and optionally for communicating commands/instructions back to one or more hand-held medicament injection pens. In some embodiments, a central monitor can include one or more intermediate receiving devices, located about the hospital ward or at the nurses' station, and configured to receive the communicated information wirelessly, and then to relay the communicated information to the central monitor via a wired and/or wireless connection. In some embodiments, the system can be configured such that when a caretaker moves within a range of the intermediate receiving device and/or the central monitor itself, the receiving device/central monitor recognizes the hand-held medicament injection pen and triggers the pen to download information related to treatment of the host(s). Alternatively, recognition of the receiving device/central monitor by the hand-held medicament injection pen triggers the information download. The central monitor can be located in a centralized location, such as at the nurses' station or in medical records, or in a more private remote location, such as in the physician's office or in a nurse supervisor's office. Location of the central monitor at a location remote from the glucose sensor(s) and/or hand-held medicament injection pen enables remote monitoring of hand-held medicament injection pen use (e.g., how, when & where it is used) and/or function (e.g., if it is functioning properly).

In some embodiments, at least a portion of the system is configured provide adaptive metabolic control of the host's glucose, as described with reference to FIG. 16. Accordingly, the processor module is configured to receive sensor data and medicament therapy data (e.g., information related to medicament delivery to the host) and to monitor the sensor data for the host's metabolic response to the delivered medicament therapy. Accordingly, the system can calculate new medicament therapy based on the host's metabolic response to the medicament deliver. For example, if the host is highly sensitive to insulin, the system can intelligently monitor the host's response to an insulin dose and recalculate new medicament doses to take the host's insulin sensitivity into account. For example, in this particular circumstance, the processor module can calculate a small insulin dose, such that the host's glucose is maintained within the target range and hypoglycemia can be avoided. In another example, a host may be very insensitive to insulin. In the case of this insulin insensitive host, the system can monitor the lack of glucose concentration decreases upon insulin therapy delivery, and re-calculate future insulin doses (e.g., increase the volume of insulin delivered in a bolus dose and/or increase a basal delivery rate), such that this host's glucose can be maintained in the target range.

Integrated Systems for Ambulatory Use

Figure 19:
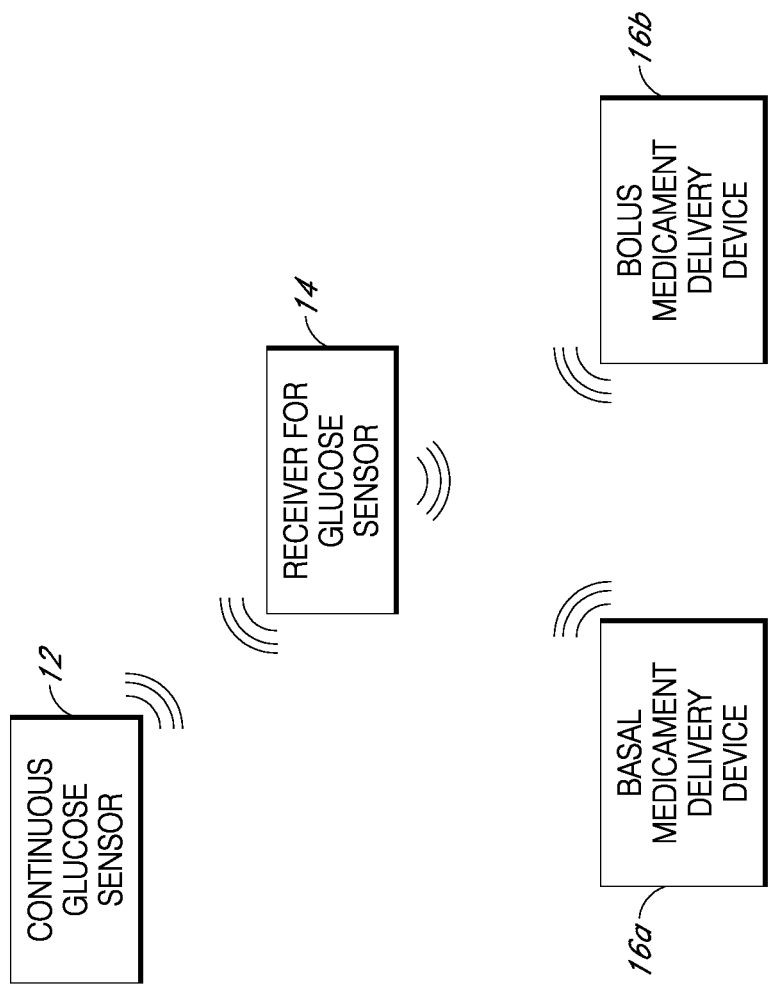
FIG. 19 is a block diagram illustrating an integrated system, in one embodiment, including a continuous glucose sensor, a receiver, a basal medicament delivery device and a bolus medicament delivery device, in one embodiment.

FIG. 19 is a block diagram illustrating an integrated system (monitoring and treating diabetes) for ambulatory use, in one embodiment. Such a system can be used by an ambulatory host to accurately monitor and treat his diabetes in real-time, by continuously monitoring his blood glucose level and infusing/injecting medicament with a basal medicament delivery device (e.g., a medicament pump) and a bolus medicament delivery device (e.g., a hand-held medicament injection pen) based at least in part on the data generated by the continuous glucose sensor, in either an open-loop, closed-loop or semi-closed-loop manner. In this embodiment, the integrated system includes a receiver 14 configured and arranged to receive continuous glucose sensor data from an operably connected continuous glucose sensor 12 implanted in a host, a processor module configured to process the continuous glucose sensor data and to provide medicament dosing information based at least in part on the continuous glucose sensor data, and a communication module configured and arranged to communicate the medicament dosing information with the medicament delivery devices 16a and 16b. Although a separate receiver is illustrated in FIG. 19, the receiver 14, including the processor module and/or communication module, can be located with the continuous glucose sensor, the basal medicament delivery device, the bolus medicament delivery device and/or combinations thereof, eliminating a need for a separately housed receiver.

In some embodiments, the basal medicament delivery device 16a is a medicament pump 16a, and the medicament dosing information comprises a basal dose of medicament. Accordingly, the processor module comprises programming to calculate the basal dose based at least in part on the continuous glucose sensor data. The receiver is configured to communicate the basal dose to the medicament pump, which, in turn, is configured to infuse the basal medicament dose into the host. Since the glucose sensor is a continuous glucose sensor, the system can be configured to continually recalculate the basal medicament dose and readjust the dose according to the host's needs, as indicated by the sensor data generated by the continuous glucose sensor. This enables adaptive metabolic control 240, as described with reference to FIG. 16, and optimized, real-time patient care.

In some preferred embodiments, the bolus medicament delivery device 16b is a hand-held medicament injection pen 16b and the medicament dosing information comprises a bolus medicament dose. Accordingly, the processor module comprises programming to calculate a bolus dose of medicament based at least in part on the continuous glucose sensor data. In some embodiments, the hand-held medicament injection pen is configured to infuse the same medicament as the medicament pump, while in other embodiments, the hand-held medicament injection pen is configured to infuse a medicament other than the medicament infused by the medicament pump, as is described in greater detail below. In some embodiments, the hand-held medicament injection pen includes a motor. The motor can be configured to automatically set the amount of medicament based at least in part on the medicament dosing information. For example the medicament dosing information can include an instruction for the hand-held medicament injection pen to automatically portion out a bolus medicament dose, which can be manually delivered by the host. In a further embodiment, the medicament is not delivered manually (e.g., by the host actuating a plunger to inject the medicament), rather the medicament is delivered semi-automatically, such that the host can hold the pen against the injection site (e.g., as if to inject the medicament) and actuate the pen to inject the medicament automatically. In this embodiment, the motor of the hand-held medicament injection pen can be configured to control a rate of medicament injection into the host and the medicament dosing information comprises an instruction for the hand-held medicament injection pen to deliver the bolus dose at a programmed rate. For example, it is known that the activity of injected medicament is dependent, in part, on the rate of injection. The hand-held medicament injection pen can be configured to inject the medicament at a rate selected to optimize the medicament's activity. Accordingly, the host's management of his blood sugar can be optimized and more consistent.

In some embodiments, the integrated system is configured for use with at least two hand-held medicament injection pens, such as both a medicament pump 16a and a hand-held medicament injection pen 16b. While the host may choose to use a single type of medicament in both devices, the convenient use of multiple modes of medicament delivery is enabled by this embodiment. For example, a first medicament delivery pump can be configured to deliver a first type of medicament, a second hand-held medicament injection pen can be configured to deliver a second type of medicament, and so on. In one exemplary embodiment, a medicament pump 16a is configured to deliver a long-acting medicament while a hand-held medicament injection pen 16b is configured to deliver a short-acting medicament. In a second exemplary embodiment, a medicament pump 16a is configured to deliver the short-acting medicament while a hand-held medicament injection pen 16b is configured to deliver the long-acting medicament. In a third exemplary embodiment, the two medicament delivery devices are configured to deliver the same type of medicament. For example, a basal medicament delivery device 16a can be configured to frequently deliver small doses (e.g., basal doses) of a short-acting insulin while a bolus medicament delivery device 16b can be configured to deliver a large dose (e.g., a bolus) of the short-acting insulin. Additional configurations are contemplated in the preferred embodiments. Regardless, of the type of medicament delivered and the delivery device used, the processor module includes programming to calculate the dose of that particular medicament in response to the continuous glucose sensor data, such that the host can be maintained within a target blood glucose range.

In preferred embodiments, the communication module is configured and arranged for wireless communication with the integrated hand-held medicament injection pen(s) 16a/16b, as described elsewhere herein. In some embodiments, the communication module comprises a transceiver configured and arranged to interrogate and/or provide medicament dosing information to the integrated hand-held medicament injection pen, however, other modes of wireless communication can be used. Preferably, the communication module is configured and arranged to enable communicate between the at least two integrated medicament delivery devices, such as but not limited to a medicament pump and a hand-held medicament injection pen. However, the use of additional hand-held medicament injection pens (e.g., a pump and two pens) is contemplated in the preferred embodiments. Preferably, in preferred embodiments, the communication module is configured and arranged to communicate with the at least two integrated medicament delivery devices simultaneously, for example, within substantially the same time period. Accordingly, the processor module calculates both the basal and bolus therapy recommendations for the devices, respectively, considering both the basal and bolus therapies together, and wherein the communication module is configured to communicate with the basal and bolus medicament delivery devices(s), such as to optimize control of the host's blood glucose level, such as maintaining the host's glucose level within a target range. In some embodiments, the communication module is configured to provide notification to the user, relating to injection of the medicament. For example, in some embodiments, the communication module can alert the host (e.g., via the receiver or one of the hand-held medicament injection pens) that a medicament dose is recommended, is being injected and/or has been injected, and optionally require validation of the medicament dose, as described elsewhere herein. For example, in one embodiment, the receiver and/or hand-held medicament injection pen is configured to emit an auditory alert (e.g., beep or buzz) when a bolus medicament dose have been calculated and is ready to be delivered.

In preferred embodiments, the integrated system includes a user interface configured and arranged to display continuous glucose sensor data and/or medicament dosing information. In some embodiments, the user interface is further configured for input of host information and/or medicament delivery device information, wherein the medicament delivery device information is associated with a medicament pump and a hand-held medicament injection pen. As described elsewhere herein, the host information can include at least one of host identity, host physical state, target glucose concentration and type of medicament to be delivered, and the like. Also described elsewhere herein, the medicament delivery information can include at least one of host identity, identification of a functionally connected hand-held medicament injection pen, a type of medicament to be delivered, a medicament delivery profile and/or protocols and a failsafe, and the like.

In one example, the host can use an integrated system including a continuous glucose sensor 12 (e.g., a sensor as described with reference to FIGS. 2B-2D), a receiver 14, a medicament infusion pump 16a and a hand-held medicament injection pen 16b, wherein the receiver is configured and arranged for wireless communication with the sensor, the medicament pump and the hand-held medicament injection pen. The receiver includes a user interface that is configured such that the host can program the system, such as using a toggle button and/or scroll wheel to select instructions on a display integrated into the receiver. In some embodiments, the receiver is integral with or detachably connected to either the medicament pump or the hand-held medicament injection pen (see FIGS. 3-12), such that the host is required to carry only the pump and the pen (e.g., instead of three devices; a receiver, a pump and a pen). In some embodiments, a medicament injection pen kit is provided, as described with reference to FIGS. 6-7. Preferably, the system is configured such that the host can program the medicament pump to deliver basal medicament doses and the hand-held medicament injection pen to deliver bolus medicament doses, all of which are based at least in part on sensor data generated by and received from the continuous glucose sensor, whereby the processor module processes the received sensor data, calculates the medicament doses (basal and/or bolus) and coordinates the delivery of the medicament doses to the host. For example, the processor module can calculate the basal medicament doses and automatically instruct the medicament pump to infuse the basal doses into the host (based at least in part on the continuous glucose sensor data). Substantially simultaneously, the processor module can calculate bolus medicament doses and set the hand-held medicament injection pen to deliver the calculated bolus dose, and then alert the host to inject the bolus dose. Advantageously, the host is afforded greater control and flexibility in managing his blood sugar, which, in turn, enables increased host health and reduced complication of his diabetes.

Methods and devices that are suitable for use in conjunction with aspects of the preferred embodiments are disclosed in U.S. Pat. No. 4,994,167; U.S. Pat. No. 4,757,022; U.S. Pat. No. 6,001,067; U.S. Pat. No. 6,741,877; U.S. Pat. No. 6,702,857; U.S. Pat. No. 6,558,321; U.S. Pat. No. 6,931,327; U.S. Pat. No. 6,862,465; U.S. Pat. No. 7,074,307; U.S. Pat. No. 7,081,195; U.S. Pat. No. 7,108,778; U.S. Pat. No. 7,110,803; U.S. Pat. No. 7,192,450; U.S. Pat. No. 7,226,978; U.S. Pat. No. 7,310,544; U.S. Pat. No. 7,364,592; and U.S. Pat. No. 7,366,556.

Methods and devices that are suitable for use in conjunction with aspects of the preferred embodiments are disclosed in U.S. Patent Publication No. US-2005-0143635-A1; U.S. Patent Publication No. US-2005-0181012-A1; U.S. Patent Publication No. US-2005-0177036-A1; U.S. Patent Publication No. US-2005-0124873-A1; U.S. Patent Publication No. US-2005-0115832-A1; U.S. Patent Publication No. US-2005-0245799-A1; U.S. Patent Publication No. US-2005-0245795-A1; U.S. Patent Publication No. US-2005-0242479-A1; U.S. Patent Publication No. US-2005-0182451-A1; U.S. Patent Publication No. US-2005-0056552-A1; U.S. Patent Publication No. US-2005-0192557-A1; U.S. Patent Publication No. US-2005-0154271-A1; U.S. Patent Publication No. US-2004-0199059-A1; U.S. Patent Publication No. US-2005-0054909-A1; U.S. Patent Publication No. US-2005-0051427-A1; U.S. Patent Publication No. US-2003-0032874-A1; U.S. Patent Publication No. US-2005-0103625-A1; U.S. Patent Publication No. US-2005-0203360-A1; U.S. Patent Publication No.

US-2005-0090607-A1; U.S. Patent Publication No. US-2005-0187720-A1; U.S. Patent Publication No. US-2005-0161346-A1; U.S. Patent Publication No. US-2006-0015020-A1; U.S. Patent Publication No. US-2005-0043598-A1; U.S. Patent Publication No. US-2005-0033132-A1; U.S. Patent Publication No. US-2005-0031689-A1; U.S. Patent Publication No. US-2004-0186362-A1; U.S. Patent Publication No. US-2005-0027463-A1; U.S. Patent Publication No. US-2005-0027181-A1; U.S. Patent Publication No. US-2005-0027180-A1; U.S. Patent Publication No. US-2006-0020187-A1; U.S. Patent Publication No. US-2006-0036142-A1; U.S. Patent Publication No. US-2006-0020192-A1; U.S. Patent Publication No. US-2006-0036143-A1; U.S. Patent Publication No. US-2006-0036140-A1; U.S. Patent Publication No. US-2006-0019327-A1; U.S. Patent Publication No. US-2006-0020186-A1; U.S. Patent Publication No. US-2006-0036139-A1; U.S. Patent Publication No. US-2006-0020191-A1; U.S. Patent Publication No. US-2006-0020188-A1; U.S. Patent Publication No. US-2006-0036141-A1; U.S. Patent Publication No. US-2006-0020190-A1; U.S. Patent Publication No. US-2006-0036145-A1; U.S. Patent Publication No. US-2006-0036144-A1; U.S. Patent Publication No. US-2006-0016700-A1; U.S. Patent Publication No. US-2006-0142651-A1; U.S. Patent Publication No. US-2006-0086624-A1; U.S. Patent Publication No. US-2006-0068208-A1; U.S. Patent Publication No. US-2006-0040402-A1; U.S. Patent Publication No. US-2006-0036142-A1; U.S. Patent Publication No. US-2006-0036141-A1; U.S. Patent Publication No. US-2006-0036143-A1; U.S. Patent Publication No. US-2006-0036140-A1; U.S. Patent Publication No. US-2006-0036139-A1; U.S. Patent Publication No. US-2006-0142651-A1; U.S. Patent Publication No. US-2006-0036145-A1; U.S. Patent Publication No. US-2006-0036144-A1; U.S. Patent Publication No. US-2006-0200022-A1; U.S. Patent Publication No. US-2006-0198864-A1; U.S. Patent Publication No. US-2006-0200019-A1; U.S. Patent Publication No. US-2006-0189856-A1; U.S. Patent Publication No. US-2006-0200020-A1; U.S. Patent Publication No. US-2006-0200970-A1; U.S. Patent Publication No. US-2006-0183984-A1; U.S. Patent Publication No. US-2006-0183985-A1; U.S. Patent Publication No. US-2006-0195029-A1; U.S. Patent Publication No. US-2006-0229512-A1; U.S. Patent Publication No. US-2006-0222566-A1; U.S. Patent Publication No. US-2007-0032706-A1; U.S. Patent Publication No. US-2007-0016381-A1; U.S. Patent Publication No. US-2007-0027370-A1; U.S. Patent Publication No. US-2007-0027384-A1; U.S. Patent Publication No. US-2007-0032718-A1; U.S. Patent Publication No. US-2007-0059196-A1; U.S. Patent Publication No. US-2007-0066873-A1; U.S. Patent Publication No. US-2007-0093704-A1; U.S. Patent Publication No. US-2007-0197890-A1; U.S. Patent Publication No. US-2007-0173710-A1; U.S. Patent Publication No. US-2007-0163880-A1; U.S. Patent Publication No. US-2007-0203966-A1; U.S. Patent Publication No. US-2007-0213611-A1; U.S. Patent Publication No. US-2007-0232879-A1; U.S. Patent Publication No. US-2007-0235331-A1; U.S. Patent Publication No. US-2008-0021666-A1; U.S. Patent Publication No. US-2008-0033254-A1; U.S. Patent Publication No. US-2008-0045824-A1; U.S. Patent Publication No. US-2008-0071156-A1; U.S. Patent Publication No. US-2008-0086042-A1; U.S. Patent Publication No. US-2008-0086044-A1; U.S. Patent Publication No. US-2008-0086273-A1; U.S. Patent Publication No. US-2008-0083617-A1; U.S. Patent Publication No. US-2008-0119703-A1; and U.S. Patent Publication No. US-2008-0119706-A1.

Methods and devices that are suitable for use in conjunction with aspects of the preferred embodiments are disclosed in U.S. patent application Ser. No. 09/447,227 filed Nov. 22, 1999 and entitled "DEVICE AND METHOD FOR DETERMINING ANALYTE LEVELS"; U.S. patent application Ser. No. 11/654,135 filed Jan. 17, 2007 and entitled "POROUS MEMBRANES FOR USE WITH IMPLANTABLE DEVICES"; U.S. patent application Ser. No. 11/654,140 filed Jan. 17, 2007 and entitled "MEMBRANES FOR AN ANALYTE SENSOR"; U.S. patent application Ser. No. 11/543,490 filed Oct. 4, 2006 and entitled "ANALYTE SENSOR"; U.S. patent application Ser. No. 11/691,426 filed Mar. 26, 2007 and entitled "ANALYTE SENSOR"; U.S. patent application Ser. No. 12/037,830 filed Feb. 26, 2008 and entitled "ANALYTE MEASURING DEVICE"; U.S. patent application Ser. No. 12/037,812 filed Feb. 26, 2008 and entitled "ANALYTE MEASURING DEVICE"; U.S. patent application Ser. No. 12/102,654 filed Apr. 14, 2008 and entitled "SYSTEM AND METHODS FOR PROCESSING ANALYTE SENSOR DATA"; U.S. patent application Ser. No. 12/102,729 filed Apr. 14, 2008 and entitled "SYSTEM AND METHODS FOR PROCESSING ANALYTE SENSOR DATA"; U.S. patent application Ser. No. 12/102,745 filed Apr. 14, 2008 and entitled "SYSTEM AND METHODS FOR PROCESSING ANALYTE SENSOR DATA"; U.S. patent application Ser. No. 12/098,359 filed Apr. 4, 2008 and entitled "SYSTEM AND METHODS FOR PROCESSING ANALYTE SENSOR DATA"; U.S. patent application Ser. No. 12/098,353 filed Apr. 4, 2008 and entitled "SYSTEM AND METHODS FOR PROCESSING ANALYTE SENSOR DATA"; U.S. patent application Ser. No. 12/098,627 filed Apr. 7, 2008 and entitled "SYSTEM AND METHODS FOR PROCESSING ANALYTE SENSOR DATA"; U.S. patent application Ser. No. 12/103,594 filed Apr. 15, 2008 and entitled "BIOINTERFACE WITH MACRO- AND MICRO-ARCHITECTURE"; U.S. patent application Ser. No. 12/111,062 filed Apr. 28, 2008 and entitled "DUAL ELECTRODE SYSTEM FOR A CONTINUOUS ANALYTE SENSOR"; U.S. patent application Ser. No. 12/105,227 filed Apr. 17, 2008 and entitled "TRANSCUTANEOUS MEDICAL DEVICE WITH VARIABLE STIFFNESS"; U.S. patent application Ser. No. 12/101,810 filed Apr. 11, 2008 and entitled "TRANSCUTANEOUS ANALYTE SENSOR"; U.S. patent application Ser. No. 12/101,790 filed Apr. 11, 2008 and entitled "TRANSCUTANEOUS ANALYTE SENSOR"; U.S. patent application Ser. No. 12/101,806 filed Apr. 11, 2008 and entitled "TRANSCUTANEOUS ANALYTE SENSOR"; U.S. patent application Ser. No. 12/113,724 filed May 1, 2008 and entitled "LOW OXYGEN IN VIVO ANALYTE SENSOR"; U.S. patent application Ser. No. 12/113,508 filed May 1, 2008 and entitled "LOW OXYGEN IN VIVO ANALYTE SENSOR"; U.S. patent application Ser. No. 12/055,098 filed Mar. 25, 2008 and entitled "ANALYTE SENSOR"; U.S. patent application Ser. No. 12/054,953 filed Mar. 25, 2008 and entitled "ANALYTE SENSOR"; U.S. patent application Ser. No. 12/055,114 filed Mar. 25, 2008 and entitled "ANALYTE SENSOR"; U.S. patent application Ser. No. 12/055,078 filed Mar. 25, 2008 and entitled "ANALYTE SENSOR"; U.S. patent application Ser. No. 12/055,149 filed Mar. 25, 2008 and entitled "ANALYTE SENSOR";

U.S. patent application Ser. No. 12/055,203 filed Mar. 25, 2008 and entitled "ANALYTE SENSOR"; and U.S. patent application Ser. No. 12/055,227 filed Mar. 25, 2008 and entitled "ANALYTE SENSOR".

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

The term "comprising" as used herein is synonymous with "including," "containing," or "characterized by," and is inclusive or open-ended and does not exclude additional, unrecited elements or method steps.

All numbers expressing quantities of ingredients, reaction conditions, and so forth used in the specification are to be understood as being modified in all instances by the term "about." Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

What is claimed is:

1. An integrated system for monitoring and treating diabetes, the system comprising:
   a medicament injection pen configured for injecting an amount of a medicament into a host, wherein the medicament injection pen comprises a motor; and
   an integrated receiver configured to receive sensor data from a continuous glucose sensor, wherein the sensor data is indicative of a glucose concentration of the host in vivo, wherein the integrated receiver comprises electronics configured to process the sensor data, and wherein the integrated receiver is configured to remotely control the motor.

2. The integrated system of claim 1, wherein the integrated receiver comprises a housing, and wherein the medicament injection pen is detachably connectable to the housing.

3. The integrated system of claim 2, wherein communication between the medicament injection pen and the integrated receiver is initiated based at least in part on detachable connection of the medicament injection pen and the housing.

4. The integrated system of claim 1, further comprising a user interface configured for at least one of input of host information, output of sensor data, or output of medicament therapy.

5. The integrated system of claim 4, wherein the user interface is further configured to display a graphical representation of at least one of sensor data or medicament delivery data, wherein the user interface is further configured to display a solid line representing at least one of a target glucose concentration or a range.

6. The integrated system of claim 1, wherein the electronics are configured to require validation prior to injecting an amount of medicament into the host.

7. The integrated system of claim 1, wherein the integrated receiver is configured to communicate with a single-point glucose monitor via a wired or wireless connection.

8. The integrated system of claim 1, wherein the motor is configured to set an amount of medicament.

9. The integrated system of claim 1, wherein the motor is configured to control a rate of medicament injection into the host.

10. The integrated system of claim 1, wherein the medicament injection pen and the integrated receiver each comprise mutually engaging electrical contacts, and wherein the mutually engaging electrical contacts are configured to allow communication between the medicament injection pen and the integrated receiver.

11. The integrated system of claim 10, wherein the system is configured to initiate communication between the medicament injection pen and the integrated receiver in response to engagement of the electrical contacts.

12. The integrated system of claim 10, wherein the system is configured to communicate medicament delivery data between the medicament injection pen and the integrated receiver in response to engagement of the electrical contacts.

13. The integrated system of claim 1, further comprising a receptacle configured to receive at least one of parts associated with the medicament injection pen or accessories associated with the medicament injection pen.

14. The integrated system of claim 13, wherein at least one of parts associated with the medicament injection pen or accessories associated with the medicament injection pen comprise a medicament cartridge.

15. The integrated system of claim 1, further comprising a medicament injection pen kit, wherein the medicament injection pen kit is configured to receive the medicament injection pen, and wherein the medicament injection pen kit comprises a housing comprising a user interface, and wherein the integrated receiver is located within the housing and operably connected to the user interface.

16. An integrated system for monitoring and treating diabetes, the system comprising:
   a receiver configured to receive sensor data from an operably connected continuous glucose sensor, wherein the continuous glucose sensor is configured to generate sensor data associated with a glucose concentration of a host;
   a medicament delivery device configured to inject an amount of medicament into the host; and
   integrated electronics configured to process the sensor data and to generate and display medicament dosage and effects data on a user interface.

17. The integrated system of claim 16, wherein the medicament dosage and effects data comprises at least one of an amount of medicament or a time of medicament delivery.

18. The integrated system of claim 16, wherein the receiver and the medicament delivery device are integrally formed.

19. The integrated system of claim 18, further comprising a receptacle configured to receive at least one of parts associated with the medicament delivery device or accessories associated with the medicament delivery device.

20. The integrated system of claim 16, wherein the medicament delivery device is detachably connectable to the receiver.

21. The integrated system of claim 20, wherein the medicament delivery device and receiver each comprise mutually engaging electrical contacts, and wherein the mutually engaging electrical contacts are configured to allow communication between the medicament delivery device and the receiver.

22. The integrated system of claim 21, wherein the system is configured to initiate communication between the medicament delivery device and the receiver in response to engagement of the mutually engaging electrical contacts.

23. The integrated system of claim 21, wherein the system is configured to communicate a medicament therapy between the receiver and the medicament delivery device in response to engagement of the mutually engaging electrical contacts.

24. The integrated system of claim 16, further comprising a housing integrally formed with the receiver, wherein the integrated electronics are located with the housing.

25. The integrated system of claim 24, wherein the medicament delivery device is detachably connectable with the housing.

26. The integrated system of claim 16, wherein the integrated electronics are configured to display sensor data on the user interface.

27. The integrated system of claim 26, wherein the receiver comprises a housing, and wherein the user interface is located on the receiver housing.

28. The integrated system of claim 16, further comprising a user interface configured to display the sensor data.

29. The integrated system of claim 16, further comprising a medicament injection pen kit comprising the receiver and the integrated electronics, wherein the medicament injection pen kit is configured to receive the medicament delivery device.

30. The integrated system of claim 29, wherein the integrated electronics are configured to display sensor data on the user interface.

31. The integrated system of claim 29, wherein the medicament injection pen kit further comprises a receptacle configured to receive at least one of a medicament cartridge or a medicament injection pen needle.

32. An integrated system for monitoring and treating diabetes, the system comprising:
  a receiver configured to receive sensor data from an operably connected continuous glucose sensor, wherein the continuous glucose sensor is configured to generate sensor data associated with a glucose concentration of a host;
  integrated electronics configured to process the sensor data and to generate a medicament therapy; and
  a user interface configured to display at least one of the sensor data or the medicament therapy, wherein the user interface comprises a flexible LED screen operably connected to at least one of the receiver or the medicament injection pen, and wherein the integrated electronics are configured to display continuous glucose sensor data on the flexible LED screen.

33. An integrated system for monitoring and treating diabetes, the system comprising:
  a receiver configured to receive sensor data from an operably connected continuous glucose sensor, wherein the continuous glucose sensor is configured to generate sensor data associated with a glucose concentration of a host;
  integrated electronics configured to process the sensor data and to generate a medicament therapy; and
  a user interface configured to display at least one of the sensor data or the medicament therapy, wherein the user interface comprises an image projection system configured to project continuous glucose sensor data onto a surface.

* * * * *

UNITED STATES PATENT AND TRADEMARK OFFICE
CERTIFICATE OF CORRECTION

PATENT NO. : 8,808,228 B2
APPLICATION NO. : 12/133820
DATED : August 19, 2014
INVENTOR(S) : Mark C. Brister et al.

Page 1 of 3

It is certified that error appears in the above-identified patent and that said Letters Patent is hereby corrected as shown below:

On the Title Page

In column 1 (page 5, item 56) line 72, References Cited Under Other Publications, change "artifical" to --artificial--.

In column 2 (page 5, item 56) line 27, References Cited Under Other Publications, change "Thechnol." to --Technol.--.

In column 2 (page 5, item 56) line 67, References Cited Under Other Publications, change "reliablity" to --reliability--.

In column 1 (page 6, item 56) line 8, References Cited Under Other Publications, change "Enzymlology," to --Enzymology,--.

In column 1 (page 6, item 56) line 17, References Cited Under Other Publications, change "artifical" to --artificial--.

In column 1 (page 6, item 56) line 45, References Cited Under Other Publications, change "dynamcs" to --dynamics--.

In column 1 (page 6, item 56) line 48, References Cited Under Other Publications, change "gloguse" to --glucose--.

In column 1 (page 6, item 56) line 49, References Cited Under Other Publications, change "Diabetese" to --Diabetes--.

In column 2 (page 6, item 56) line 3, References Cited Under Other Publications, change "Thechnol." to --Technol.--.

In column 2 (page 6, item 56) line 8, References Cited Under Other Publications, change "Diabetese" to --Diabetes--.

In column 2 (page 6, item 56) line 21, References Cited Under Other Publications, change "inactiviation" to --inactivation--.

Signed and Sealed this
Seventeenth Day of March, 2015

Michelle K. Lee
*Director of the United States Patent and Trademark Office*

CERTIFICATE OF CORRECTION (continued)
U.S. Pat. No. 8,808,228 B2

In column 1 (page 7, item 56) line 45, References Cited Under Other Publications, change "activitiy," to --activity,--.

In column 1 (page 7, item 56) line 59, References Cited Under Other Publications, change "Biosensors& Beioelectronics," to --Biosensors & Bioelectronics,--.

In column 1 (page 7, item 56) line 60, References Cited Under Other Publications, change "glocuse" to --glucose--.

In column 2 (page 7, item 56) line 23, References Cited Under Other Publications, change "artifical" to --artificial--.

In column 2 (page 7, item 56) line 39, References Cited Under Other Publications, change "Thechnol." to --Technol.--.

In column 2 (page 7, item 56) line 69, References Cited Under Other Publications, change "termistor" to --thermistor--.

In column 2 (page 7, item 56) line 70, References Cited Under Other Publications, change "metobolites," to --metabolites,--.

In column 2 (page 7, item 56) line 72, References Cited Under Other Publications, change "cholesteral and cholesteral" to --cholesterol and cholesterol--.

In column 1 (page 8, item 56) line 3, References Cited Under Other Publications, change "Apllied" to --Applied--.

In column 1 (page 8, item 56) line 68, References Cited Under Other Publications, change "Subcutaenous" to --Subcutaneous--.

In column 2 (page 8, item 56) line 9, References Cited Under Other Publications, change "assitance" to --assistance--.

In column 2 (page 8, item 56) line 10, References Cited Under Other Publications, change "Thechnol." to --Technol.--.

In column 2 (page 8, item 56) line 43, References Cited Under Other Publications, change "Thechnol." to --Technol.--.

In column 2 (page 8, item 56) line 58, References Cited Under Other Publications, change "Membrance" to --Membrane--.

In column 2 (page 8, item 56) line 63, References Cited Under Other Publications, change "cholesteral" to --cholesterol--.

In column 1 (page 9, item 56) line 6, References Cited Under Other Publications, change "Deabetes" to --Diabetes--.

In column 2 (page 9, item 56) line 43, References Cited Under Other Publications, change "Senso" to --Sensor--.

In column 2 (page 9, item 56) line 50, References Cited Under Other Publications, change "basedon" to --based--.

In column 2 (page 9, item 56) line 71, References Cited Under Other Publications, change "valication" to --validation--.

In column 2 (page 9, item 56) line 72, References Cited Under Other Publications, change "iunsulin interaaction in tyhpe" to --insulin interaction in type--.

In column 1 (page 10, item 56) line 28, References Cited Under Other Publications, change "Membran," to --Membrane,--.

In column 2 (page 10, item 56) line 64, References Cited Under Other Publications, change "patents" to --patients--.

In column 1 (page 11, item 56) line 55, References Cited Under Other Publications, change "pancrease" to --pancreas--.

In column 2 (page 11, item 56) line 20, References Cited Under Other Publications, change "Tranducers" to --Transducers--.

In column 2 (page 12, item 56) line 16, References Cited Under Other Publications, change "Measurment:" to --Measurement:--.

In column 2 (page 12, item 56) line 49, References Cited Under Other Publications, change "Effets" to --Effects--.

In the Specification

In column 2 line 7, Change "in vivo" to --in vivo,--.

In column 11 line 62, Change "and or" to --and/or--.

In column 16 line 10, Change "radiometric" to --radiometric,--.

In column 16 line 38, Change "thereof" to --thereof.--.

In column 25 line 25, Change "in vivo" to --in vivo,--.

In column 29 line 39, Change "at" to --as--.

In column 33 line 37, Change "entirety" to --entirety.--.